US008840621B2

(12) United States Patent
Farr et al.

(10) Patent No.: US 8,840,621 B2
(45) Date of Patent: Sep. 23, 2014

(54) SPINAL ACCESS SYSTEMS AND METHODS

(75) Inventors: Morteza M. Farr, Santa Cruz, CA (US);
Ephraim Akyuz, Logan, UT (US); T. Wade Fallin, Hyde Park, UT (US);
Daniel F. Justin, Logan, UT (US);
Joshua A. Butters, Chandler, AZ (US);
Daniel E. Gerbec, Logan, UT (US)

(73) Assignee: Innovative Spine, Inc., Clovis, CA (US)

( * ) Notice: Subject to any disclaimer, the term of this patent is extended or adjusted under 35 U.S.C. 154(b) by 1102 days.

(21) Appl. No.: 12/357,596

(22) Filed: Jan. 22, 2009

(65) Prior Publication Data

US 2009/0216234 A1    Aug. 27, 2009

Related U.S. Application Data

(63) Continuation-in-part of application No. 11/831,698, filed on Jul. 31, 2007, now Pat. No. 8,025,664, and a (Continued)

(51) Int. Cl.
*A61B 17/56*    (2006.01)
*A61B 17/02*    (2006.01)

(Continued)

(52) U.S. Cl.
CPC ....... *A61B 17/025* (2013.01); *A61B 2019/5221* (2013.01); *A61B 17/320708* (2013.01); *A61B 2017/0256* (2013.01); *A61F 2/4611* (2013.01); *A61F 2002/30538* (2013.01); *A61B 2017/2904* (2013.01); *A61F 2250/0006* (2013.01); *A61B 17/3421* (2013.01); *A61F 2002/4681* (2013.01); *A61B 17/3468* (2013.01); *A61B 2017/320056* (2013.01); *A61F 2/4684* (2013.01); *A61F 2230/0006* (2013.01); *A61B 19/5212* (2013.01); *A61F 2002/30904* (2013.01); *A61B 2017/320044* (2013.01); *A61F 2002/30116* (2013.01); *A61F 2002/4435* (2013.01); *A61B 17/1659* (2013.01); *A61F 2002/30616* (2013.01); *A61F 2002/4627* (2013.01); *A61F 2/4455* (2013.01); *A61F 2/4601* (2013.01); *A61F 2/447* (2013.01); *A61B 19/26* (2013.01); *A61B 17/1604* (2013.01); *A61B 2017/3447* (2013.01)
USPC ......................................................... 606/99

(58) Field of Classification Search
USPC ..... 606/86 A, 86 R, 90, 99; 623/17.11–17.16
See application file for complete search history.

(56) References Cited

U.S. PATENT DOCUMENTS 2,338,159 A    1/1944  Appleton
2,697,433 A   12/1954  Zhender (Continued)

OTHER PUBLICATIONS

International Search Report and Written Opinion From Corresponding PCT Application No. PCT/US2009/031751, Aug. 26, 2009 (13 pgs).

*Primary Examiner* — Christian Sevilla
(74) *Attorney, Agent, or Firm* — GSS Law Group

(57) ABSTRACT

A system for accessing a spine from a curved postero-lateral approach may include a curved cannula positioned along a curved path from an opening in the skin to a location proximate the spine. The location may be at the L4-L5 vertebral level, and the curved path may lie in a plane oblique to the transverse, coronal and sagittal planes of the spine, and avoid the iliac crest. A targeting post may be inserted adjacent the spine to determine the location, and a guide member may be inserted to establish the curved path. A micrometer assembly may adjust a cephalad-caudal displacement between the post and the guide member. One or more intermediate cannulas may be inserted over the guide member to dilate tissues prior to insertion of the main cannula. An interbody device may be implanted into an intervertebral space through the cannula.

13 Claims, 69 Drawing Sheets

Related U.S. Application Data continuation-in-part of application No. 11/831,728, filed on Jul. 31, 2007, now Pat. No. 8,057,481, and a continuation-in-part of application No. 11/934,636, filed on Nov. 2, 2007.

(60) Provisional application No. 60/856,682, filed on Nov. 3, 2006, provisional application No. 61/023,030, filed on Jan. 23, 2008, provisional application No. 61/050,523, filed on May 5, 2008, provisional application No. 61/086,940, filed on Aug. 7, 2008.

(51) Int. Cl.
*A61F 2/46* (2006.01)
*A61B 17/34* (2006.01)
*A61B 17/16* (2006.01)
*A61B 19/00* (2006.01)
*A61B 17/3207* (2006.01)
*A61F 2/30* (2006.01)
*A61B 17/29* (2006.01)
*A61B 17/32* (2006.01)
*A61F 2/44* (2006.01)

(56) References Cited

U.S. PATENT DOCUMENTS

| | | |
|---|---|---|
| 3,090,386 A | 5/1963 | Curtis |
| 3,556,103 A | 1/1971 | Calhoun et al. |
| 3,570,498 A | 3/1971 | Weighton |
| 3,608,539 A | 9/1971 | Miller |
| 3,892,232 A | 7/1975 | Neufeld |
| 3,941,127 A | 3/1976 | Froning |
| 3,946,740 A | 3/1976 | Basset |
| 3,948,274 A | 4/1976 | Zeldman et al. |
| 3,964,480 A | 6/1976 | Froning |
| 4,265,231 A | 5/1981 | Scheller, Jr. et al. |
| 4,312,337 A | 1/1982 | Donohue |
| 4,335,715 A | 6/1982 | Kirkley |
| 4,409,968 A | 10/1983 | Drummond |
| 4,448,191 A | 5/1984 | Rodnyansky et al. |
| 4,511,356 A | 4/1985 | Froning et al. |
| 4,541,423 A | 9/1985 | Barber |
| 4,545,374 A | 10/1985 | Jacobson |
| 4,573,448 A | 3/1986 | Kambin |
| 4,598,705 A | 7/1986 | Lichtenberger |
| 4,686,972 A | 8/1987 | Kurland |
| 4,722,331 A | 2/1988 | Fox |
| 4,756,708 A | 7/1988 | Martin |
| 4,863,430 A | 9/1989 | Klyce et al. |
| 4,883,048 A | 11/1989 | Purnell et al. |
| 4,896,661 A | 1/1990 | Bogert et al. |
| 4,926,860 A | 5/1990 | Stice et al. |
| 4,941,466 A | 7/1990 | Romano |
| 4,957,495 A | 9/1990 | Klunger |
| 5,080,662 A | 1/1992 | Paul |
| 5,163,940 A | 11/1992 | Bourque |
| 5,242,444 A | 9/1993 | MacMillan |
| 5,285,795 A | 2/1994 | Ryan |
| 5,300,077 A | 4/1994 | Howell |
| 5,330,468 A | 7/1994 | Burkhart |
| 5,334,205 A | 8/1994 | Cain |
| 5,458,602 A | 10/1995 | Goble et al. ............... 606/96 |
| 5,601,562 A | 2/1997 | Wolf |
| 5,613,971 A | 3/1997 | Lower |
| 5,725,532 A | 3/1998 | Shoemaker |
| 5,741,261 A | 4/1998 | Moskovitz et al. |
| 5,891,147 A | 4/1999 | Moskovitz et al. |
| 6,042,582 A | 3/2000 | Ray |
| 6,080,155 A | 6/2000 | Michelson |
| 6,083,225 A | 7/2000 | Winslow |
| 6,205,699 B1 * | 3/2001 | Bogni ........................ 43/53.5 |
| 6,224,603 B1 | 5/2001 | Marino |
| 6,226,548 B1 | 5/2001 | Foley et al. |
| 6,419,678 B1 | 7/2002 | Asfora |
| 6,443,988 B2 | 9/2002 | Felt et al. |
| 6,530,929 B1 | 3/2003 | Justis et al. |
| 6,547,795 B2 | 4/2003 | Schneiderman |
| 6,575,899 B1 | 6/2003 | Foley et al. |
| 6,592,559 B1 | 7/2003 | Pakter et al. |
| 6,604,003 B2 | 8/2003 | Fredricks et al. |
| 6,638,276 B2 | 10/2003 | Sharkey et al. |
| 6,669,698 B1 | 12/2003 | Tromanhauser et al. |
| 6,689,140 B2 | 2/2004 | Cohen |
| 6,733,496 B2 | 5/2004 | Sharkey et al. |
| 6,740,090 B1 | 5/2004 | Cragg et al. |
| 6,764,491 B2 | 7/2004 | Frey et al. |
| 6,790,210 B1 | 9/2004 | Cragg et al. |
| 6,824,565 B2 | 11/2004 | Muhanna et al. |
| 6,830,570 B1 | 12/2004 | Frey et al. |
| 6,875,219 B2 | 4/2005 | Arramon et al. |
| 6,980,862 B2 | 12/2005 | Fredricks et al. |
| 7,008,422 B2 | 3/2006 | Foley et al. |
| 7,011,660 B2 | 3/2006 | Sherman et al. |
| RE39,133 E | 6/2006 | Clayton et al. |
| 7,060,068 B2 | 6/2006 | Tromanhauser et al. |
| 7,060,073 B2 | 6/2006 | Frey et al. |
| 7,074,226 B2 | 7/2006 | Roehm et al. |
| 2002/0013514 A1 | 1/2002 | Brau |
| 2002/0019637 A1 | 2/2002 | Frey et al. |
| 2002/0065541 A1 | 5/2002 | Fredricks et al. |
| 2002/0091387 A1 | 7/2002 | Hoogland |
| 2002/0156420 A1 | 10/2002 | Anderson et al. |
| 2002/0161368 A1 | 10/2002 | Foley et al. |
| 2002/0165550 A1 | 11/2002 | Frey et al. |
| 2003/0032929 A1 | 2/2003 | McGuckin |
| 2003/0074005 A1 | 4/2003 | Roth et al. ................ 606/99 |
| 2003/0120308 A1 | 6/2003 | Loubens |
| 2003/0191474 A1 | 10/2003 | Cragg et al. |
| 2003/0199871 A1 | 10/2003 | Foley et al. |
| 2003/0208202 A1 | 11/2003 | Falahee |
| 2003/0229347 A1 | 12/2003 | Sherman et al. ........... 606/61 |
| 2004/0015215 A1 | 1/2004 | Fredricks et al. |
| 2004/0030346 A1 | 2/2004 | Frey et al. |
| 2004/0034351 A1 | 2/2004 | Sherman et al. |
| 2004/0038242 A1 | 2/2004 | Edmonds et al. |
| 2004/0092928 A1 | 5/2004 | Sasso |
| 2004/0106997 A1 | 6/2004 | Lieberson |
| 2004/0117020 A1 | 6/2004 | Frey et al. |
| 2004/0133168 A1 | 7/2004 | Salcudean et al. |
| 2004/0153005 A1 | 8/2004 | Krueger |
| 2004/0162559 A1 | 8/2004 | Arramon |
| 2004/0199168 A1 | 10/2004 | Bertagnoli et al. |
| 2004/0215190 A1 | 10/2004 | Nguyen et al. |
| 2004/0220577 A1 | 11/2004 | Cragg et al. |
| 2005/0021031 A1 | 1/2005 | Foley et al. |
| 2005/0137605 A1 | 6/2005 | Assell et al. |
| 2005/0137612 A1 | 6/2005 | Assell et al. |
| 2005/0149035 A1 | 7/2005 | Pimenta et al. |
| 2005/0171540 A1 | 8/2005 | Lim et al. |
| 2005/0177239 A1 | 8/2005 | Steinberg |
| 2005/0187543 A1 | 8/2005 | Underwood et al. |
| 2005/0209610 A1 | 9/2005 | Carrison |
| 2005/0256578 A1 | 11/2005 | Blatt et al. ............. 623/17.15 |
| 2005/0261773 A1 | 11/2005 | Ferree |
| 2006/0009780 A1 | 1/2006 | Foley et al. |
| 2006/0036241 A1 | 2/2006 | Siegal |
| 2006/0036273 A1 | 2/2006 | Siegal |
| 2006/0052848 A1 | 3/2006 | Fredricks et al. |
| 2006/0064101 A1 | 3/2006 | Arramon |
| 2006/0084977 A1 | 4/2006 | Lieberman |
| 2006/0111714 A1 | 5/2006 | Foley |
| 2006/0111728 A1 | 5/2006 | Abdou ........................ 606/86 |
| 2006/0129101 A1 | 6/2006 | McGuckin, Jr. et al. |
| 2006/0135915 A1 | 6/2006 | Tucker |
| 2006/0135916 A1 | 6/2006 | Tucker |
| 2006/0149278 A1 * | 7/2006 | Abdou ........................ 606/90 |
| 2006/0189986 A1 | 8/2006 | Sherman et al. |
| 2006/0195102 A1 | 8/2006 | Malandain |

(56) References Cited

U.S. PATENT DOCUMENTS

2006/0200129 A1 9/2006 Denti
2006/0200135 A1 9/2006 Sherman et al.
2006/0217806 A1 9/2006 Peterman et al.
2006/0217807 A1 9/2006 Peterman et al.
2006/0229614 A1 10/2006 Foley et al.
2006/0264968 A1 11/2006 Frey et al.

* cited by examiner

SPINAL ACCESS SYSTEMS AND METHODS

CROSS-REFERENCE TO RELATED APPLICATIONS

This application is a continuation-in-part of:

Pending prior U.S. patent application Ser. No. 11/831,698 filed Jul. 31, 2007 and entitled SYSTEM AND METHOD FOR PROVIDING SURGICAL ACCESS TO A SPINE, Pending prior U.S. patent application Ser. No. 11/831,728, filed Jul. 31, 2007 and entitled SYSTEM AND METHOD FOR PROVIDING SURGICAL ACCESS TO A SPINE, and Pending prior U.S. patent application Ser. No. 11/934,636 filed Nov. 2, 2007 and entitled INSTRUMENTATION AND METHOD FOR PROVIDING SURGICAL ACCESS TO A SPINE, each of which claims the benefit of:

U.S. Provisional Patent Application No. 60/856,682, filed Nov. 3, 2006, and is entitled METHOD AND APPARATUS FOR SPINAL SURGERY.

This application also claims the benefit of the following:

prior U.S. Provisional Patent Application No. 61/023,030, filed Jan. 23, 2008, and is entitled SYSTEMS AND METHODS FOR SURGICAL ACCESS AND VISUALIZATION;

prior U.S. Provisional Patent Application No. 61/050,523, filed May 5, 2008, and is entitled SPINAL ACCESS SYSTEMS AND METHODS; and prior U.S. Provisional Patent Application No. 61/086,940, filed Aug. 7, 2008, and is entitled SYSTEMS AND METHODS FOR SURGICAL ACCESS AND VISUALIZATION.

The above-identified documents are incorporated herein by reference.

BACKGROUND OF THE INVENTION

1. The Field of the Invention

The invention relates to orthopaedics, and more particularly, to systems and methods for providing access to the spine to facilitate various implantation procedures.

2. The Relevant Technology

Many spinal orthopaedic procedures including discectomy, implantation of motion preservation devices, total disc replacement, and implantation of interbody devices require unimpeded access to a targeted portion of the spinal column. A lateral interbody fusion approach requires the patient to be turned mid-process to complete the disc and interbody device procedures and posterior hardware stabilization procedures. An anterior approach requires the presence of a vascular surgeon or highly experienced general surgeon, due to the risk of injury to vascular anatomy. Accordingly, there is a need in the art for systems and methods that facilitate access to the spine, thereby simplifying surgical procedures and expediting patient recovery.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for accessing intervertebral space and inserting spine implants between vertebral bodies. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

The present invention provides access to the spine through the use of postero-lateral approaches. A minimally invasive dilation and/or access device employing such an approach would have significant advantages in spinal orthopaedic procedures over the lateral and anterior approaches. These advantages may include avoiding the need to turn the patient during surgery, less muscle retraction, less blood loss, less operating room time, minimized damage to the vascular system, organs, nerves and muscles, faster recovery, and an improved overall outcome for the patient.

Figure 1:
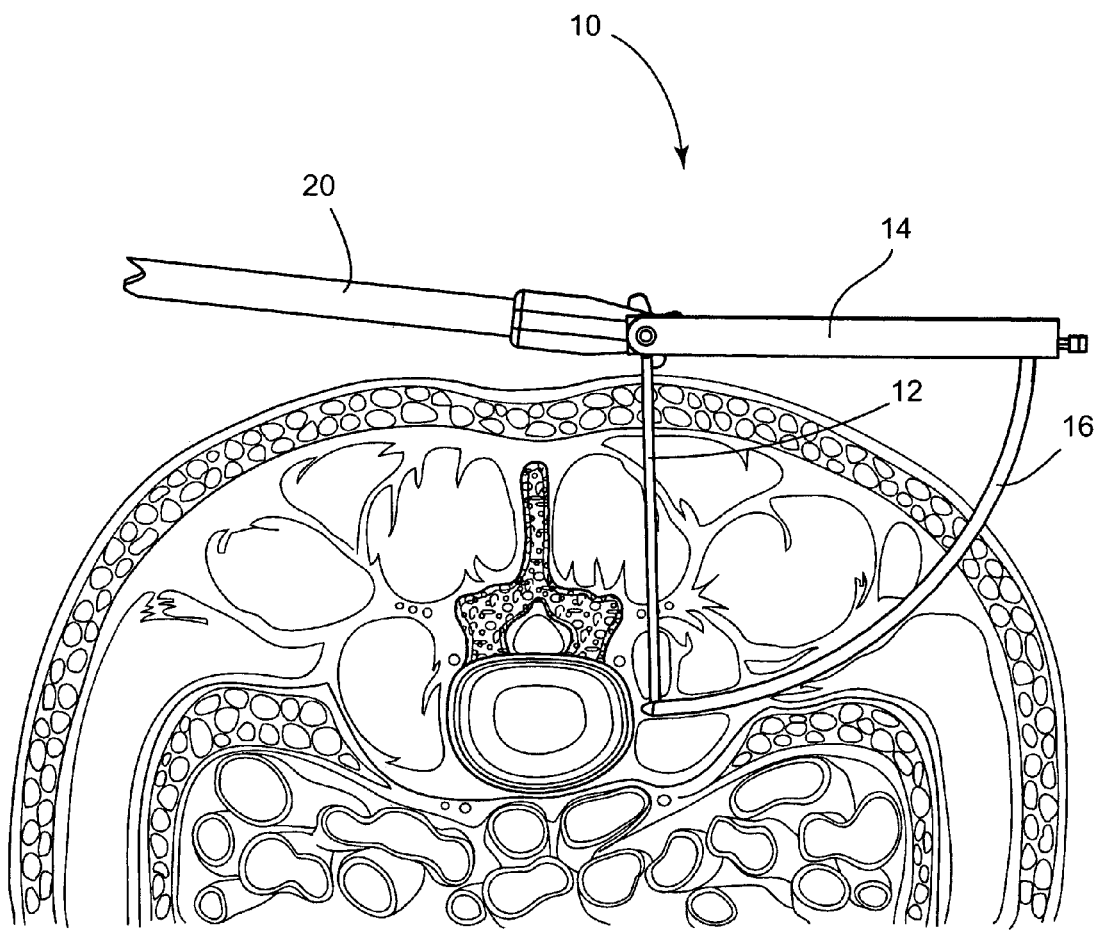
FIG. 1 is a cephalad view of a cross-section of a portion of a patient with an arcuate cannula assembly deployed adjacent a portion of the spine.

Referring to FIG. 1, one embodiment of an arcuate cannula assembly 10 is shown. The assembly 10 comprises a targeting post 12, a guide arm 14, and a curved penetrating guide member 16. An instrument support arm 20 holds the assembly and connects to an operating table (not shown). The assembly 10 may further comprise a series of graduated curved cannulas (not shown in FIG. 1), which are introduced sequentially over the guide member 16 to create access to a targeted portion of a spine. Use of the arcuate cannula assembly 10 creates an access portal to the intervertebral disc space or any element of the anterior spinal column through an arcuate path, from a postero-lateral approach. The access portal is an unimpeded passage through which surgical instruments, implants and other materials may be passed to complete a variety of intervertebral procedures. This arcuate postero-lateral approach may be advantageous in performing a number of procedures, including but not limited to: implantation of motion preservation devices, total disc replacement, implantation of interbody devices, discectomy, lateral plating with or without dynamic elements, vertebra fixation or graft compression using plates or staples, foraminotomy, decompression, annulotomy, nucleotomy, annulus or nucleus repair, vertebral body biopsy, vertebroplasty, height restoration of a collapsed vertebral body (vertebral body augmentation), implantation of a fusion cage with stabilization features, implantation of a fusion cage with teeth to hold endplates together, or implantation of a curved or straight staple across the disc space to provide compression on the cage and stabilization of the cage.

Figure 2:
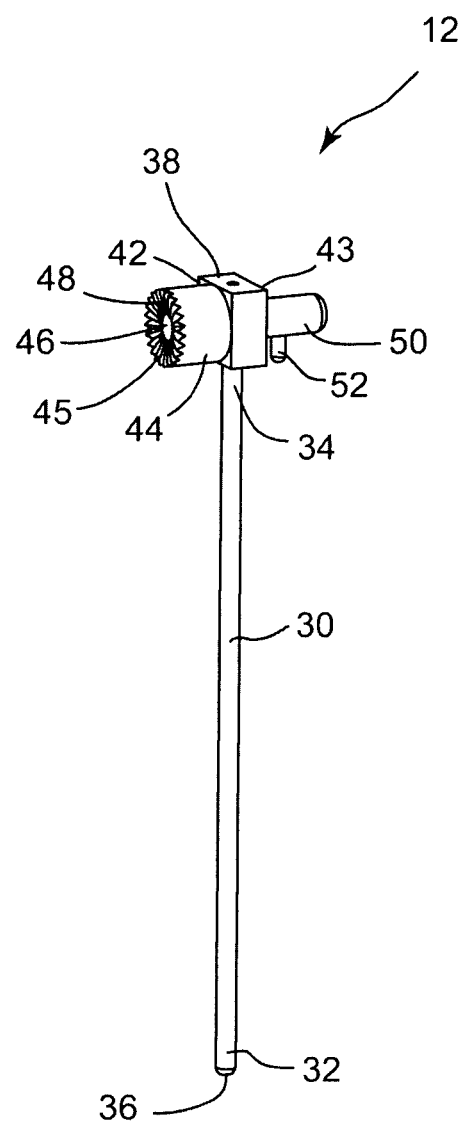
FIG. 2 is a perspective view of a targeting post of the arcuate cannula assembly of FIG. 1.

Referring to FIG. 2, a perspective view of the targeting post 12 is shown. The targeting post 12 comprises an elongate shaft 30 with a distal end 32 and a proximal end 34. A rounded tip 36 is at the terminus of the distal end 32. The proximal end 34 adjoins a rectangular connector block 38 which has a first side 42 and a second side 43. Adjoining the connector block 38 on the first side 42 is a support arm attachment post 44. The attachment post 44 has a receiving slot 46 which extends transversely into the attachment post through an interface surface 45. In the preferred embodiment the receiving slot 46 includes an internally threaded surface. A radial spline 48 encircles the receiving slot 46 on the interface surface 45. Adjoining the connector block 38 on the second side 43 is a rotation post 50. Extending distally from the rotation post 50 is an optional stop feature 52. An alternative embodiment may include a targeting post with a polyaxial joint, enabling the support arm 20 and/or guide arm 14 to be oriented at an angle relative to the targeting post.

Figure 3:
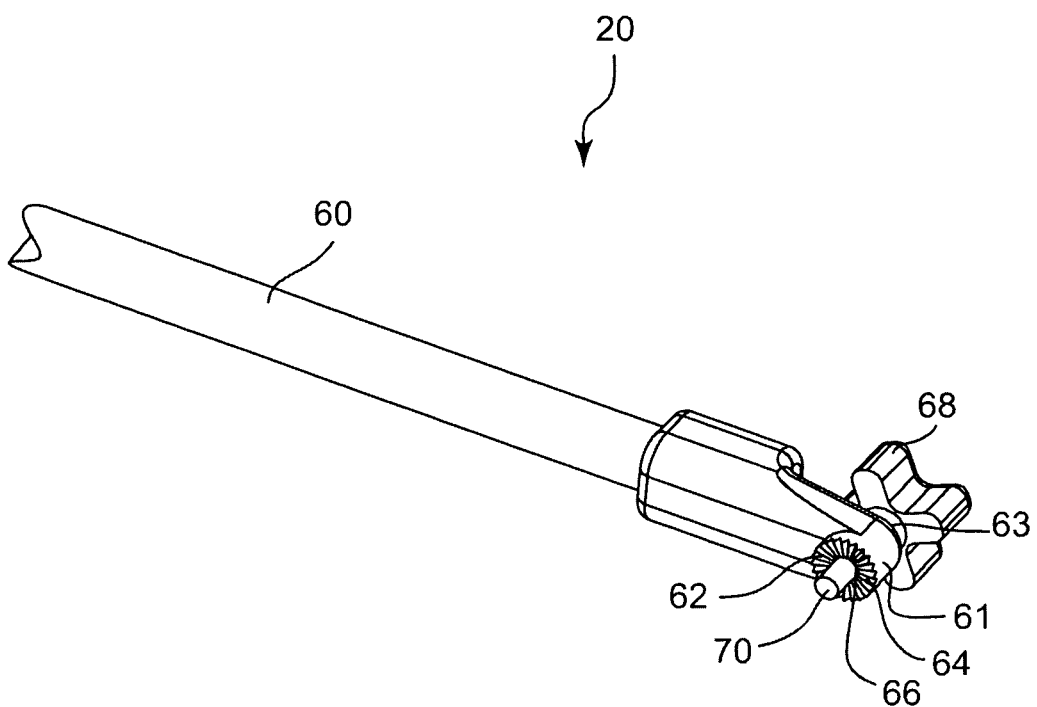
FIG. 3 is a perspective view of a portion of an instrument support arm.

Referring to FIG. 3, a perspective view of a support arm 20 is shown. The support arm 20 comprises a shaft 60 which attaches to the operating table via various linkages, pivots, or connections to allow multiple degrees of freedom to accommodate the positioning of the instrument to be held. A wide variety of differently-configured instrument support arms are well known in the art and the assembly 10 may be compatible with the instrument support arm of choice for the surgeon.

A distal end 61 of the shaft 60 has a first side 62 and a second side 63. Extending transversely through the distal end 61 from the first side 62 to the second side 63 is a screw channel 66. On the first side 62, an interface surface 65 has a radial spline 64 which encircles the opening of the screw channel 66. The radial spline 64 is configured to mate with the radial spline 48 on the targeting post 12 when the post is connected to the support arm 20. Extending through the channel 66 is a thumb screw 68, and a shaft 70 protrudes from the channel 66 on the second side 63. In the preferred embodiment, shaft 70 includes an externally threaded surface configured to interface with the threaded receiving slot 46 on the targeting post 12.

Figure 4:
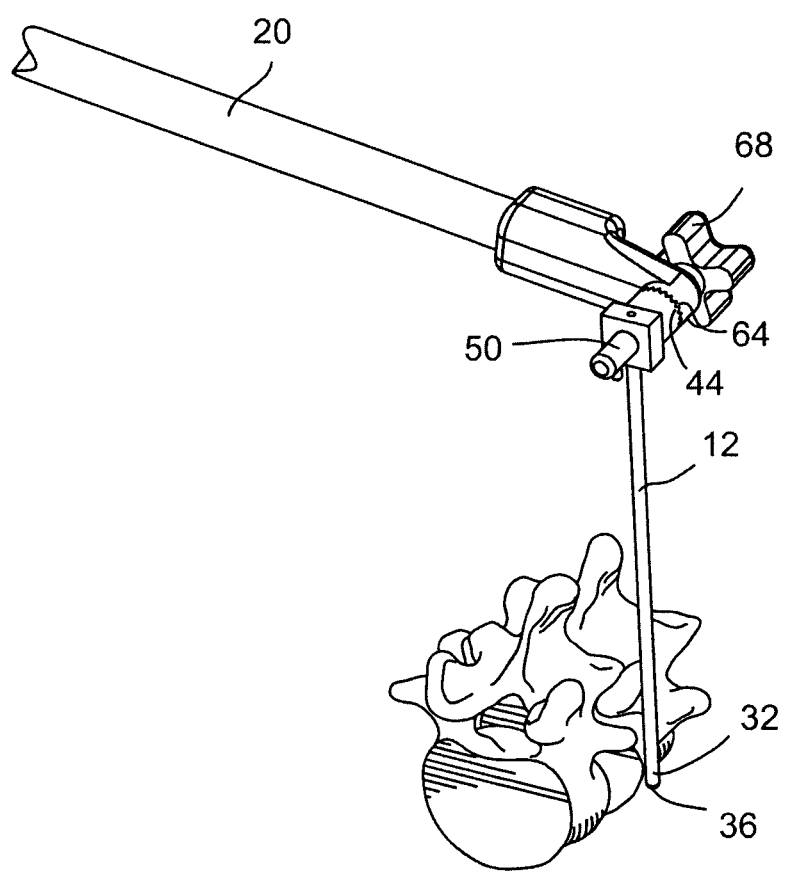
FIG. 4 is a perspective view of the instrument support arm of FIG. 3 supporting the targeting post of FIG. 2 adjacent a portion of a spine.

Referring to FIG. 4, the targeting post 12 is introduced into the patient from a postero-lateral approach through a small incision on the patient's back posterior to the targeted spine segment. The distal end 32 of the targeting post 12 is advanced antero-medially through the patient just lateral to the targeted intervertebral disc until the tip 36 reaches a desired reference location at the anterior lateral half or one third of the disc. The blunt shape of the tip 36 gently pushes tissues aside as the post 12 is advanced in. The post 12 may also be wired as an electrode during insertion, allowing for nerve monitoring or electromyography (EMG) to avoid nerves as the post 12 advances through the tissues. Of special concern is avoidance of the nerve roots exiting the spinal column as the psoas muscle adjacent to the spine is penetrated by the post 12. The targeting post 12 is inserted so that it is coplanar with the superior endplate of the inferior vertebral body for the intervertebral level to be treated. Preferably, the post 12 is aligned parallel with the sagittal plane of the patient, but other orientations are possible if necessary to avoid nerves or other obstacles. The targeting post 12 may be available in a variety of lengths to accommodate patients of differing proportions, and to reach specific reference locations.

When the distal end 32 of the targeting post 12 has reached the reference location, the proximal end 30 is attached to the support arm 20 via the thumb screw 68. The protruding screw shaft 70 is threaded into the receiving slot 46. As the thumb screw 68 is threaded in, the radial splines 44, 64 mesh, locking the targeting post 12 to the support arm 20. Once attachment is made between the targeting post 12 and the support arm 20, the various degrees of freedom of the support arm 20 are locked down to provide sufficiently rigid instrument stabilization. In position adjacent to the spine, the targeting post 12 acts as a stabilizing and reference guide for subsequent cannulas, instruments and implants. The targeting post 12 may optionally be affixed to the patient to provide additional stability.

Figure 5:
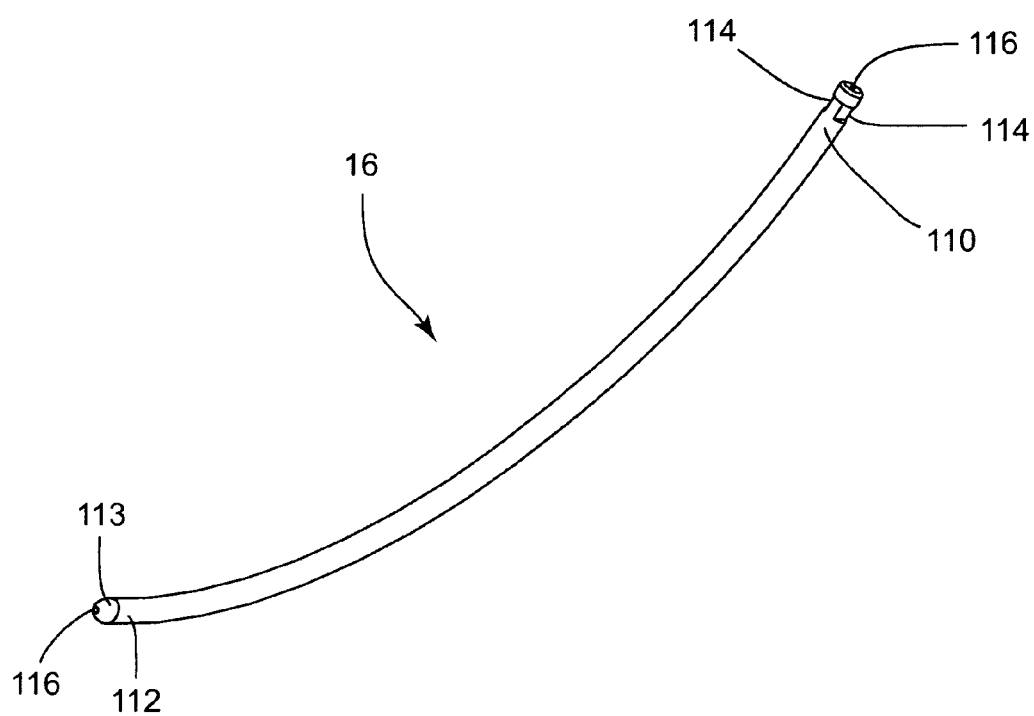
FIG. 5 is a perspective view of a guide member of the arcuate cannula assembly of FIG. 1.

Referring to FIG. 5, the penetrating guide member 16 is shown. The guide member 16 is curved and may be arcuate (i.e., may extend along a fixed radius of curvature). The guide member 16 has a proximal end 110, and a distal end 112 with an insertion tip 113. The insertion tip 113 may be rounded or optionally pointed, to penetrate muscles and fascia. Two attachment recesses 114 at the proximal end facilitate attaching the guide member 16 to the guide arm 14, and are also configured to connect to an instrument support arm. A narrow channel may optionally extend the length of the guide member 16, sized to receive a wire for nerve monitoring or EMG during dilation.

Figure 6A:
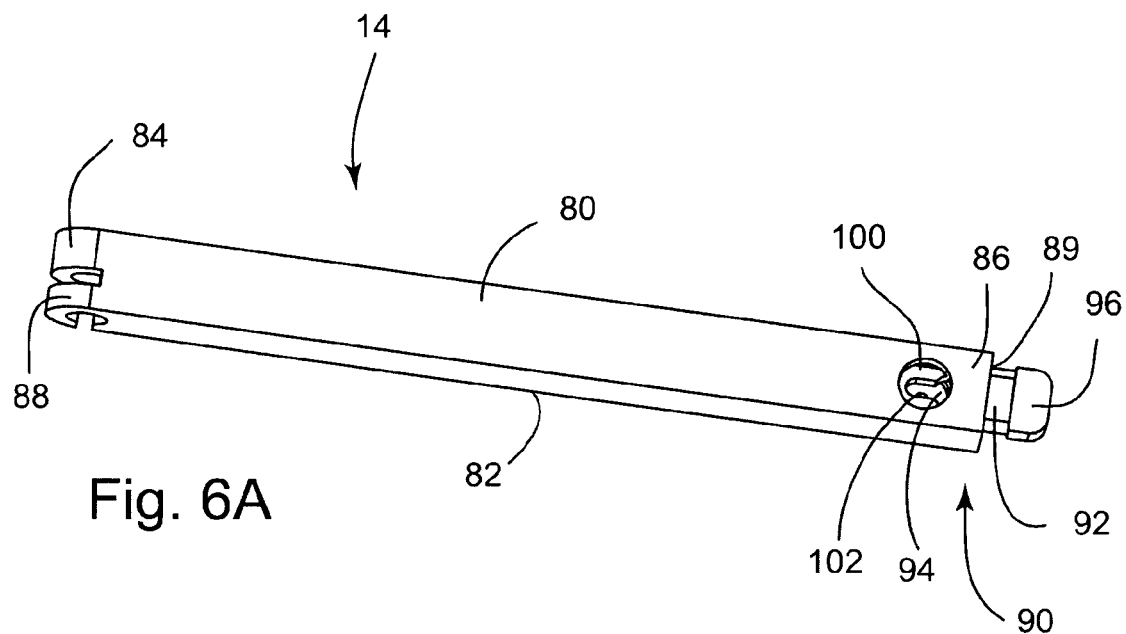
FIG. 6A is a perspective view of a guide arm of the arcuate cannula assembly of FIG. 1.

Referring to FIG. 6A, a perspective view of the guide arm 14 is shown. The guide arm 14 has a first side 80 and a second side 82. At a proximal end is a pinned end 84; a latch end 86 is at the opposite distal end. The pinned end 84 has an attachment feature 88 which is shaped to rotatably attach to the rotation post 50 on the targeting post 12. Inserted into a horizontal slot 89 in the latch end 86 is a spring loaded guide member latch assembly 90 which is shaped to grip the penetrating guide member 16. The guide member latch assembly 90 has a sliding latch bar 92 with a keyhole 94 and a tab 96. On the first side 80 of the guide arm 14, near the latch end 86 is a round guide member opening 100. Directly opposite it on the second side 82 may optionally be a smaller pinhole opening 102.

Figure 6B:
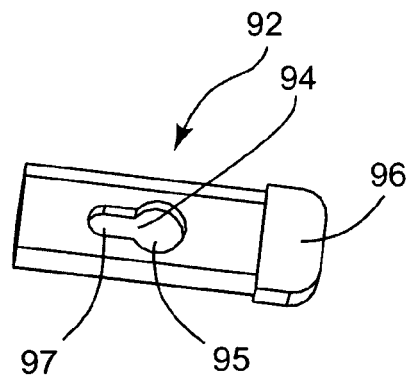
FIG. 6B is a perspective view of a sliding latch bar of the guide arm of FIG. 6A.

FIG. 6B is an enlarged view of the sliding latch bar 92. Keyhole 94 has a rounded lobe 95 disposed toward the tab 96, and an ovoid lobe 97 opposite the tab 96. The rounded lobe 95 is sized to fit around the proximal end 110 of the guide member 16 (not shown). The ovoid lobe 97 is sized to hold the attachment recesses 114 of the guide member 16. The tab 96 may be grasped to move the sliding latch bar 92 within the horizontal slot 89. A spring (not shown) is disposed in the horizontal slot 89 to provide resistance against the sliding latch bar 92.

Figure 7:
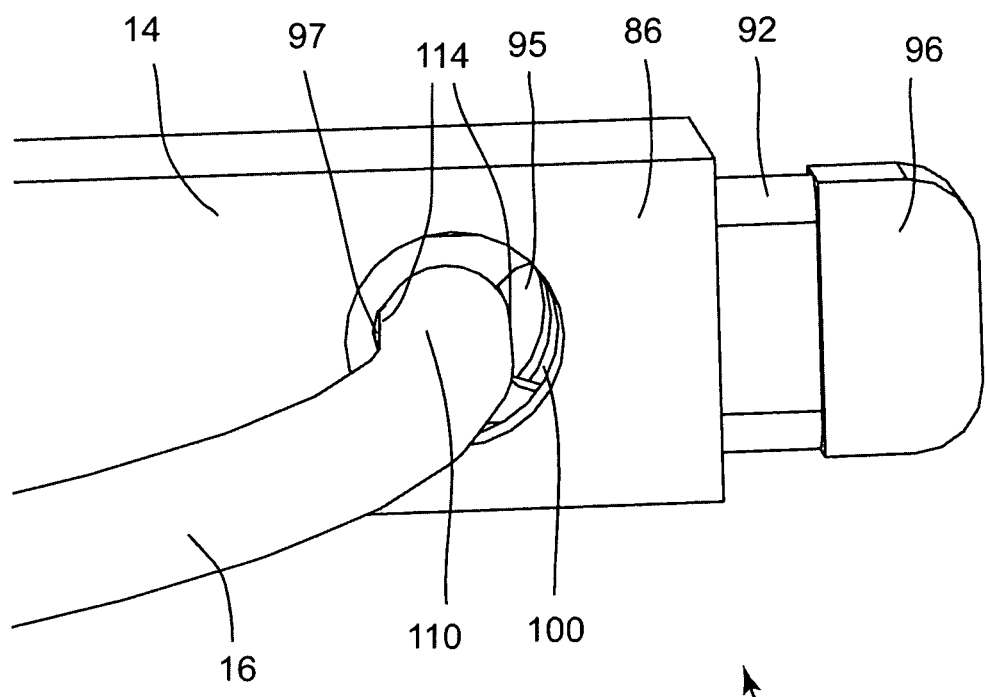
FIG. 7 is a perspective view of a latch assembly of FIG. 6A, with the guide member of FIG. 5 latched thereto.

FIG. 7 is an enlarged view of the latch end 86 of the guide arm 14, showing the guide member 16 latched in the latch assembly 90. To latch the guide member 16 in the latch assembly 90, first the sliding latch bar 92 is introduced into the horizontal slot 89 until the rounded lobe 95 of the keyhole 94 lines up with the guide member opening 100. The proximal end 110 of the guide member 16 is inserted such that the attachment recesses 114 are adjacent to the lined up keyhole 94 and opening 100. The sliding latch bar 92 is released, and the spring (not shown) pushes the sliding latch bar 92 distally until the ovoid lobe 97 of the keyhole 94 slides around the attachment recesses 114 of the guide member 16. The force of the spring traps the guide member 16 in the latch assembly 90, as the guide member is pinned between the ovoid lobe 97 and the latch end 86 of the guide bar 14 adjacent the guide member opening 100.

Figure 8:
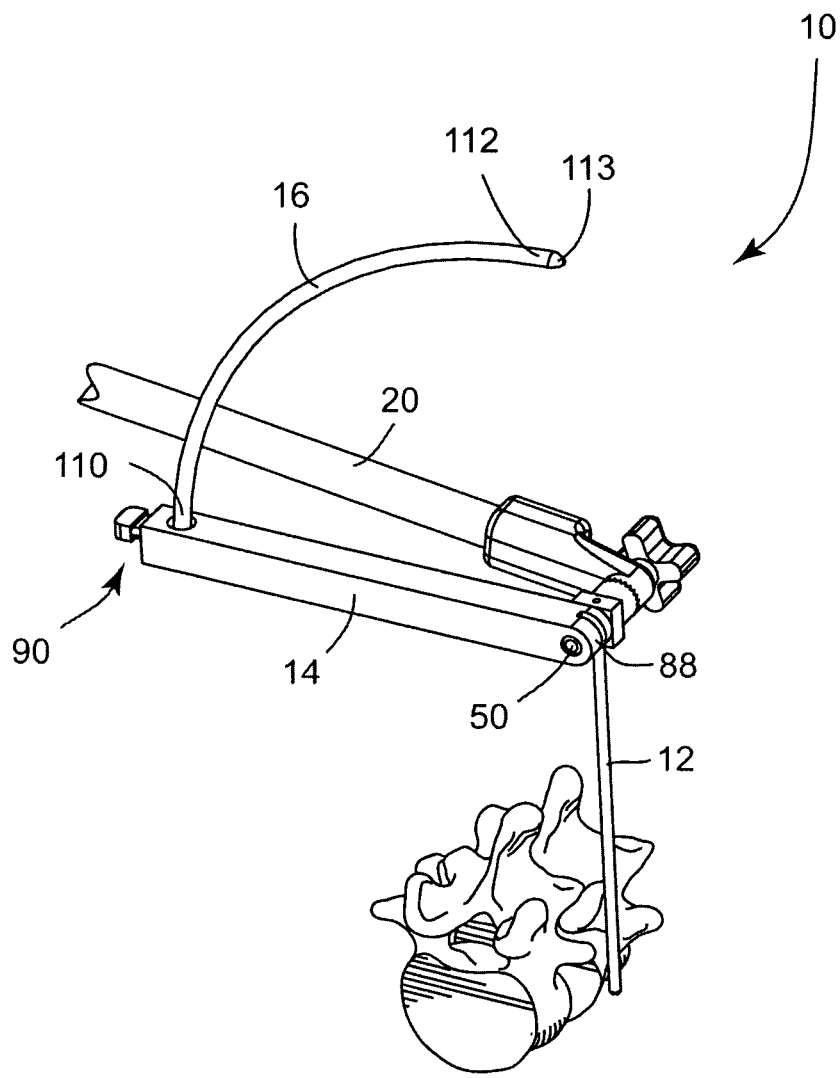
FIG. 8 is a perspective view of the arcuate cannula assembly of FIG. 1 with the guide arm in a first position, adjacent a portion of the spine.

Referring to FIG. 8, the support arm 20, targeting post 12, guide arm 14 and penetrating guide member 16 are shown, with the guide arm 14 and penetrating guide member 16 in a first position. The attachment feature 88 on the guide arm 14 is engaged with the rotation post 50 on the targeting post 12. Thus attached, the guide arm 14 can rotate about the axis of the rotation post 50; however the stop feature 52 on the rotation post 50 may prevent the guide arm 14 from rotating entirely about the rotation post 50. The guide arm 14 may be sized to match the radius of the curve of the penetrating guide member 16, such that the arc centerpoint of the penetrating guide member 16 is coincident with the center of rotation, or axis of the rotation post 50. The guide member latch 90 holds the penetrating guide member 16 as seen in FIG. 7.

After the penetrating guide member 16 is attached to the guide arm 14, the guide arm 14 is rotated so that the insertion tip 113 of the guide member 16 makes contact with the skin. Optionally, an incision location may be marked on the skin. At this point, the guide member 16 is lifted and an incision of approximately 1-5 cm is made into the skin and fascia. Following the incision, the surgeon may insert a finger into the incision to locate and palpate the soft tissues and fascia.

Figure 9:
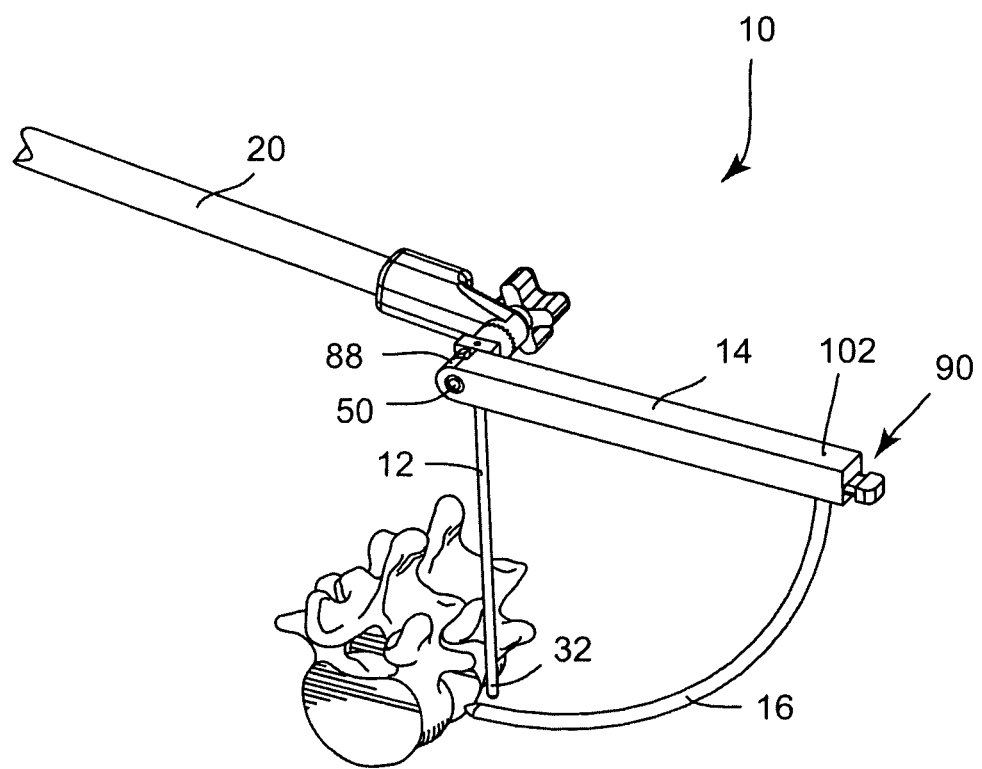
FIG. 9 is a perspective view of the arcuate cannula assembly of FIG. 1 with the guide arm in a second position, adjacent a portion of the spine.

As shown in FIG. 9, the guide member 16 is then advanced into the incision via rotation of the guide arm 14. The guide member is advanced antero-medially along the arcuate path until the insertion tip 113 is at the lateral margin of the targeted disc, at a target location. The target location is at a known position relative to the reference location provided by the distal end 32 of the targeting post 12, as the guide bar 14 holds the guide member 16 in a fixed relationship as the guide bar 14 rotates about the rotation post 50. At this point the guide arm and guide member are in a second position. The guide member 16 may have a rounded insertion tip, or a sharp, pointed insertion tip if necessary to penetrate the tissues. EMG monitoring may be used to ensure safe passage of the guide member through the fascia. The optional pinhole opening 102 creates access for a wire to pass through the guide arm into the guide member 16 if it is desirable to connect an electrode to the guide member 16 for nerve monitoring. The stop feature 52 (seen in FIG. 2) stops rotation of the guide arm 14 and prevents the guide member 16 from extending past the margin of the disc and contacting the spinal cord. The penetrating guide member 16 may vary in length and radius of curvature, to accommodate differing patient proportions and differing specific target locations. Accordingly, the guide arm 14 may be adjustable in length, to function correctly with the guide member to reach the target location.

Once the guide member 16 is correctly positioned adjacent the targeted location, the guide arm 14 is detached from the guide member 16 and the targeting post 12. The guide member 16 is left in the patient to serve as a guide for one cannula or series of cannulas which are graduated in size, and which are inserted sequentially from smaller to larger to increase the cross-sectional area of the access portal to the area to be treated.

Figure 10:
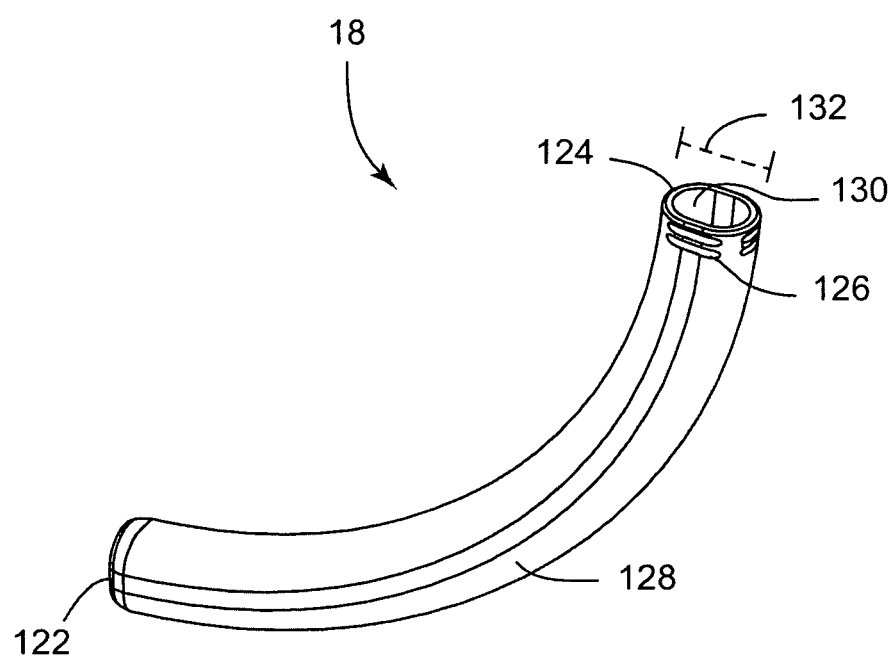
FIG. 10 is a perspective view of a cannula.

Referring to FIG. 10, a single cannula 18 is shown. The cannula 18 is longitudinally curved and generally tubular in form, with a tubular support wall 128 which has an open distal end 122 and an open proximal end 124. The distal end 122 is rounded so that tissues are pushed aside gently as the cannula is inserted through the patient. A bore 130 runs the length of the cannula 18 from the open distal end 122 to the open proximal end 124, and provides access to the targeted spinal area for instrument insertion, and insertion and removal of interbody devices, arthroscopic devices, implants, bone graft materials, bone cement, and other materials and devices. A cross-sectional shape of the support wall 128 of the bore 130 is generally curved, and may specifically be round, oval, elliptical or another curved shape. The cross-sectional shape has a width 132, which may have a maximum measurement of about 27 millimeters. The open proximal end 124 has a plurality of grip features 126 which allow the surgeon to grip the cannula. Optionally, the cannula 18 may have attachment features to allow attachment of the cannula to the instrument support arm. The cannula 18 may optionally be substantially radiolucent, and can comprise biocompatible polymers, elastomers, ceramics, or aluminum or other metals. The longitudinal curve of the cannula 18 may be arcuate, and may sweep through an angle of about 90° such that the open proximal and distal ends 124, 122 are substantially perpendicular to each other. A radius of curvature of the cannula may be constant along the entire cannula, and may range from about 2 to about 9 inches.

Figure 11:
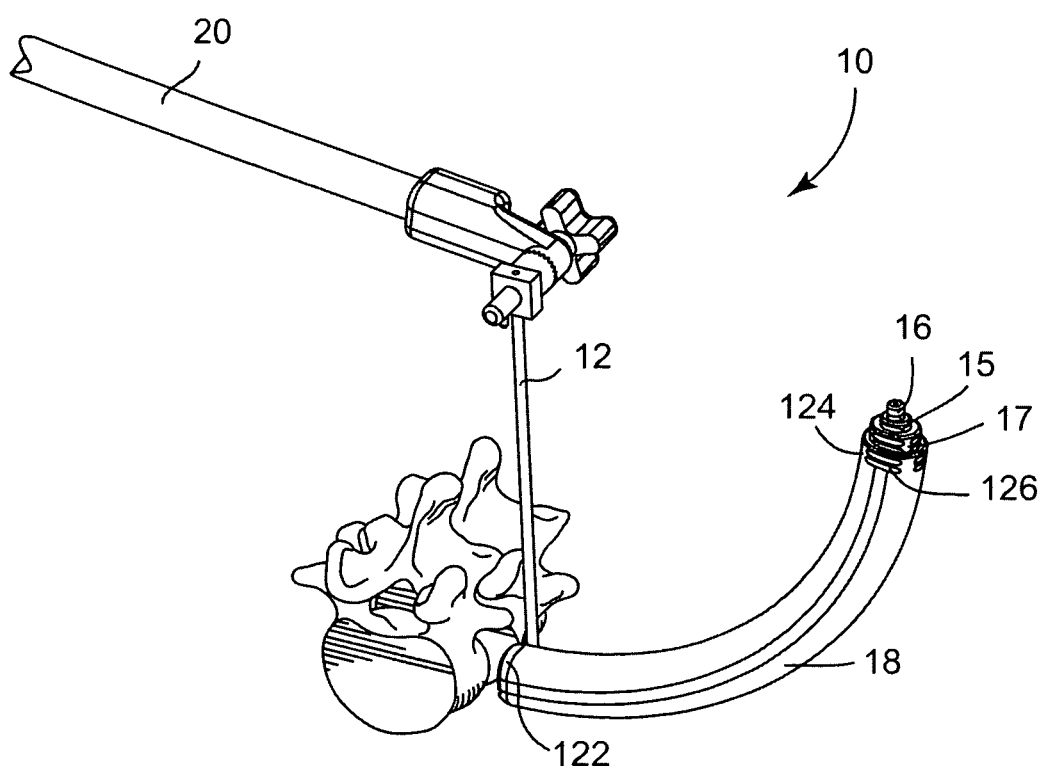
FIG. 11 is a perspective view of the arcuate cannula assembly of FIG. 1 with the guide arm removed and several cannulas added, adjacent a portion of the spine.

Referring to FIG. 11, a series of graduated cannulas 15, 17, 18 are inserted one at a time over the proximal end 110 of the penetrating guide member 16, and advanced antero-medially over the guide member 16 until the corresponding distal end reaches the distal end 112 of the guide member 16. Each cannula 17, 18 may be shorter in length and larger in cross-sectional area than the next smallest cannula, to allow the surgeon to grip each cannula as it is installed and removed. As each cannula 15, 17, 18 is inserted, the access portal through the soft tissues and fascia is increased in size, creating increased access to the targeted portion of the spine. The number of cannulas inserted is determined by the desired cross-sectional area of the opening to the spine; in many instances two to five cannulas will be inserted. Once all cannulas 15, 17, 18 are inserted around the penetrating guide member 16, the guide member 16 and the inner cannulas 15, 17 are removed, leaving the largest cannula 18 in the patient. This cannula may be attached via an attachment feature (not shown) to the support arm 20, to provide additional stabilization for removal of the smaller cannulas, and for subsequent instrument insertion and procedures. In the embodiment depicted, the penetrating guide member and all cannulas sweep through an angle of about 90°. It is appreciated that in alternate embodiments, the penetrating guide member and all cannulas may sweep through an angle from at least 45° to 135°.

In one embodiment of the invention, the largest cannula 18 may have a tooth portion (not shown) which extends longitudinally from the insertion end 122. During insertion, the tooth portion is placed between the superior and inferior endplates of the intervertebral space, to assist in maintaining distraction and access to the space. In an alternative embodiment, the largest cannula 18 may have one or more protruding pins or other elements extending from the insertion end 122 which can penetrate the superior and/or inferior vertebral bodies to provide additional stability to the cannula 18.

Figure 12:
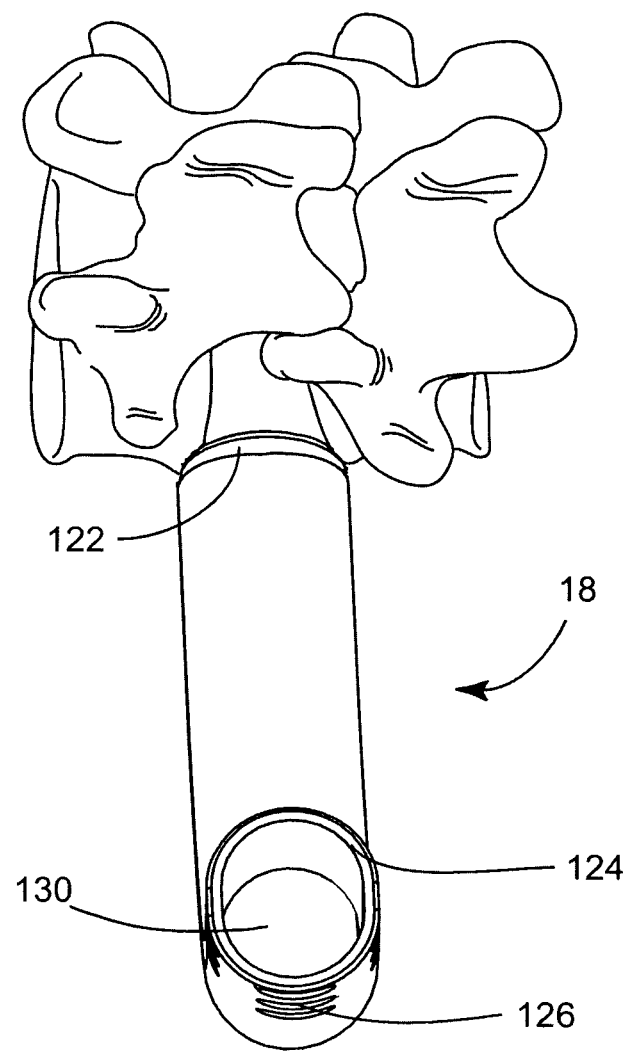
FIG. 12 is a postero-medial perspective view of the cannula of FIG. 10 adjacent a portion of the spine.

FIG. 12 is a postero-lateral view of a portion of a spine with a cannula inserted according to the procedure previously described. When in place in the patient, the bore 130 of the cannula 18 is an access portal through which surgical instruments, implants and other materials may be passed to complete a variety of intervertebral procedures. Surgical instruments used in conjunction with the cannula 18 may have rigid, curved shafts or flexible shafts to navigate through the cannula 18 to the intervertebral space. The cannula 18 may be sized to accommodate passage of an interbody fusion implant or other implant (not shown in FIG. 12).

Figure 13:
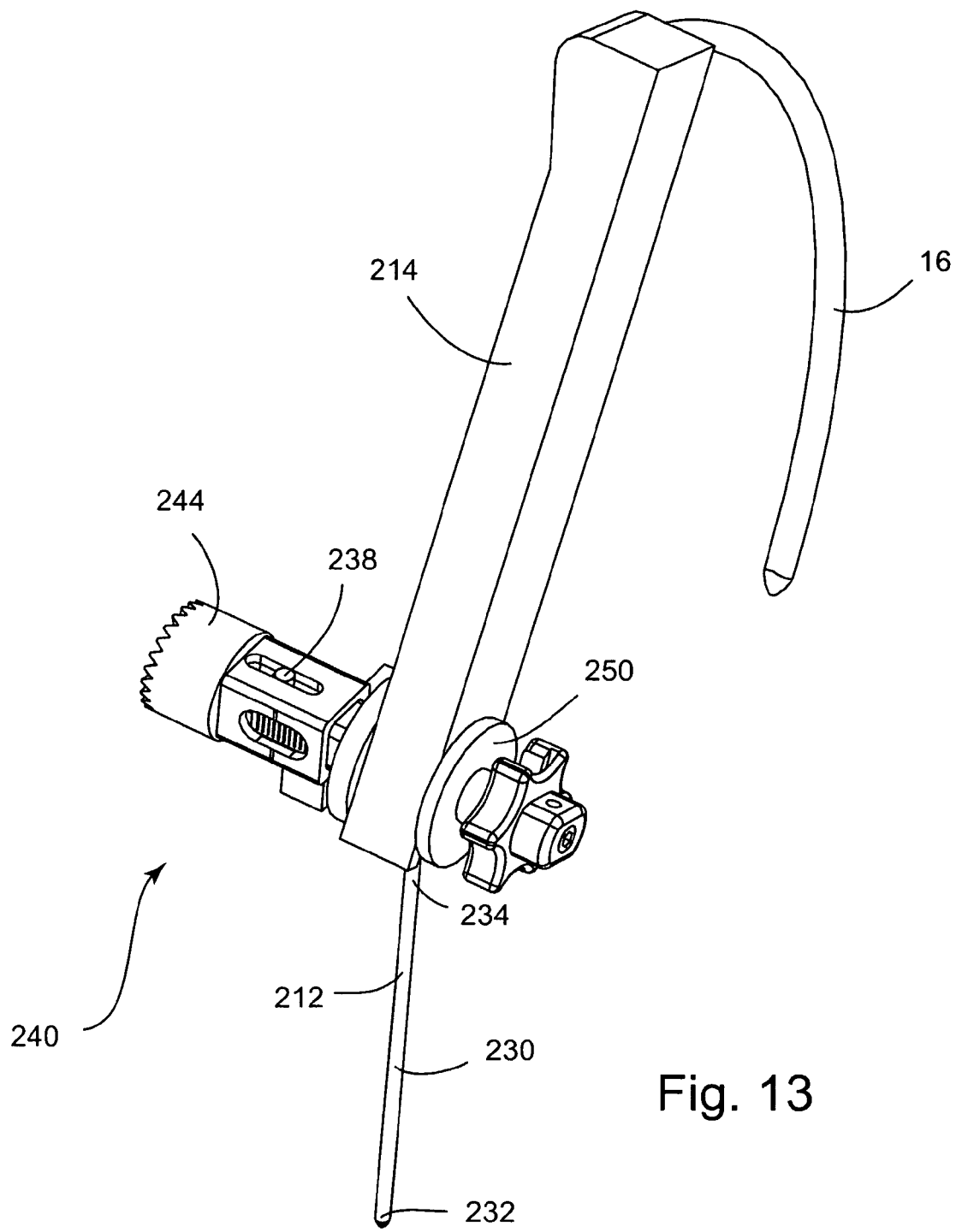
FIG. 13 is a perspective view of an arcuate cannula assembly with an adjustable targeting post.

Another embodiment of the invention comprises a targeting post which is capable of cephalad-caudal adjustment. FIG. 13 is a perspective view of an arcuate cannula assembly 210 which includes an adjustable targeting post 212, a guide arm 214 and a penetrating guide member 16. The adjustable targeting post 212 has a shaft 230 which has a distal end 232 and a proximal end 234. Proximally adjacent to the proximal end 234 of the shaft 230 is a connection portion 240, which extends in a cephalad-caudal direction and comprises a guide arm connector 250, a cephalad-caudal adjustment feature 238, and a support arm attachment post 244. The cephalad-caudal adjustment feature 238 can be adjusted to lengthen or shorten the cephalad-caudal length of the connection portion 240. Thus, after the targeting post is inserted into the patient, the length of the connection portion 240 can be adjusted as necessary to attain the necessary offset to adjust the resultant cephalad-caudal distance between the guide member 16 and the targeting post 212. The adjustment allows the target location to vary along the cephalad-caudal direction such that the known position of the target location is offset relative to the reference location. Cephalad-caudal offset of the guide arm 214 and the attached guide member 16 may be useful in avoidance of nerve structures and other objects during the dilation process.

Figure 14:
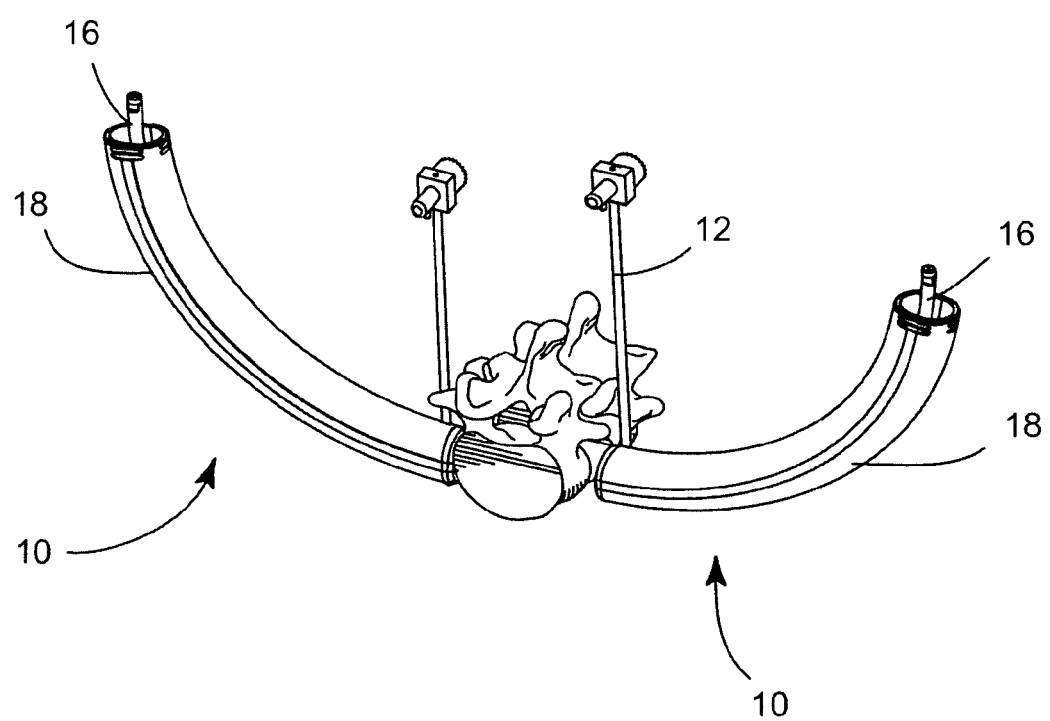
FIG. 14 is a perspective view of two arcuate cannula assemblies of FIG. 1, adjacent two lateral sides of a portion of the spine.

Another application of the invention comprises a bilateral implementation of two arcuate cannula assemblies. In this embodiment, two assemblies 10 are used together, one on each lateral side of the spine. Referring to FIG. 14, portions of two assemblies 10, which comprise two targeting posts 12, two penetrating guide members 16, and two cannulas 18, are shown adjacent to each lateral side of the spine. This embodiment permits enhanced access to the targeted area, since access may be attained from both lateral sides simultaneously. Instruments, implants, or other materials may be pushed or pulled into the intervertebral space, or through the entire access pathway.

Figure 15A:
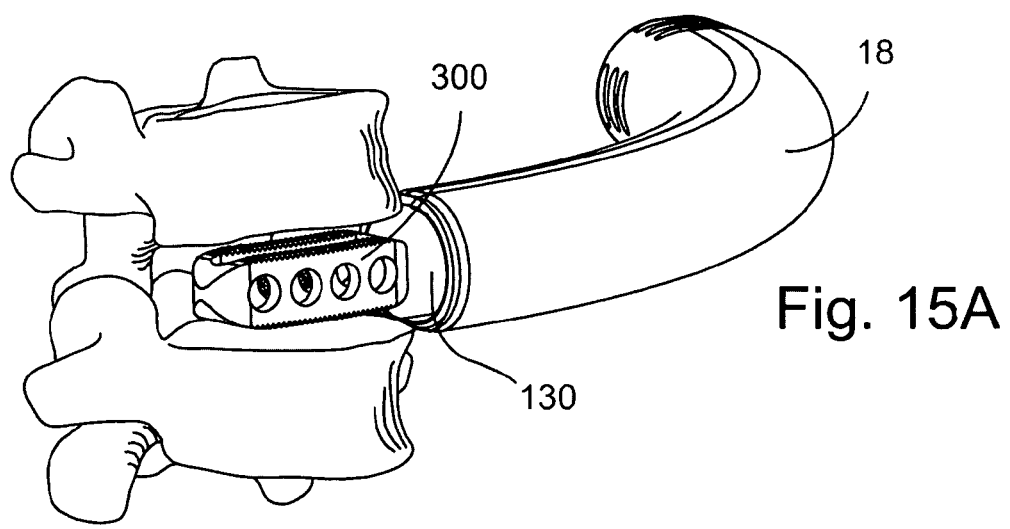
FIG. 15A is an antero-medial perspective view of the cannula of FIG. 10 adjacent a portion of a spine, and an interbody device in an intervertebral space.
Figure 15B:
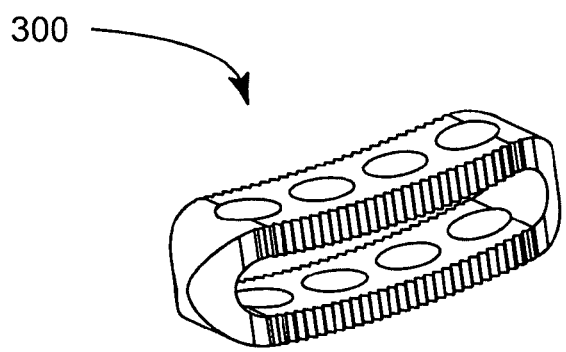
FIG. 15B is a perspective view of the interbody device of FIG. 15A.

Another embodiment of the invention further comprises an implant, which may be an interbody device. FIG. 15A is an anterior perspective view of first and second vertebrae with a cannula 18 and an interbody device 300 which may be inserted through the arcuate cannula assembly previously disclosed. An implant retaining inserter with a curved shaft (not shown) may be used to move the implant along the arcuate pathway of the cannula, then release the implant in the interbody space between the vertebrae. FIG. 15B is a perspective view of the interbody device 300 of FIG. 15A. The interbody device 300 has a generally rectangular box-like shape, and is slightly curved along its longitudinal axis. The interbody device 300 may optionally have a radius of curvature substantially the same as that of the cannula 18.

Other implants (not shown) may be shaped to be implantable through the cannula in the manner set forth previously and illustrated in FIG. 15A. These implants may include, but are not limited to, a nucleus replacement, an annulus replacement, a staple, a lateral plate, a lateral plate-interbody implant combined device, an artificial disc, a therapeutic-containing implant, a vertebral body screw, a vertebral body anchor, and a facet replacement.

In any case, the bore 130 of the cannula 18 is sized to accommodate passage of the interbody device 300. Because use of the arcuate cannula assembly 10 allows improved access to the intervertebral space, the interbody device 300 may have a larger footprint than many other interbody devices, and can extend across most of the medial-lateral width of the intervertebral space, to provide for increased stability, increased bone in-growth, and improved fusion. A curved insertion tool and curved tamp (not shown) are used to insert and seat the interbody device 300 in the intervertebral space. In the alternative, a flexible insertion tool and/or a flexible tamp may be used.

A set of curved spinal orthopedic instruments may be used in conjunction with the arcuate cannula assembly set forth previously to complete spinal procedures. These instruments are set forth below and in FIGS. 17-27, and may include rasps, curettes, rongeurs, wedge distractors, trial implants, tamps, probes and implant insertion devices, among others. Each instrument may have a gripping portion, and a working portion which comprises a shaft and a specific tool portion, or working end. The shaft may be an arcuate shaft which extends along an arcuate shaft pathway that matches the pathway along which the corresponding cannula extends. The working end of each instrument is sized to pass through the arcuate cannula 18, and may be coupled to the arcuate shaft such that the working end follows the same trajectory as the arcuate shaft; thus the entire working portion may be continuously curving along the arcuate shaft pathway. The radius of curvature of the arcuate shaft pathway may substantially equal the radius of curvature of the arcuate cannula 18. Thus configured, the working portion of each instrument may be inserted through the arcuate cannula, allowing the working end to protrude out of the distal end of the cannula to reach the location of the spinal procedure.

Figure 16:
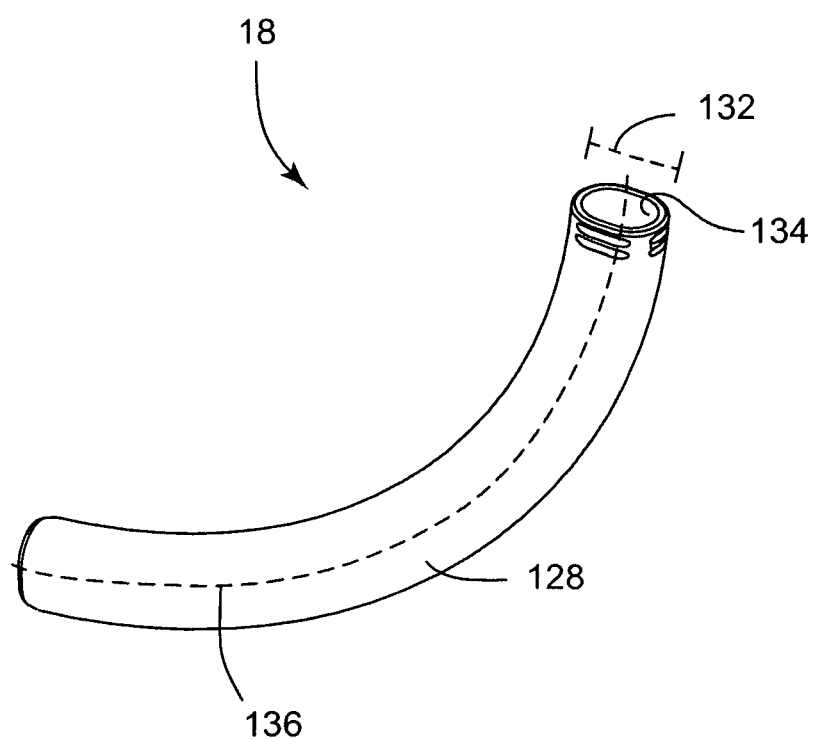
FIG. 16 is a perspective view of the cannula of FIG. 10, showing the boundaries of an arcuate envelope.

Referring to FIG. 16, a perspective view of the cannula 18 is shown. The cannula 18 is curved, and, as embodied in FIG. 16, is also arcuate. Thus, the cannula 18 defines an arcuate envelope through which an instrument may pass. The cannula 18 (and thus the arcuate envelope) extends longitudinally along an arcuate envelope pathway 136, which may have a radius ranging from about 2 inches to about 12 inches. More precisely, the arcuate envelope pathway may have a radius ranging from about 4 inches to about 9 inches. Still more precisely, the arcuate envelope pathway may have a radius of about 5.5 inches. The support wall 128 which forms the cannula has an interior surface 134. As mentioned previously, the interior surface 134 defines the arcuate envelope. The arcuate envelope, and thus the cannula 18, extends longitudinally along the arcuate envelope pathway 136, and may sweep through an arc ranging from about 45° to about 135°. More precisely, the cannula 18 may sweep through an arc ranging from about 60° to about 120°. Yet more precisely, the cannula 18 may sweep through an arc ranging from about 75° to about 105°. Still more precisely, the cannula 18 may sweep through an arc of about 90°.

The cannula 18 (and hence the corresponding envelope) has a substantially uniform cross-sectional shape, which may be circular, ovoid, elliptical or any other uniform, closed shape. A "substantially uniform cross-sectional shape" is possessed by an "extrusion," i.e., a body that extends along a pathway with substantially the same cross-sectional shape and size (taken perpendicular to the pathway) at any location along the length of the pathway. The maximum width of the arcuate envelope, defined as a straight line across the largest dimension of the cross-section taken at right angles to the arcuate envelope pathway 136, may range from about 5 millimeters to about 50 millimeters. More precisely, the maximum width may range from about 15 millimeters to about 40 millimeters. Yet more precisely, the maximum width may range from about 20 millimeters to about 30 millimeters. Still more precisely, the maximum width of the arcuate envelope may be about 27 millimeters. The arcuate shaft and working end of each instrument are configured and coupled together such that they may pass through the arcuate envelope and the working end may extend out of the envelope.

Figure 17:
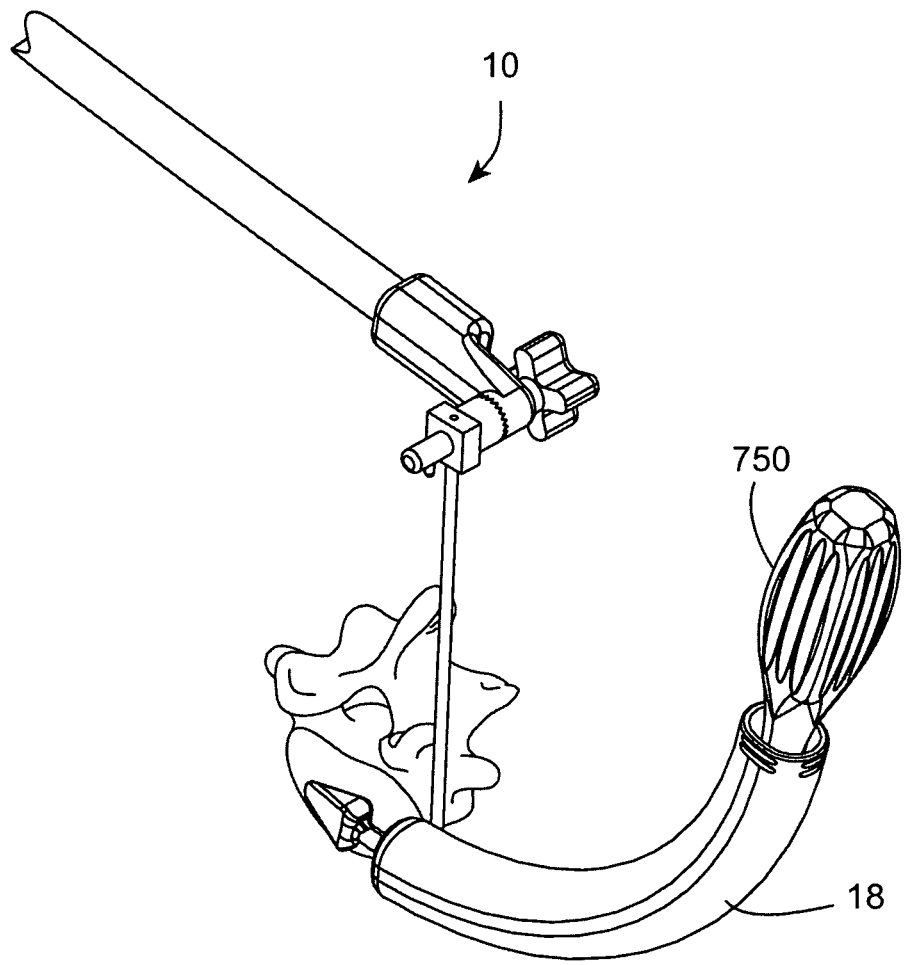
FIG. 17 is a perspective view of an arcuate cannula assembly with a curved wedge distractor instrument inserted into a cannula, adjacent a portion of the spine.

In FIG. 17, an instrument with a curved shaft is inserted through the arcuate cannula 18 of the arcuate cannula assembly 10 to reach the location of a spinal procedure. One vertebra is shown to provide perspective; a second is omitted so that a working end of the instrument may be seen. Wedge distractor 750, similar to wedge distractor 700 described below but with a different wedge head, is inserted through cannula 18 to reach the intervertebral space. A working portion of the wedge distractor 750 comprises a working end, in this case the wedge head, and a shaft that couples the working head to a handle. The arcuate shaft is may be curved, and may indeed be curved along a constant radius to provide an arcuate shaft that passes through the arcuate envelope defined by the interior surface of the arcuate cannula 18.

Figure 18:
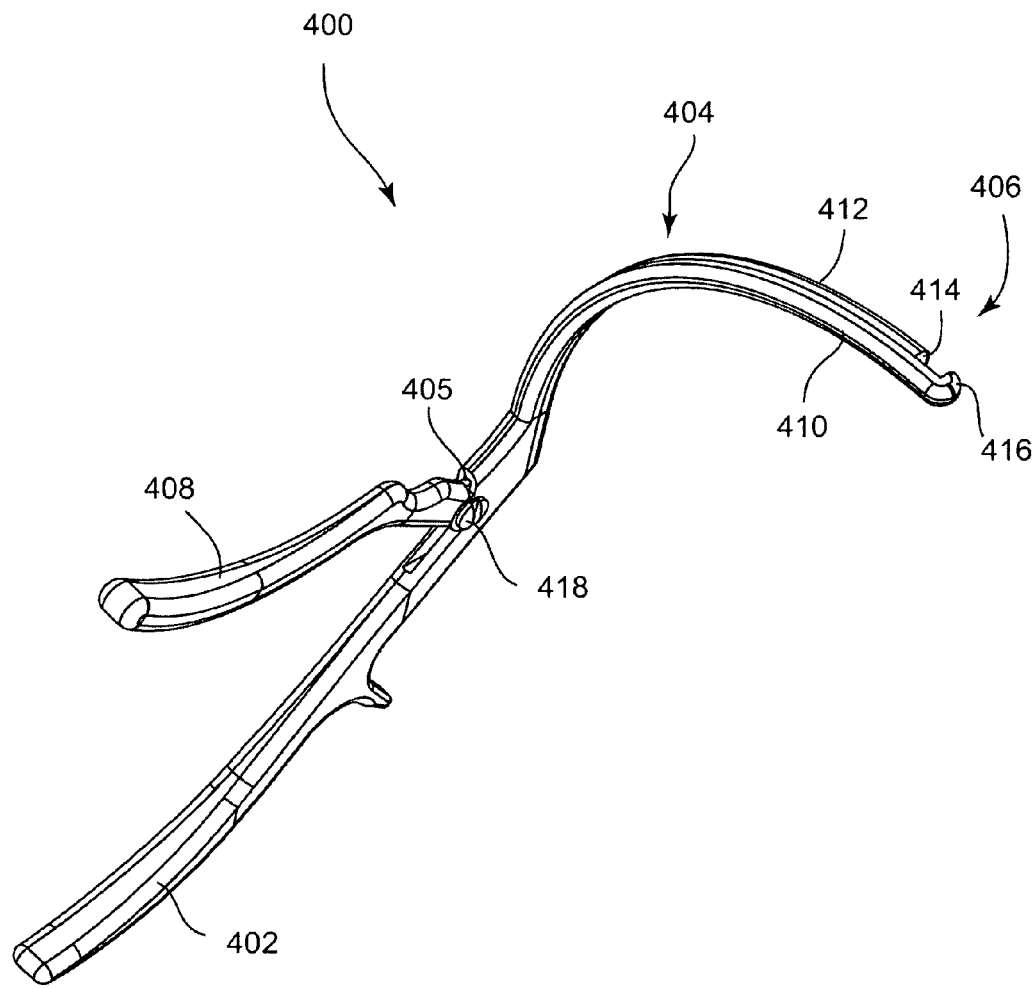
FIG. 18 is a perspective view of a curved rongeur.

Referring to FIG. 18, a perspective view of a curved rongeur 400 is shown. The curved rongeur 400 has a gripping portion 402 with an adjacent lever 408, and a working portion consisting of a curved shaft 404 and a working end in the form of a nipping mechanism 406. Coupled to the gripping portion 402 is the proximal end of the curved shaft 404 which extends along an arcuate shaft pathway. Coupled to the distal end of the arcuate shaft 404 is the nipping mechanism 406. The curved shaft 404 has two longitudinally oriented arcuate elements, a shank 410 and a crossbar 412. The shank 410 extends from the gripping portion, and terminates distally at a stop 416. The crossbar 412 is connected to the lever 408 by a link 405. A pivot 418 connects the lever 408 to the gripping portion 402, such than as the lever 408 is actuated, the lever 408 rotates about the pivot 418 and the linked crossbar 412 slides along the shank 410. The nipping mechanism 406 comprises a distal end 414 of the crossbar 412, and the stop 416. When the lever 408 is fully actuated, the crossbar 412 slides along the shank 410 until the distal end 414 of the crossbar 412 meets the stop 416.

During a surgical procedure, the curved rongeur 400 may be inserted through an arcuate cannula such as the arcuate cannula 18 of FIG. 16, and the nipping mechanism 406 may be employed through manipulation of the gripping portion 402 and lever 408 to grasp and relocate pieces of bone, cartilage, intervertebral disc tissues, or other tissues or materials. The curved shaft 404 is narrow and long enough that the nipping mechanism 406 can reach a variety of locations at the targeted area, such as in an interbody space between two vertebrae.

Figure 19:
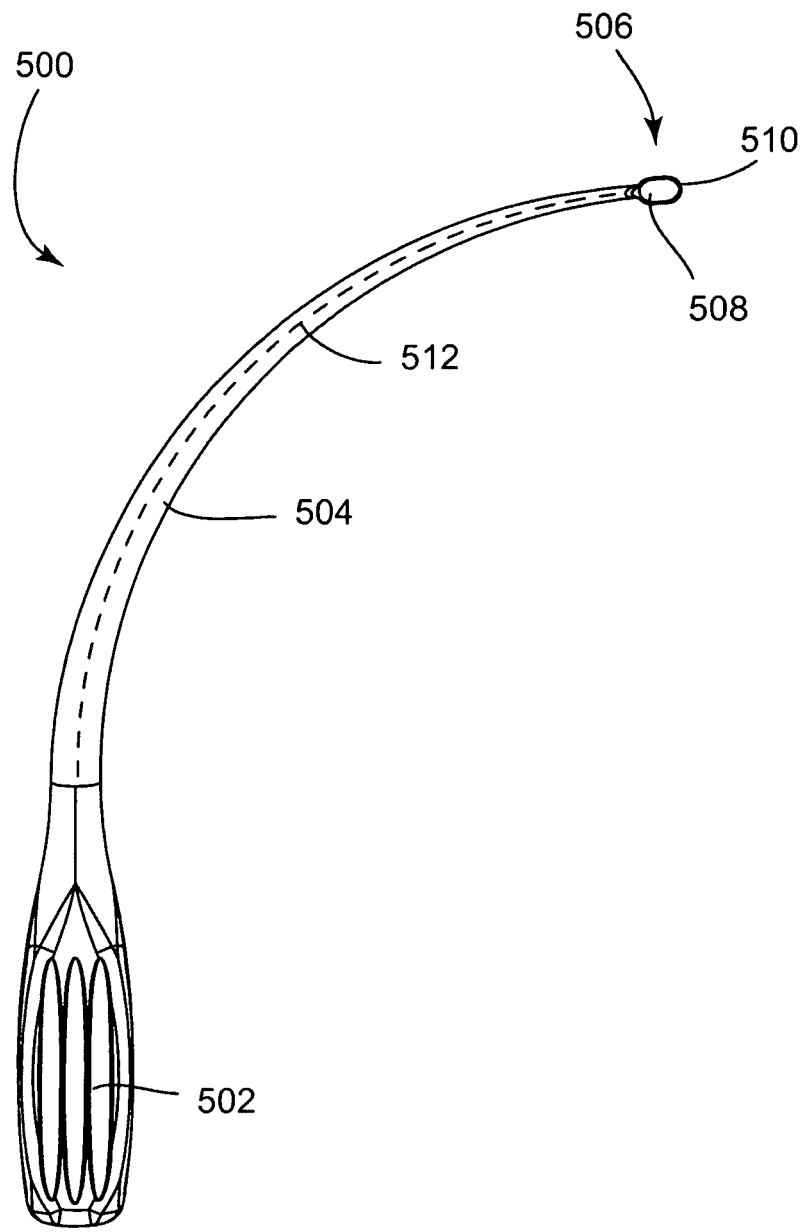
FIG. 19 is a perspective view of a curved curette.

Referring to FIG. 19, a perspective view of one embodiment of a curved curette 500 is shown. The curved curette 500 has a gripping portion 502 to which is coupled an arcuate shaft 504 which extends along an arcuate shaft pathway 512. The arcuate shaft pathway 512 may have a radius ranging from about 2 inches to about 12 inches. More precisely, the arcuate shaft pathway 512 may have a radius ranging from about 4 inches to about 9 inches. Still more precisely, the arcuate shaft pathway 512 may have a radius of about 5.5 inches. The curvature of the arcuate shaft pathway 512 may match the curvature of the arcuate envelope pathway 136 (shown in FIG. 16). These dimensions may be applied to any instrument or to any cannula disclosed herein.

Coupled to the distal end of the arcuate shaft 504 is a working end which is a cutting head 506. Cutting head 506 is spoon-shaped, with a cup 508 and a blade 510 forming the rim of the cup. The cutting head 506 may be disposed at a variety of orientations and angles relative to the arcuate shaft 504. In FIG. 19, the cutting head 506 is aligned with the curve of the arcuate shaft 504, and the cup 508 opens upward when the curette 500 is held in a horizontal position as depicted.

Figure 20A:
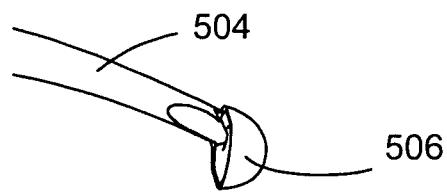
FIG. 20A is a perspective view of a curette head in an upward-opening, angled position.
Figure 20B:
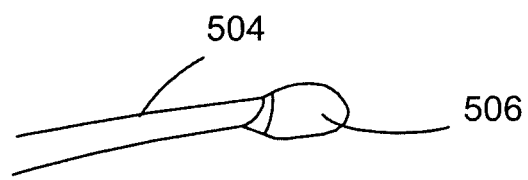
FIG. 20B is a perspective view of a curette head in an downward-opening position.
Figure 20C:
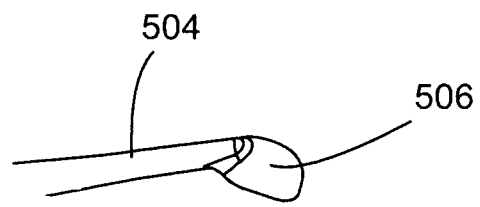
FIG. 20C is a perspective view of a curette head in an downward-opening, angled position.

FIGS. 20A-20C display some of the possible other orientations of the cutting head, which allow the cutting head to reach different areas in the intervertebral space. Each orientation may still allow the cutting head to pass through the arcuate cannula; the cutting head may be small enough that even when oriented at an angle, it still fits within the arcuate envelope defined by the cannula 18. In FIG. 20A, the cutting head 506 opens upward relative to the arcuate shaft 504 and is disposed at an angle to the longitudinal axis of the shaft. In FIG. 20B, the cutting head 506 is aligned with the arcuate shaft 504, and opens downward. In FIG. 20C, the cutting head 506 opens downward and is disposed at an angle to the arcuate shaft 504, but still fits within the arcuate envelope defined by the interior surface of the cannula 18. This variety of orientations allows a surgeon to choose the curette configuration best suited for the particular task at hand. These figures represent only some of the orientations at which the cutting head 506 may be disposed; it is appreciated that many other configurations and orientations are possible and are within the scope of the disclosure.

Figure 21:
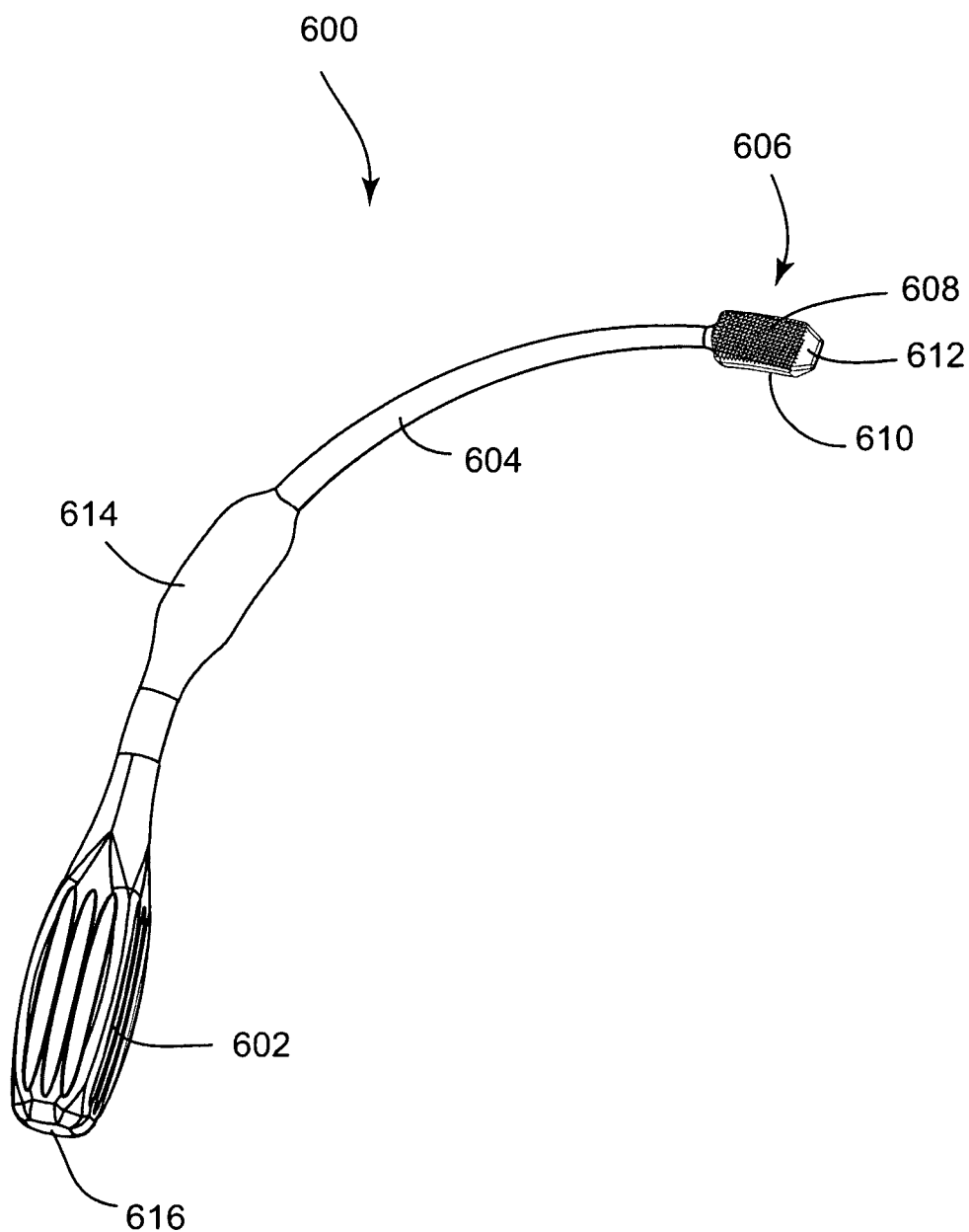
FIG. 21 is a perspective view of a curved wedge rasp.

Referring to FIG. 21, a perspective view of one embodiment of a curved wedge rasp 600 is shown. The curved wedge rasp 600 has a gripping portion 602, an arcuate shaft 604, and a working end which is a rasp head 606, coupled to the distal end of the arcuate shaft 604. The arcuate shaft 604 follows an arcuate shaft pathway similar to the arcuate shaft pathway 512 of the curved curette 500. The arcuate shaft 604 and rasp head 606 make up a working portion which is sized and oriented to fit through an arcuate cannula such as the cannula 18 in the manner set forth previously and depicted in FIG. 17. The rasp head 606 is generally rectangular in shape but curves slightly, following the arcuate envelope pathway 136 (shown in FIG. 16). Alternatively, such a rasp may have a conventional straight rasp head 606 in combination with a curved shaft.

A first toothed rasp surface 608 occupies one long side of the rasp head 606, while a second toothed rasp surface 610 is on the opposite side. A wedge 612 is at the distal terminus of the head 606, allowing the surgeon to pry into and distract the targeted area and then rasp the distracted surfaces. Various dimensions of the rasp head may vary, including the length, height and width of the rasp head 606, size of rasp teeth, and length of the wedge 612, among others. The height of the rasp head may be sized to match the height of an implant, so that the rasp prepares a correctly sized area for insertion of the implant. A stabilization feature 614 is a wide portion of the arcuate shaft 604 and is configured to fit just inside the arcuate cannula 18 to stabilizes the position of the rasp 600 as force is applied to the handle 602. The gripping portion 602 has a reinforced impaction surface 616 at its proximal end to facilitate striking of the gripping portion 602 with an object such as a mallet.

Figure 22:
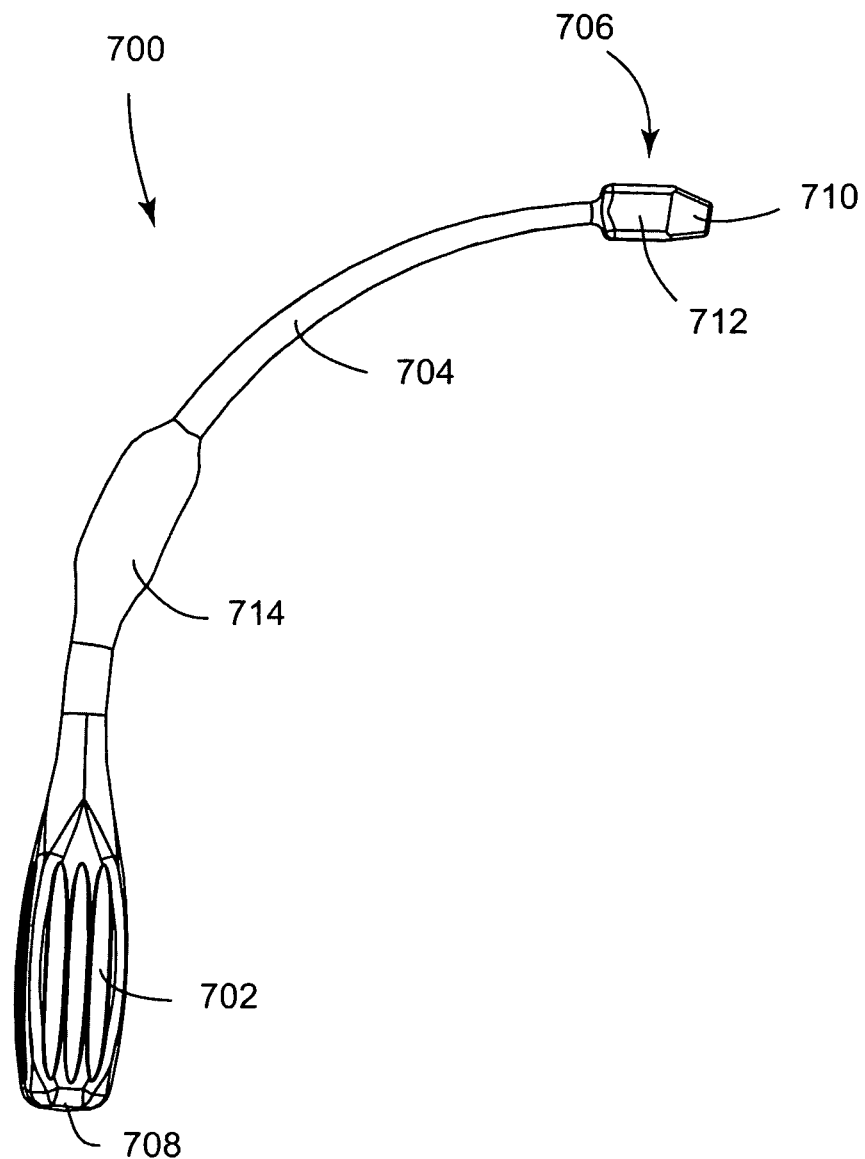
FIG. 22 is a perspective view of a curved wedge distractor.

Referring to FIG. 22, a perspective view of a curved wedge distractor 700 is presented. The curved wedge distractor 700 has a gripping portion 702, an arcuate shaft 704, and a working end which is a wedge head 706, coupled to the distal end of the arcuate shaft 704. The arcuate shaft 704 follows an arcuate shaft pathway similar to the arcuate shaft pathway 512 of the curved curette 500. At the proximate end of the gripping portion 702 is an impaction surface 708. During a distraction procedure, a mallet or other striking instrument may be used to apply force to the curved wedge distractor 700, and the impaction surface 708 is an area reinforced to withstand the blows and translate the force distally toward the wedge head 706. The wedge head 706 has a wedge-shaped peaked portion 710, and a wider rectangular block portion 712. As force is applied to the wedge distractor 700, the smaller peaked portion 710 first enters the interbody space, gradually wedging it apart; the block portion 712 that follows maintains the distraction. A stabilization feature 714 is a wide portion of the arcuate shaft 704 which is configured to fit just inside the arcuate cannula 18 (not shown). The stabilization feature 714 allows the wedge head 706 to enter the interbody space on a precisely defined path, and stabilizes the position of the entire distractor 700 as force is applied to the impaction surface 708.

It is appreciated that the wedge head 706 may be configured in a variety of ways. For example, the wedge distractor 750 in FIG. 17 has a wedge head which has no block portion. Alternatively, the wedge head may vary in the angle of the wedge, width or length of the wedge portion, width, height or length of the block portion, ratio of wedge portion to block portion, and number of sides, among other dimensions. A series of wedge distractors with wedge heads of graduated sizes may be used to sequentially distract the interbody space. The height of a wedge distractor head chosen for a procedure may match the height of an implant used in the same procedure.

Figure 23:
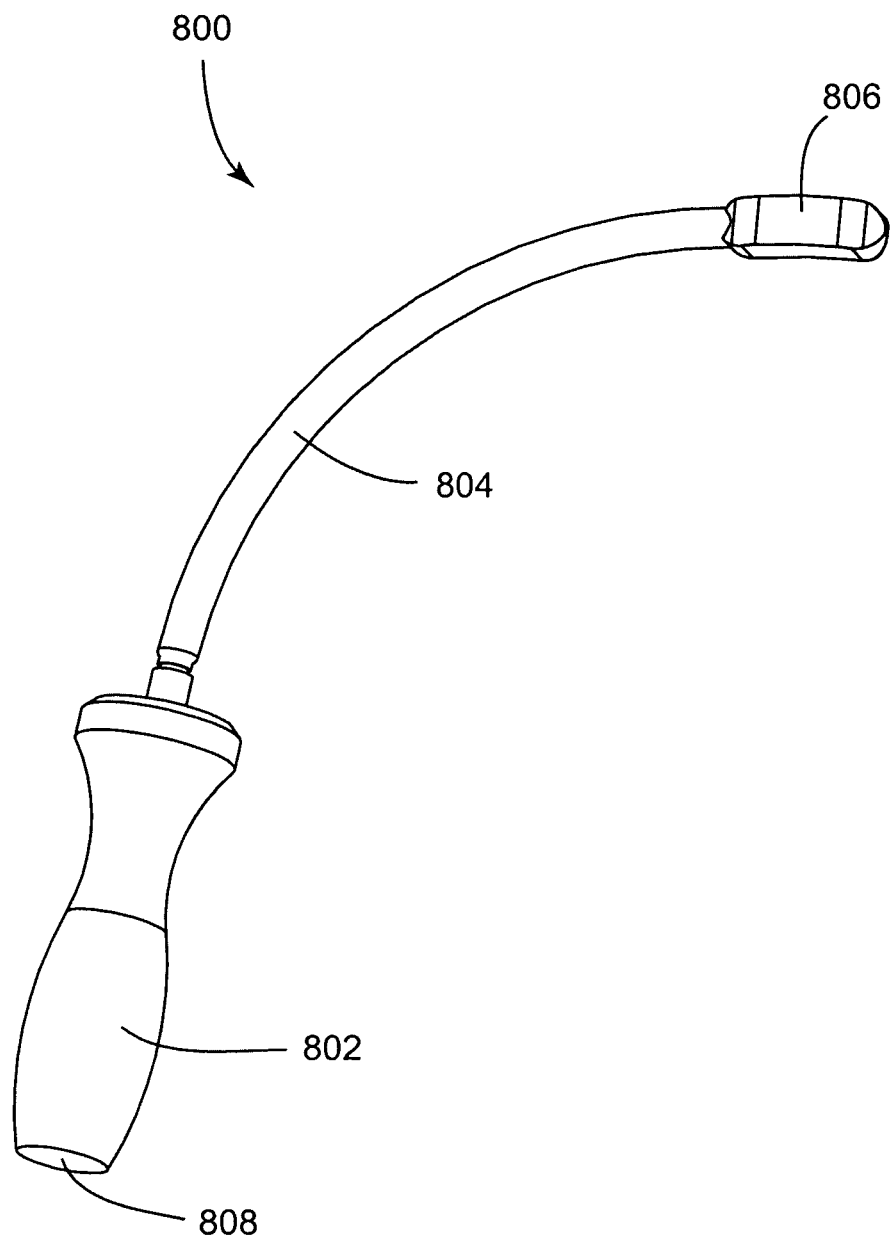
FIG. 23 is a perspective view of a curved trial implant instrument.

Referring to FIG. 23, a perspective view of a trial implant instrument 800 is shown. The trial implant instrument 800 has a gripping portion 802 and a working portion comprising an arcuate shaft 804 and a working end. The arcuate shaft 804 follows an arcuate shaft pathway similar to the arcuate shaft pathway 512 of the curved curette 500. At the proximal end of the gripping portion 802 is an impaction surface 808, which is reinforced to withstand force from a mallet or other striking instrument. At the distal terminus of the arcuate shaft 804 is the working end, which is a trial implant 806. The trial implant 806 is curved along the same trajectory as the arcuate shaft 804. The trial implant 806 may be permanently coupled to the distal end of the shaft 804, or may be releasably attached, allowing for substitution of alternate trial implants. It is appreciated that a variety of trial implants (or, if the trial implant 806 is not detachable from the arcuate shaft 804, a variety of trial implant instruments) that vary in function, shape and/or size may be provided to allow practitioners to insert and remove several trial implants in order to determine and select the properly configured implant for final implantation.

Figure 24:
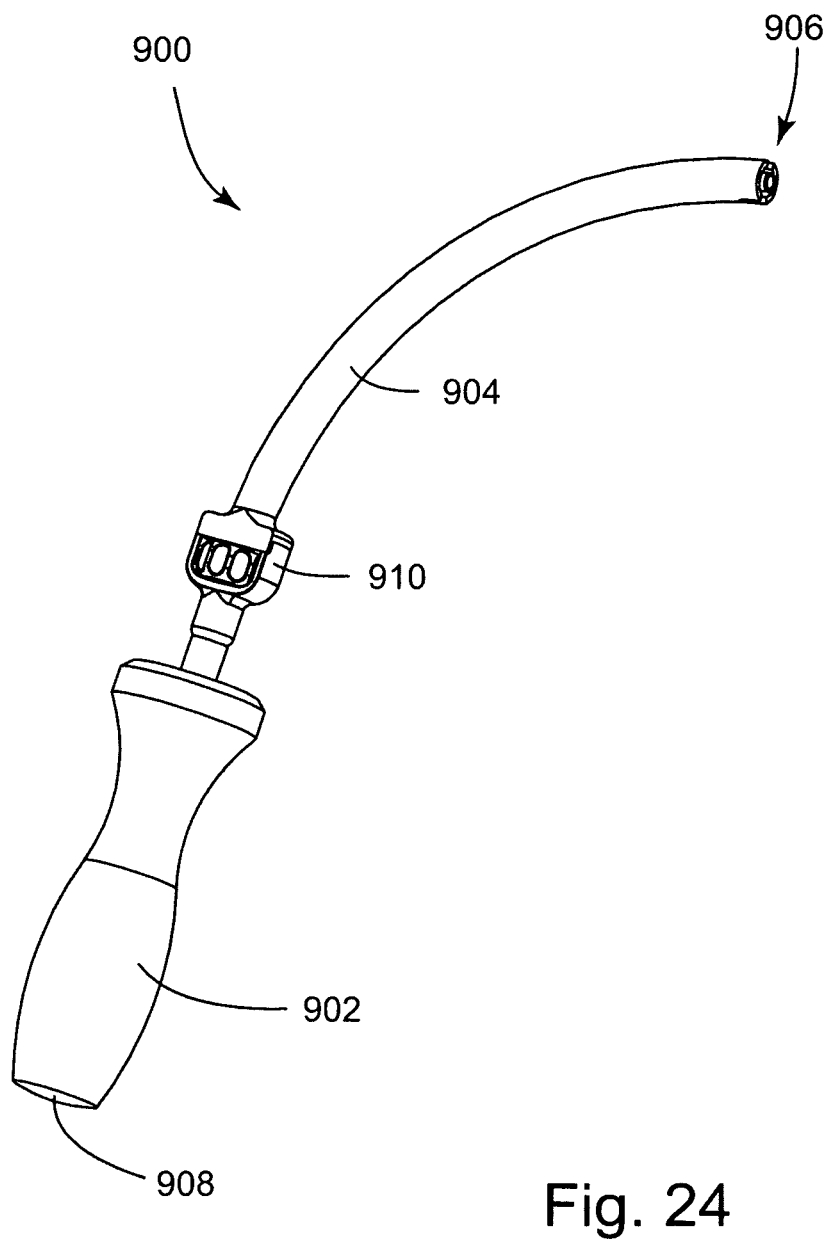
FIG. 24 is a perspective view of a curved implant inserter.

Referring to FIG. 24, a perspective view of an implant inserter 900 is shown. The implant inserter 900 has a gripping portion 902 and an arcuate shaft 904. The arcuate shaft 904 follows an arcuate shaft pathway similar to the arcuate shaft pathway 512 of the curved curette 500. Coupled to the distal end of the arcuate shaft 904 is a working end which is an implant connector 906. An implant retaining mechanism 910 is located on the arcuate shaft 904; on other embodiments of the invention it may be located on the gripping portion 902. The implant retaining mechanism 910 is linked to the implant connector 906 through the arcuate shaft 904, and allows for controlled retention and release of a spinal implant such as the interbody implant 300 of FIGS. 15A and 15B. The implant retaining mechanism 910 may be sized to fit within the arcuate envelope defined by an arcuate cannula such as the cannula 18. An impaction surface 908, which is reinforced to withstand force from a mallet or other striking instrument, may be located at the proximal end of the gripping portion 902.

Figure 25:
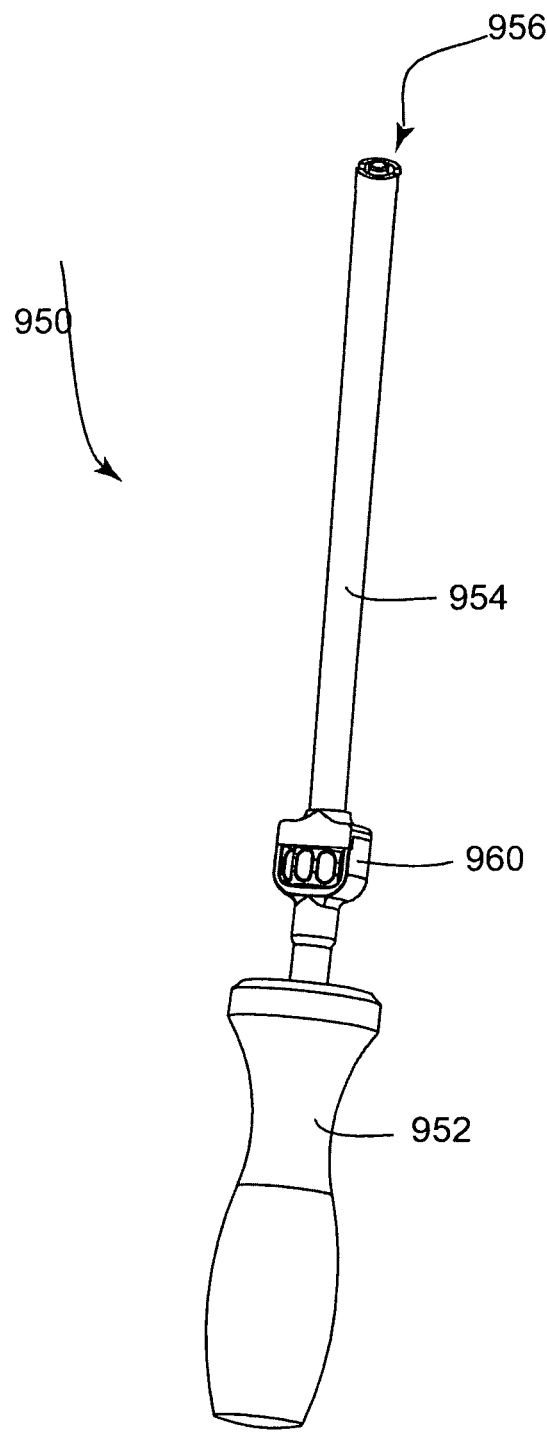
FIG. 25 is a perspective view of an implant inserter with a flexible shaft.

A flexible implant inserter with a flexible shaft is shown in FIG. 25. Flexible implant inserter 950 has a gripping portion 952 and a flexible shaft 954. The flexible shaft 954 may have a straight position as depicted in FIG. 25, and may flex to attain a curved position. Coupled to the distal end of the flexible shaft 954 is a working end which is an implant connector 956. Similar to the implant inserter 900, flexible implant inserter 950 has an implant retaining mechanism 960 which is linked to the implant connector 906. A spinal implant such as the interbody implant 300 of FIGS. 15A and 15B may be connected to the implant connector 956; then the implant 300 and the flexible shaft 954 may be inserted through the cannula 18 of FIG. 16. As the flexible shaft 954 moves through the cannula 18, it can flex to match the curvature of the cannula 18, and thus, the curvature of the arcuate envelope pathway 136. After the implant 300 is positioned in the interbody space, it is released via actuation of the implant retaining mechanism 910, and the flexible implant inserter 950 is withdrawn from the cannula 18.

Figure 26:
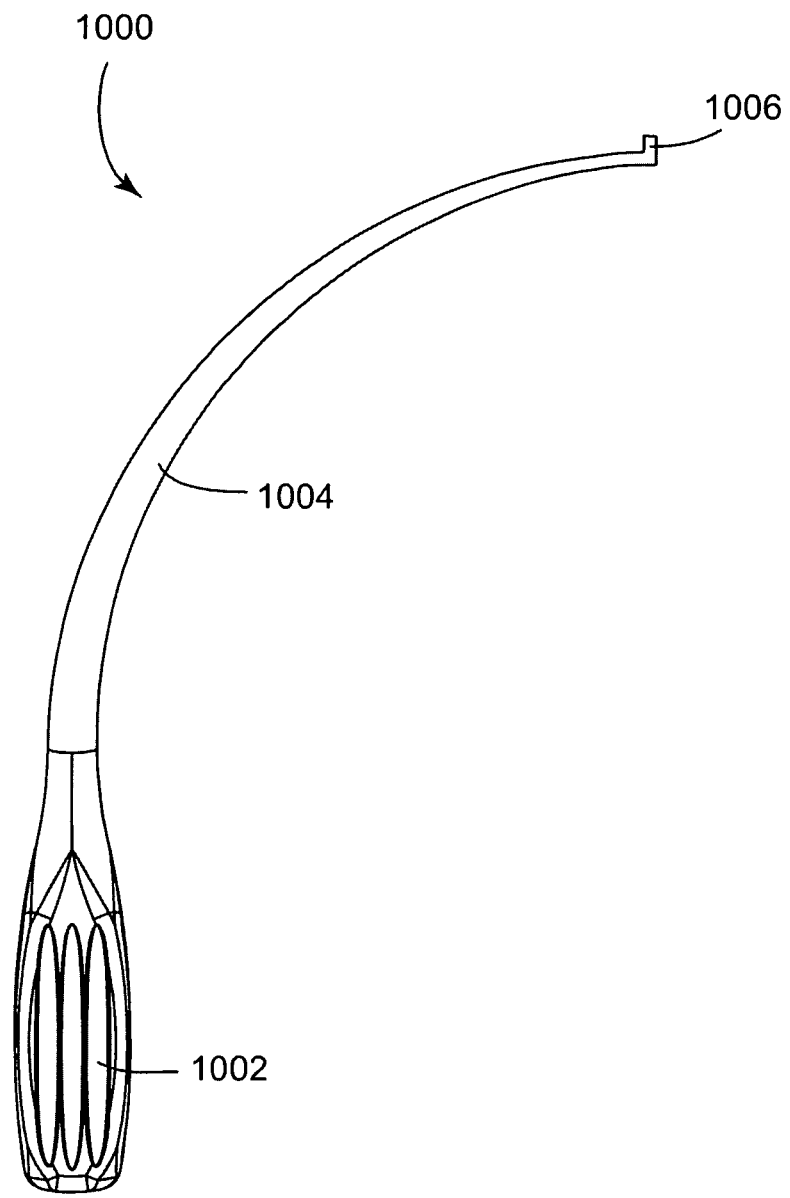
FIG. 26 is a perspective view of a curved probe.

Referring to FIG. 26, a perspective view of a curved probe 1000 is shown. The curved probe 1000 has a gripping portion 1002 and an arcuate shaft 1004 which follows an arcuate shaft pathway similar to the arcuate shaft pathway 512 of the curved curette 500. Extending perpendicularly from the distal end of the arcuate shaft 1004 is a working end which is a probe tip 1006. The arcuate shaft 1004 and probe tip 1006 may be inserted through the arcuate cannula 18 (not shown) to probe and test the spinal surgical site during a spinal surgical procedure to locate anatomy or carry out other functions. Shown in FIG. 26 is a probe tip 1006 which extends anteriorly when used with the arcuate cannula assembly 10; however the probe tip 1006 may be configured to extend posteriorly, laterally or in any direction from the distal end of the arcuate shaft 1004.

Figure 27:
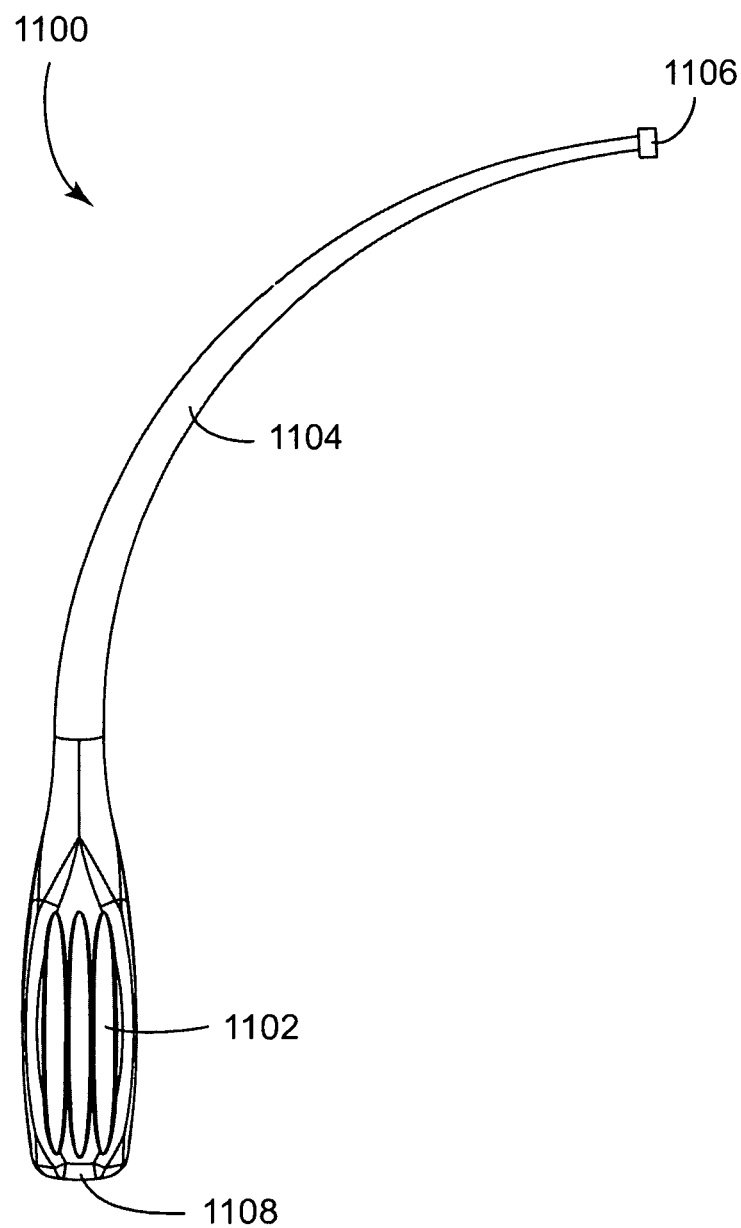
FIG. 27 is a perspective view of a curved tamp.

Referring to FIG. 27, a perspective view of a curved tamp 1100 is shown. The curved tamp 1100 has a gripping portion 1102 and an arcuate shaft 1104 which may follow an arcuate shaft pathway similar to the arcuate shaft pathway 512 of the curved curette 500. Coupled to the distal end of the arcuate shaft 1104 is a working end which is a tamp head 1106. After placement of the interbody implant 300 or other implant with the implant inserter 900, the curved tamp 1100 may be used through the cannula 18 to fine tune the placement of the implant. A reinforced impaction surface 1108 may be located on the proximal end of the gripping portion 1102.

Each of the instruments set forth above and depicted in FIGS. 17-27 is configured to be inserted through the arcuate cannula 18 in the manner depicted in FIG. 17. Except for the flexible implant inserter 950, the shaft of each instrument may be formed of a rigid material and in a rigid arcuate configuration. Alternatively the shaft of each instrument may be formed of a compliant material which can flex to attain an arcuate configuration and pass through the arcuate envelope defined by the arcuate cannula, similar to the flexible implant inserter 950. Such instruments formed with flexible shafts may also be used to reach through cannulas which are curved, but do not have a fixed radius of curvature.

The gripping portion of each instrument may be coupled to the shaft in the orientation depicted for each instrument in FIGS. 17-27. Alternatively, the gripping portion of any instrument may be coupled to the shaft so that the gripping portion is at an angle relative to the shaft. More precisely, the gripping portion may be oriented at an angle perpendicular to the proximal end of the shaft. In another embodiment, the gripping portion may be oriented such that a longitudinal axis of the gripping portion is parallel to a longitudinal axis of the working end. In such an orientation, a motion at the gripping portion of the instrument may translate to an equivalent motion at the working end, giving enhanced tactile control to the user of the instrument.

To perform a particular spinal procedure, one or more of the curved instruments set forth above may be inserted through the arcuate cannula to access the spinal surgical site.

For example, to perform an interbody device implantation between two vertebrae, a first instrument such as the curved curette 500, curved rasp 600 or curved rongeur 400 is inserted into the arcuate cannula and its working end employed to prepare the intervertebral space and vertebral endplates. The instrument is removed and a second preparatory instrument, or more, from the same group may be inserted and used if necessary. When preparation of the intervertebral space and endplates is complete, a curved trial implant instrument 800 may be used to insert variously sized trial implants through the cannula to determine the correct size for an interbody implant. Finally, the interbody implant 300 is inserted through the cannula using the curved implant inserter 900, released and implanted in the interbody space. The curved tamp 1100 may then be used to adjust the positioning of the implanted implant 300.

Figure 28:
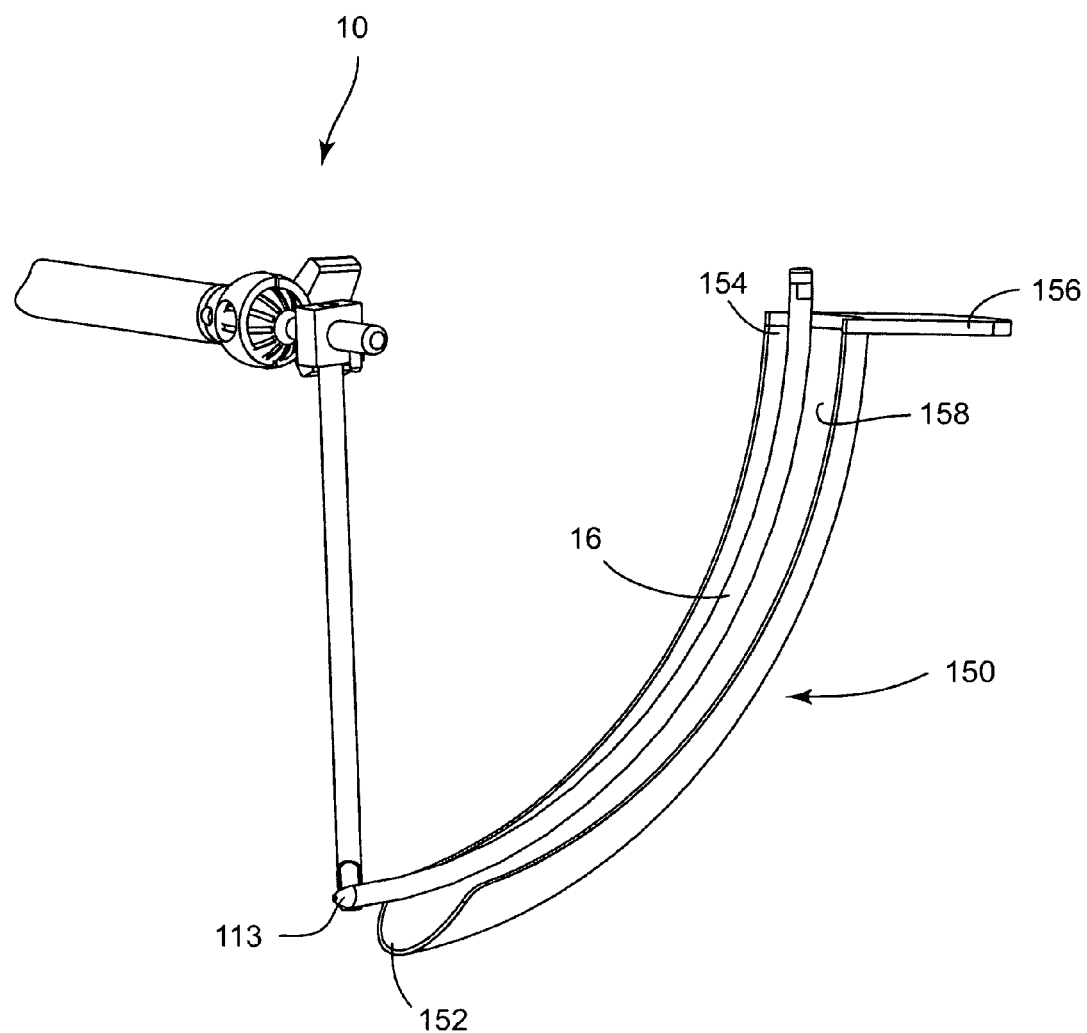
FIG. 28 is a perspective view of an arcuate cannula assembly and a peritoneal retractor.

An alternative embodiment of the invention is shown in FIG. 28. A peritoneal retractor 150 may be used with the arcuate cannula assembly 10 to retract and protect the tissues surrounding the path of the associated cannula 18 or dilator. The peritoneal retractor 150 has a curved half-pipe configuration, with a rounded distal end 152 and a proximal end 154. A flat lip 156 extends perpendicularly from the proximal end 154, and can be used to grip and guide the peritoneal retractor 150. The peritoneal retractor 150 is curved longitudinally to match the curve of the guide member 16, the cannula 18, and any intermediate cannulas used to facilitate dilation of the opening through the tissues. A curved guiding surface 158 extends from the proximal end 154 to the distal end 152, to provide guidance for the guide member 16 and cannulas as they are introduced.

The peritoneal retractor 150 is introduced into the patient after a targeting post is introduced as set forth previously. After the surgeon has marked the incision location and made the incision, the surgeon may insert a finger into the incision to locate and palpate the soft tissues and fascia. Next, the peritoneal retractor 150 may be gradually inserted along the path of the finger to both shield and retain the tissues. The retractor 150 may be inserted until the rounded distal end 152 comes in contact with the psoas muscle, or the retractor may be inserted until the distal end reaches the spine. Once inserted, the proximal end 154 of the retractor may be moved laterally to permit visualization along the retractor. The guide member 16 is then advanced antero-medially along the arcuate path of the curved guiding surface 158 until the insertion tip 113 is at the lateral margin of the targeted disc, at a target location. The peritoneal retractor 150 remains in place as the series of graduated cannulas 15, 17, 18 of FIG. 11 are introduced over the guide member 16 as set forth previously; the retractor 150 may make insertion of the cannulas 15, 17, 18 easier by preventing the surrounding tissues from enveloping the guide member. After completion of the surgical procedure, the largest cannula 18 is removed, and finally the retractor 150 is removed after removal of the cannula 18.

Figure 29:
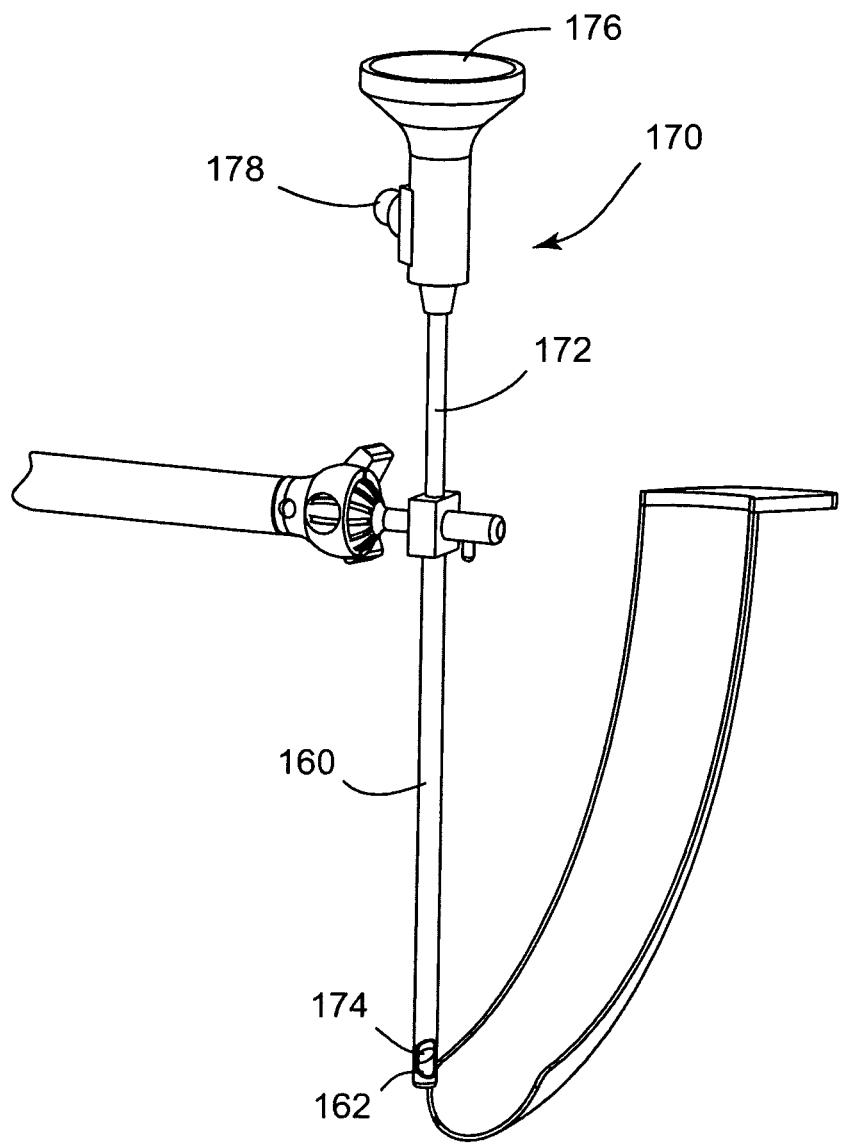
FIG. 29 is a perspective view of an arcuate cannula assembly and an endoscope.

Another embodiment of the invention includes a visualization component, such as an endoscope. Referring to FIG. 29, an endoscope 170 is used with the arcuate cannula assembly 10. The endoscope has a tube 172 which terminates distally with an aperture 174, and has a viewing portal 176 at a proximal end. A video connection 178 is located near the viewing portal 176. The endoscope is deployed by inserting the tube 172 through a hollow targeting post 160 with an opening 162 at its distal end. By looking through the viewing portal 176 or using the video connection 178 to a separate display screen, the surgeon can view the surgical procedure at the targeted location. A light source including fiber optics may be used to provide light to the location. Alternatively, the endoscope may include a flexible tube and/or be inserted through the arcuate cannula, or the targeting post.

Figure 30:
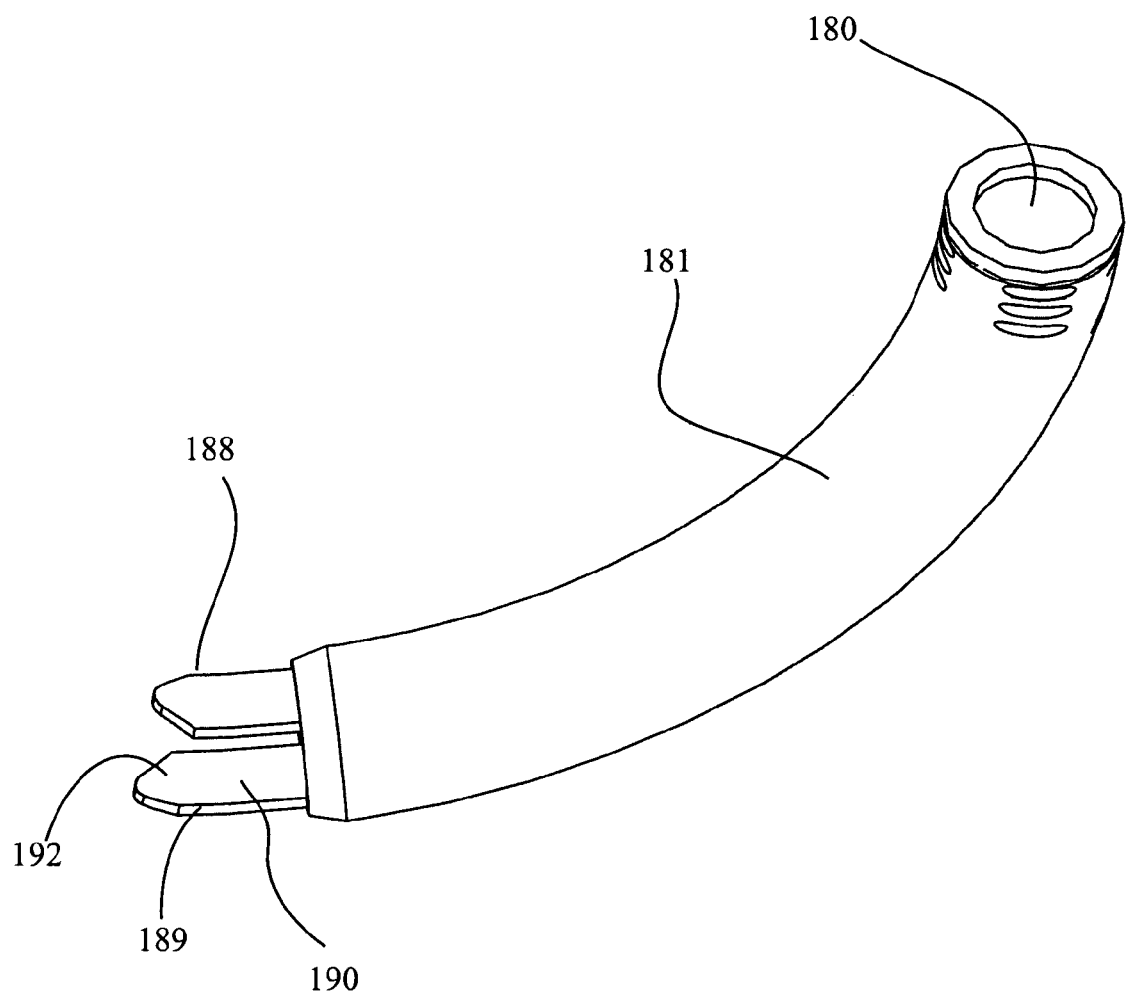
FIG. 30 is a perspective posterior view of a curved cannula with tang extensions inside a larger curved cannula.
Figure 31:
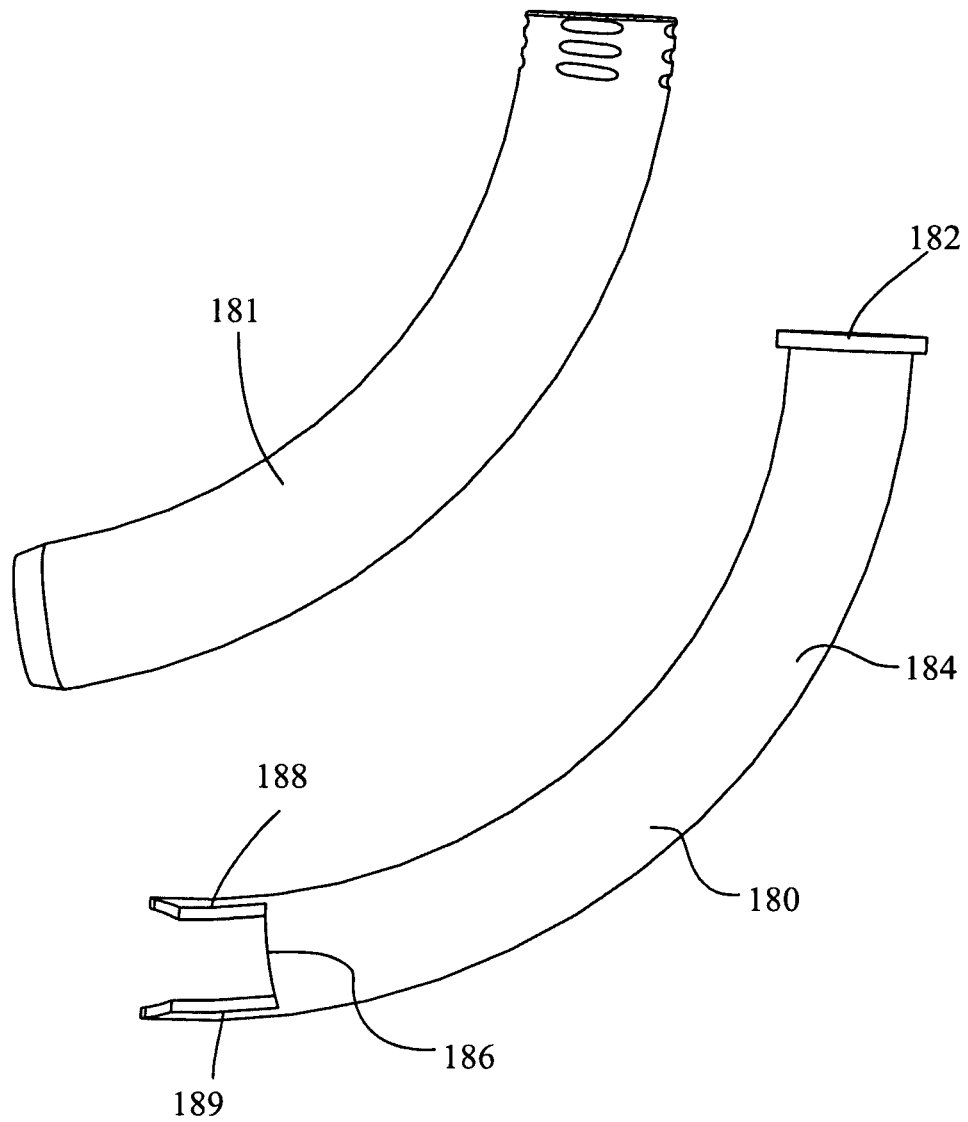
FIG. 31 is a posterior view of the cannulas of FIG. 30 placed side by side.

Referring to FIGS. 30-31, a tanged cannula insert 180 that has two pronged extensions is shown inside a slightly larger diameter cannula 181. Cannula insert 180 comprises a proximal end 182, an curved shaft 184 and a distal end 186. Extending distally from the distal end 186 are two tangs 188, 189. The tangs each may have curved body 190 with a tapered end 192. In an alternative embodiment, at least one of the tangs may comprise at least one flat portion. The tangs 188, 189 may be inserted through the cannula 181 into the intervertebral space between two adjacent vertebrae to securely dock the cannulae 180, 181 adjacent the intervertebral space, providing access for a surgical procedure to be performed within the interbody/disc space. The tangs 188, 189 may be located as illustrated in FIG. 30, so that upon insertion tang each tang spans a portion of the intervertebral space and has an edge oriented toward each vertebral body. In alternative embodiments, the tangs may be located such that each tang is facing one vertebral body upon insertion. The tapered ends 192 may allow the tangs 188, 189 to penetrate the disk annulus, if present. Insertion of the tanged cannula 180 through cannula 181 allows the tangs 188, 189 to reach the intervertebral space without catching on or otherwise encountering or damaging body tissues between the insertion point and the intervertebral space. Proximal end 182 may comprise a rim, lip or other feature which engages with the larger cannula 181 to limit how far the tanged cannula insert 180 may be inserted into the intervertebral space. The tanged cannula insert and other cannulas described herein may be arcuate, with a fixed radius of curvature. Tanged cannula insert 180 may be configured to be insertable into other cannulas described herein, such as cannula 18. Tanged cannulas with graduated sizes of tangs may be sequentially deployed.

The purpose of the tanged cannula insert may be four-fold: 1) docking the cannulas to the disc space, to ensure little to no movement of the cannulas throughout the surgical procedure; 2) maintaining the height of the disc space during subsequent procedures such as interbody implantation; 3) providing a working channel for the surgical procedures to be performed, and 4) protecting anterior and/or posterior vessels or structures as instruments are inserted into the intervertebral space, by blocking access to the vessels.

Figure 32:
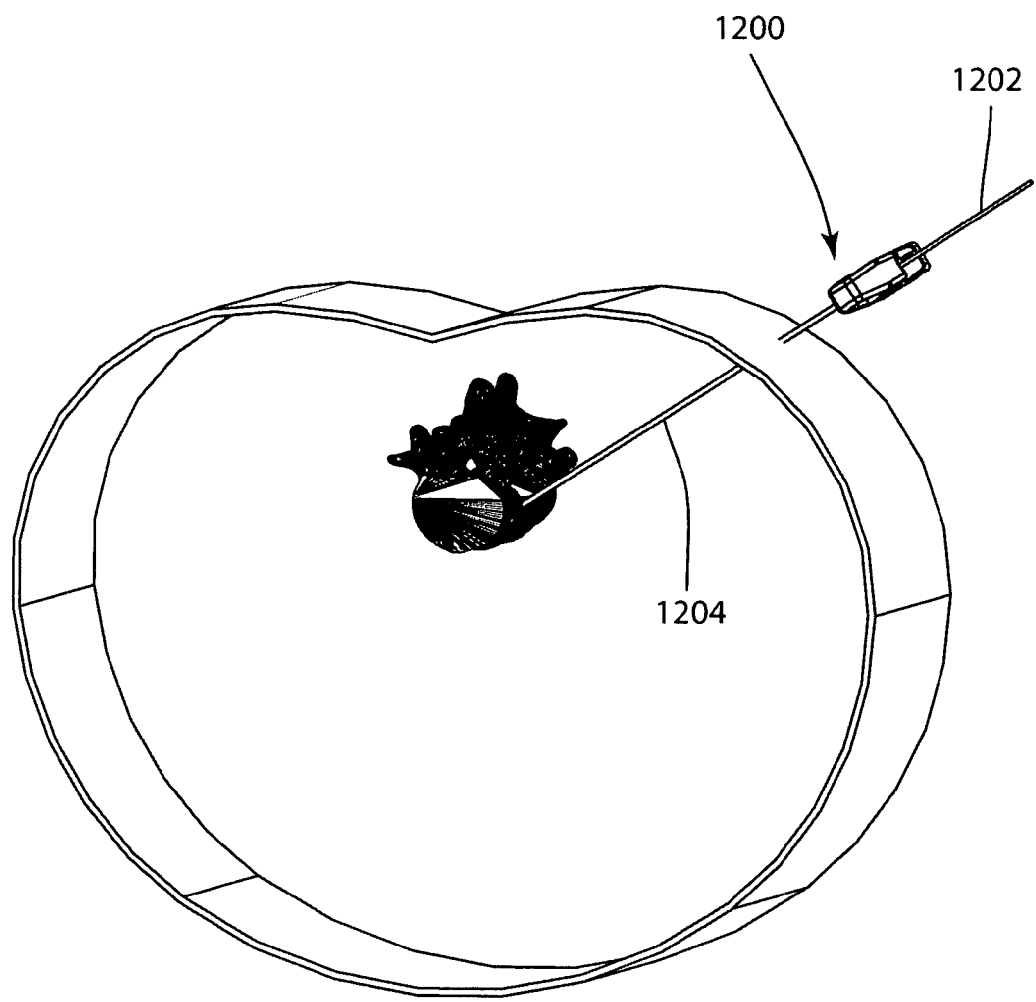
FIG. 32 is a stylized medial-posterior view of a portion of a torso and a spinal column, with a sheathed needle inserted to the spinal column from a lateral posterior approach.
Figure 33:
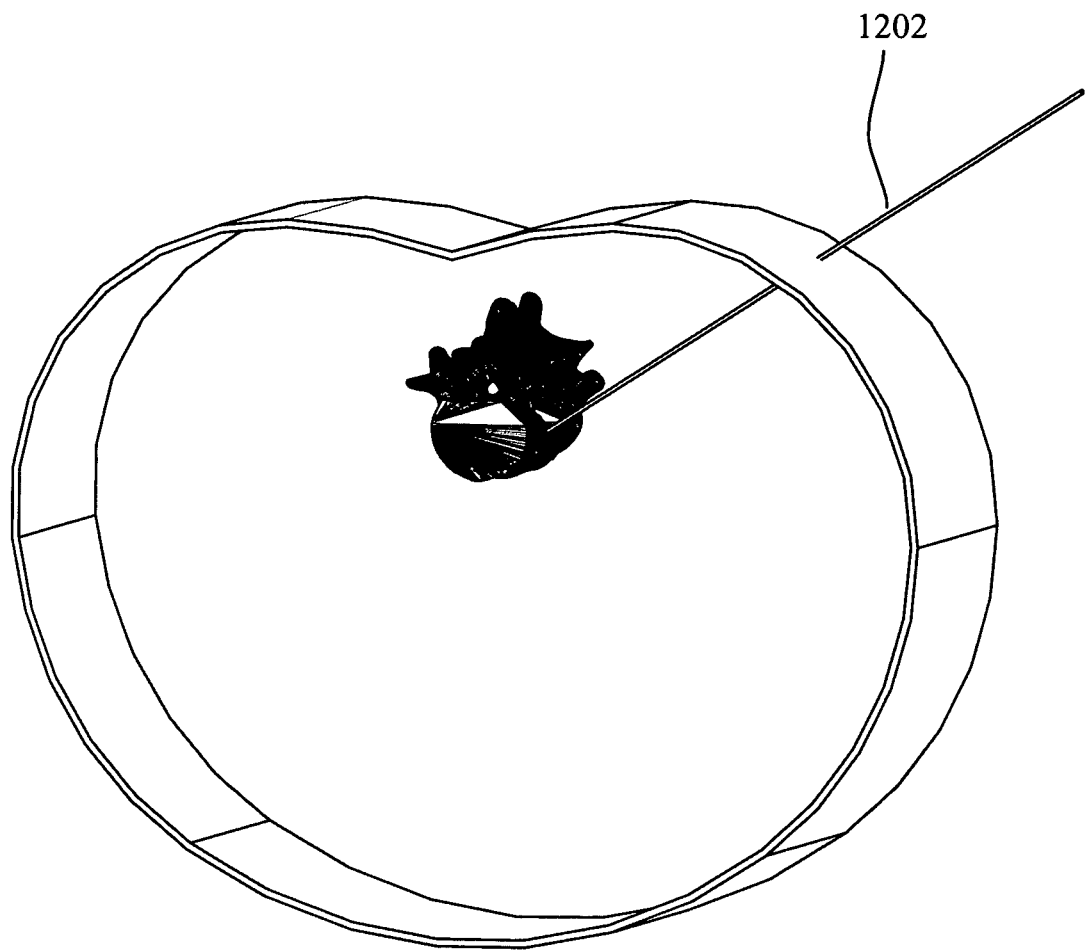
FIG. 33 is a stylized medial-posterior view of the portion of the torso and the spinal column, showing the needle of FIG. 32 with the sheath removed.
Figure 34:
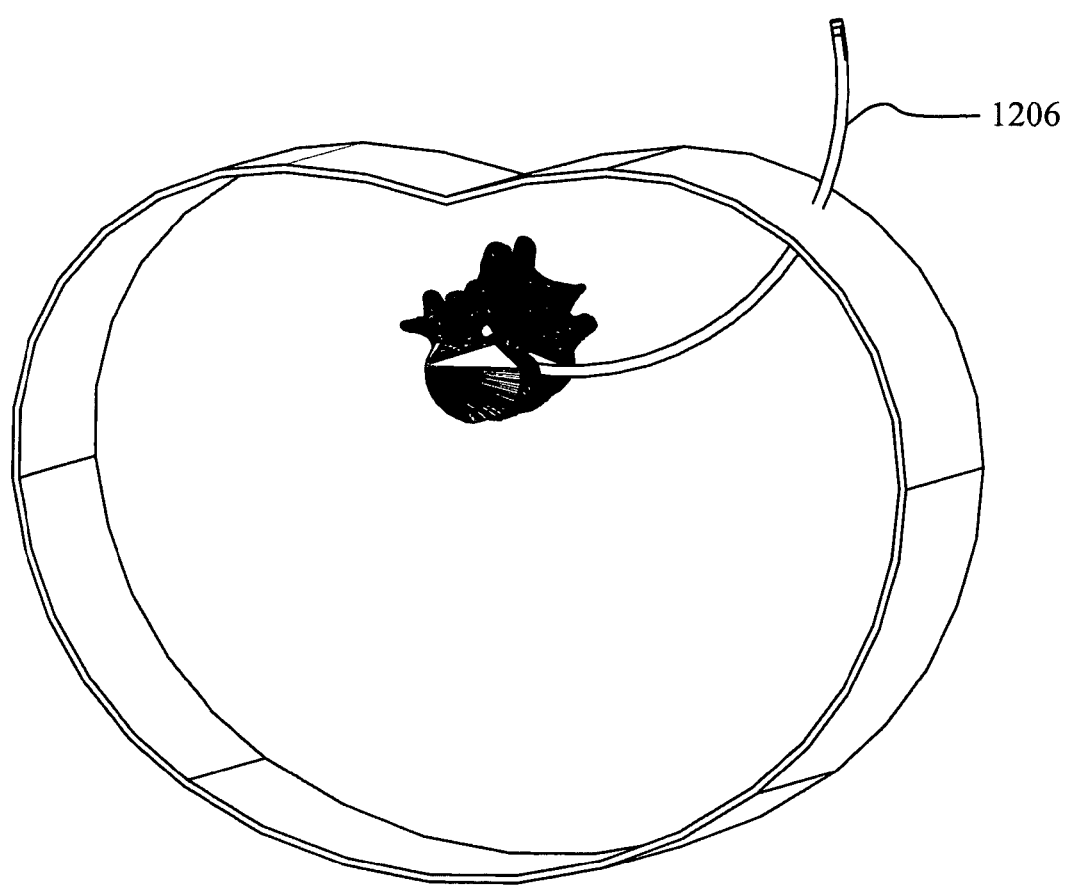
FIG. 34 is a stylized medial-posterior view of the portion of the torso and the spinal column, with a curved cannula placed over the needle of FIG. 33.

Referring to FIGS. 32-34, a system and method are disclosed that allow for lateral access to the disc space through a posterior approach. Illustrated in FIG. 32, a needle 1200 is introduced into the posterior portion of the back at a given distance off the midline on an oblique angle to be directed towards the disc space. The needle may comprise a flexible inner wire 1202, with a more rigid outer sheath 1204. The needle 1200 is continually introduced until the targeted disc space is penetrated. As seen in FIG. 33, the rigid outer sheath 1204 of the needle 1200 is then removed, leaving the more flexible inner wire 1202 with one end inside the disc space, and the other end outside of the skin. A curved rigid cannula 1206 may then be introduced over the flexible wire 1202 until the disc space is reached, as shown in FIG. 34. Larger cannulas (not shown) may then be introduced over the first curved rigid cannula 1206 to increase the accessibility to the disc space. The inner cannulas may be removed, and instruments may be inserted through the largest cannula to perform surgical procedures, as set forth previously.

Figure 35:
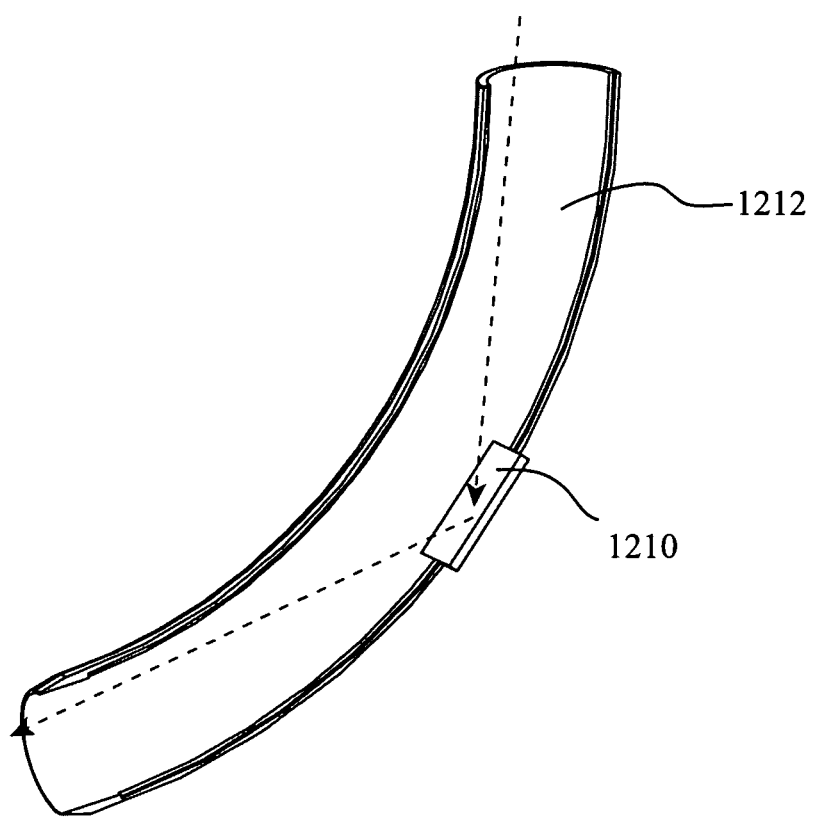
FIG. 35 is a cross-sectional posterior view of an curved cannula with a mirror embedded in an inner wall of the cannula.
Figure 36:
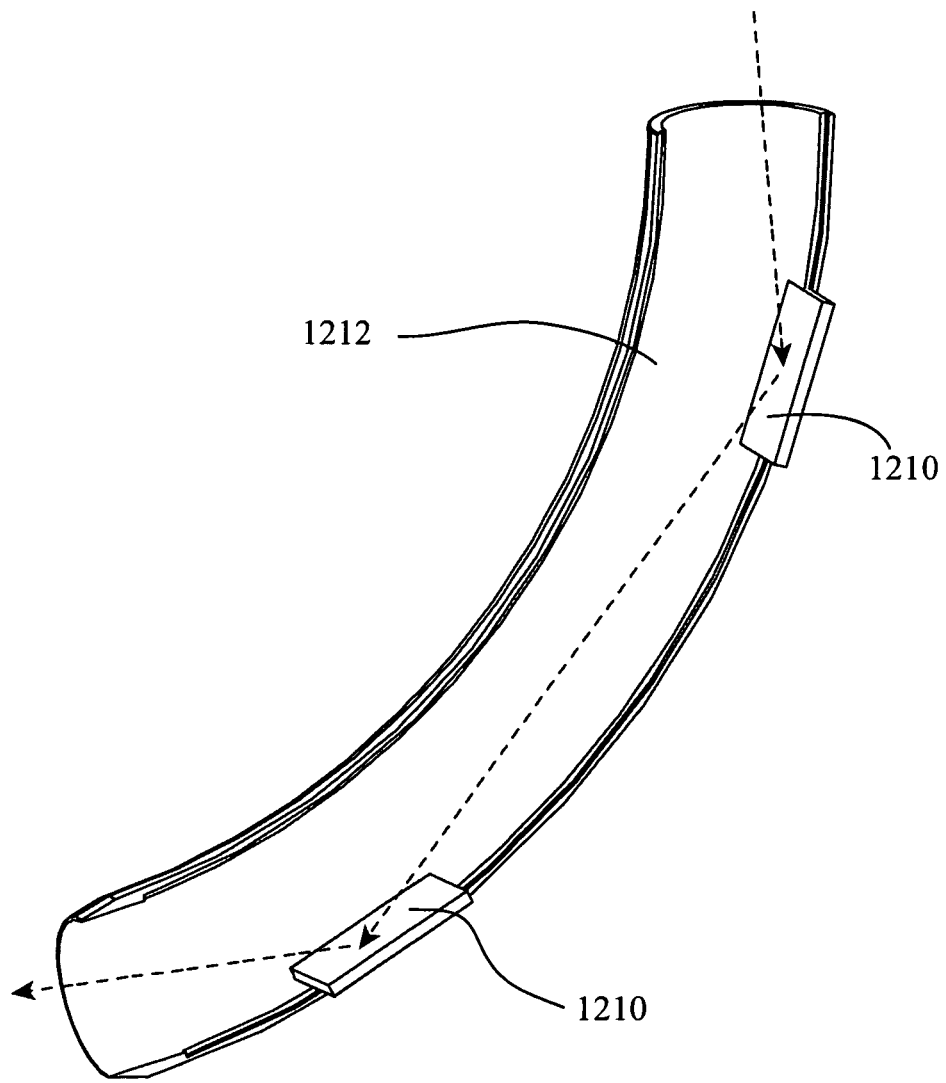
FIG. 36 is a cross-sectional posterior view of an curved cannula with two mirrors embedded in an inner wall of the cannula.
Figure 37:
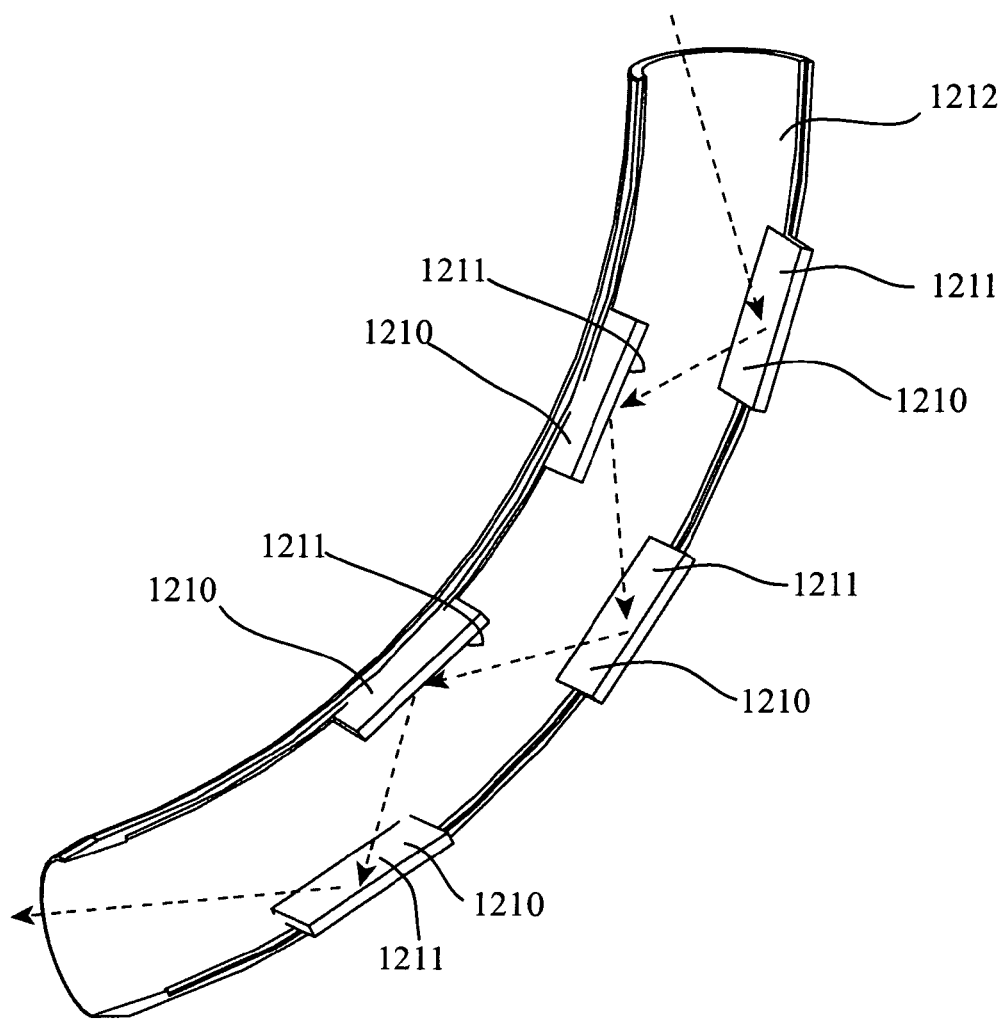
FIG. 37 is a cross-sectional posterior view of an curved cannula with multiple mirrors embedded in an inner wall of the cannula.

Referring to FIGS. 35-42, systems and methods are shown that allow for visualization of objects at the end of a non-straight surgical cannula through which direct visualization is not possible. As seen in FIGS. 35-39, the use of a single, or multiple mirrors placed inside a curved cannulas internal lumen allows for projection of an image from one end of the cannula to the other. FIG. 35 illustrates a partial cross-sectional view of a visualization system with a single mirror 1210 located on the interior wall of a cannula 1212. An unbroken line of sight, represented by the dashed line, extends from one end of the cannula 1212 to the other, reflected by the mirror 1210. Mirror 1210 may be flat, so as not to distort the reflected image. Yet mirror 1210 is small enough so that its presence in the cannula 1212 will not impede instruments or other materials passed through the lumen of the cannula. Mirror 1210 may be separate piece placed within the cannula, or may be a flattened, polished segment of the inner cannula wall. FIG. 36 illustrates a partial cross-sectional view of a visualization system with two mirrors 1210 embedded in the interior wall of the cannula 1212. The mirrors 1210 are placed so that the line of sight is reflected from one mirror surface 1211 to the next and through the cannula. FIG. 37 illustrates a partial cross-sectional view of a visualization system with multiple mirrors which allow the line of sight to extend from one end of the cannula to the other. Multiple mirrors may allow for visualization through a cannula with a greater degree of curvature. The mirror surface of any of the mirrors disclosed herein may comprise polished metal, metal-coated glass, or any other reflective material known in the art.

Figure 38:
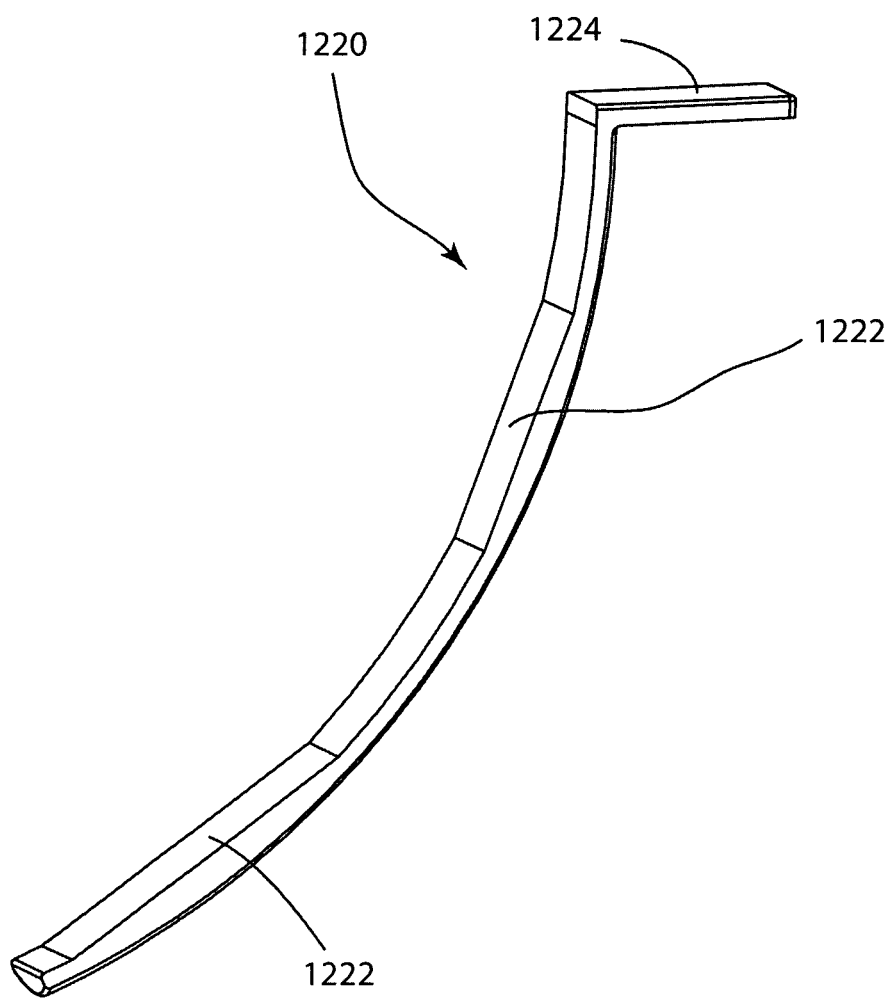
FIG. 38 is a perspective view of an insertable mirror device with multiple mirrored surface.
Figure 39:
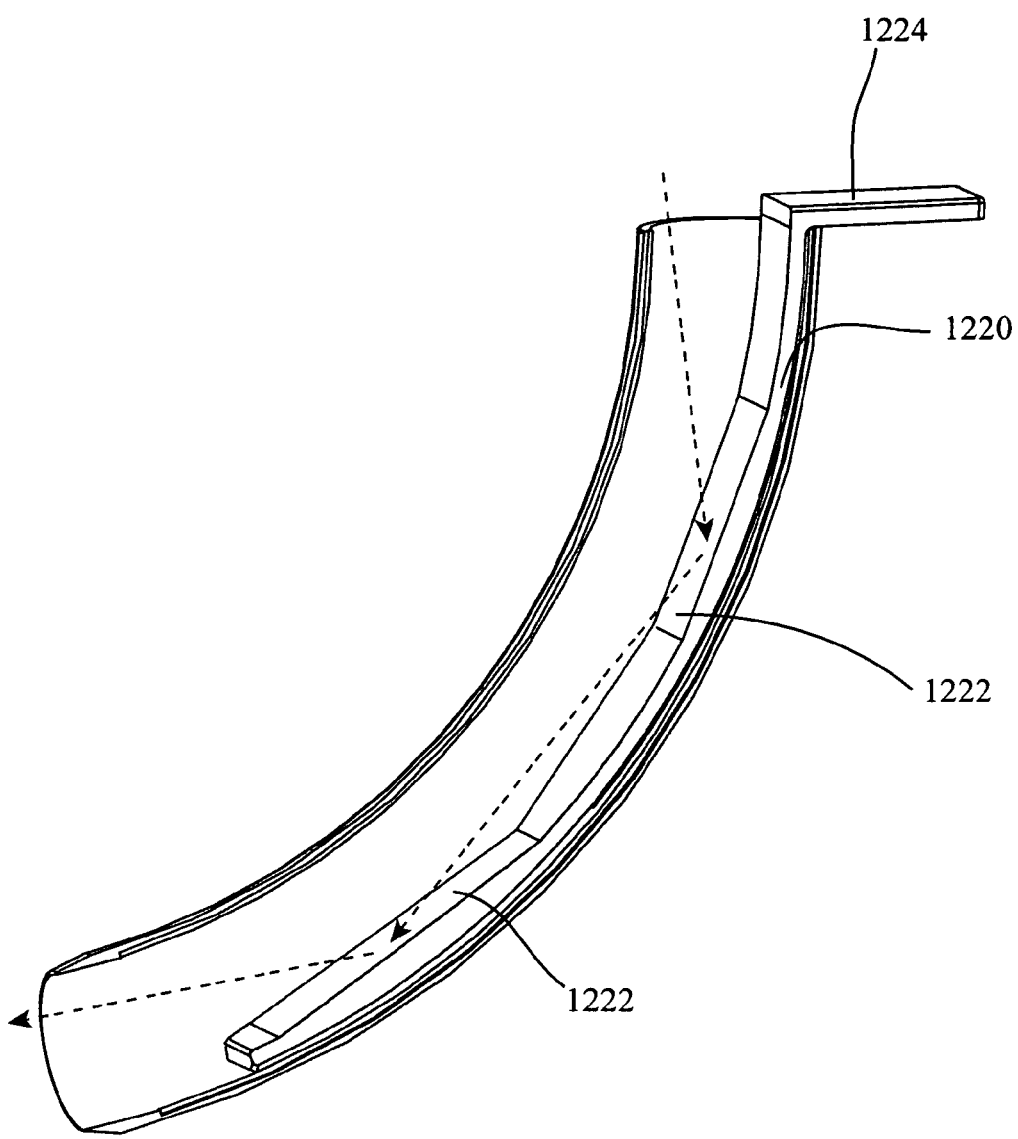
FIG. 39 is cross-sectional view of a curved cannula with the insertable mirror device of FIG. 38 inserted in the cannula.

FIGS. 38 and 39 illustrate a visualization system which may include an insertable mirror device 1220 with multiple mirror surfaces 1222, which can be placed along the interior wall of the curved cannula. The insertable mirror device may be flexible, and may easily be adjusted to different locations along the circumference of the cannula's lumen, allowing visualization from different locations. A handle 1224 allows easy insertion, adjustment and removal of the device 1220, and can prevent over-insertion of the device into the intervertebral space. Removal of the insertable mirror device 1220 may allow other instruments and objects to pass through the cannula more easily. The cannula into which mirror device 1220 is insertable may be cannula 18, cannula 180, cannula 181, or any other cannula disclosed herein. Mirror device 1220 may comprise an engagement feature allowing it to be temporarily locked to a cannula. Mirror device 1220 may also comprise a light source, which may be located on a distal end of the device.

Figure 40:
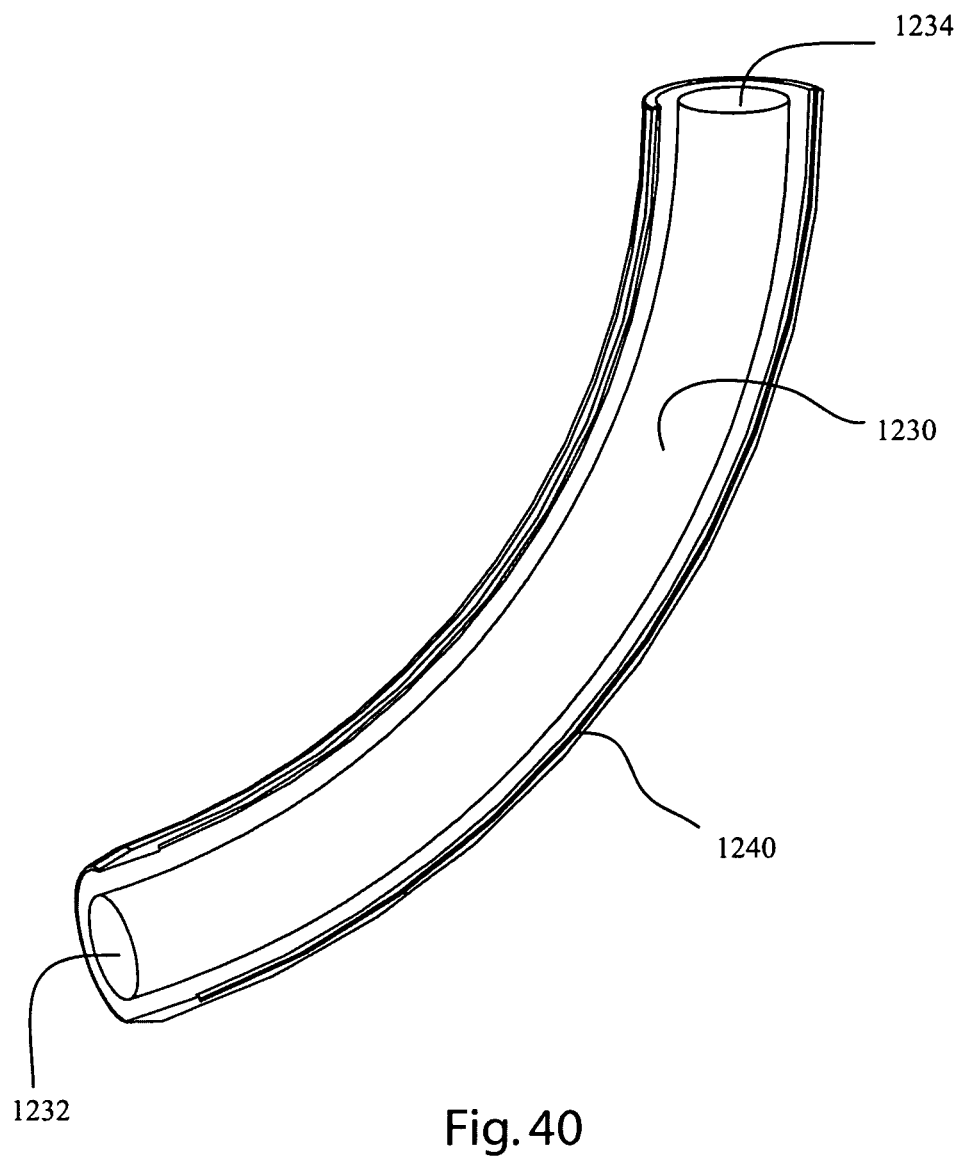
FIG. 40 is a cross-sectional view of a curved cannula with a fiber optic rod inserted in the cannula.
Figure 41:
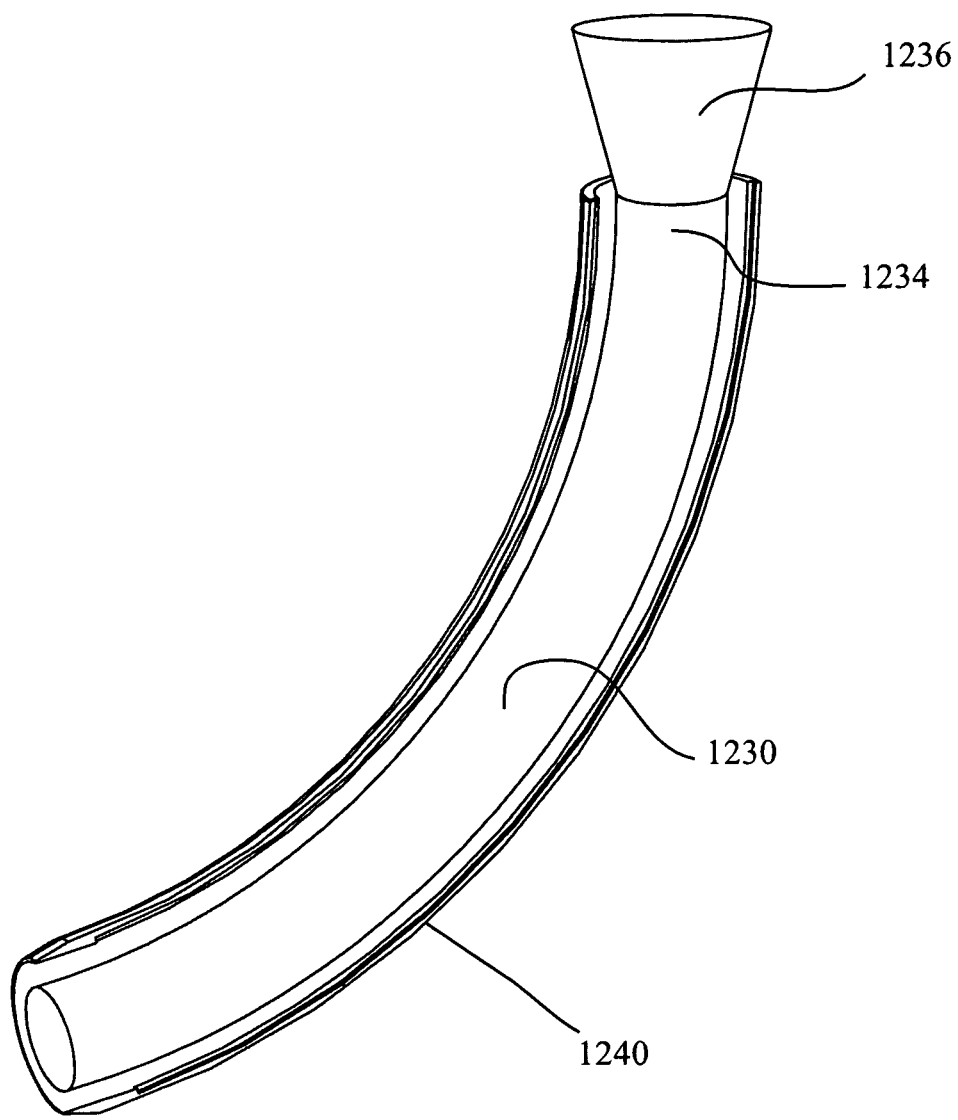
FIG. 41 is a cross-sectional view of the cannula and fiber optic rod of FIG. 40, with a tapered magnifier on a first end of the fiber optic rod.
Figure 42:
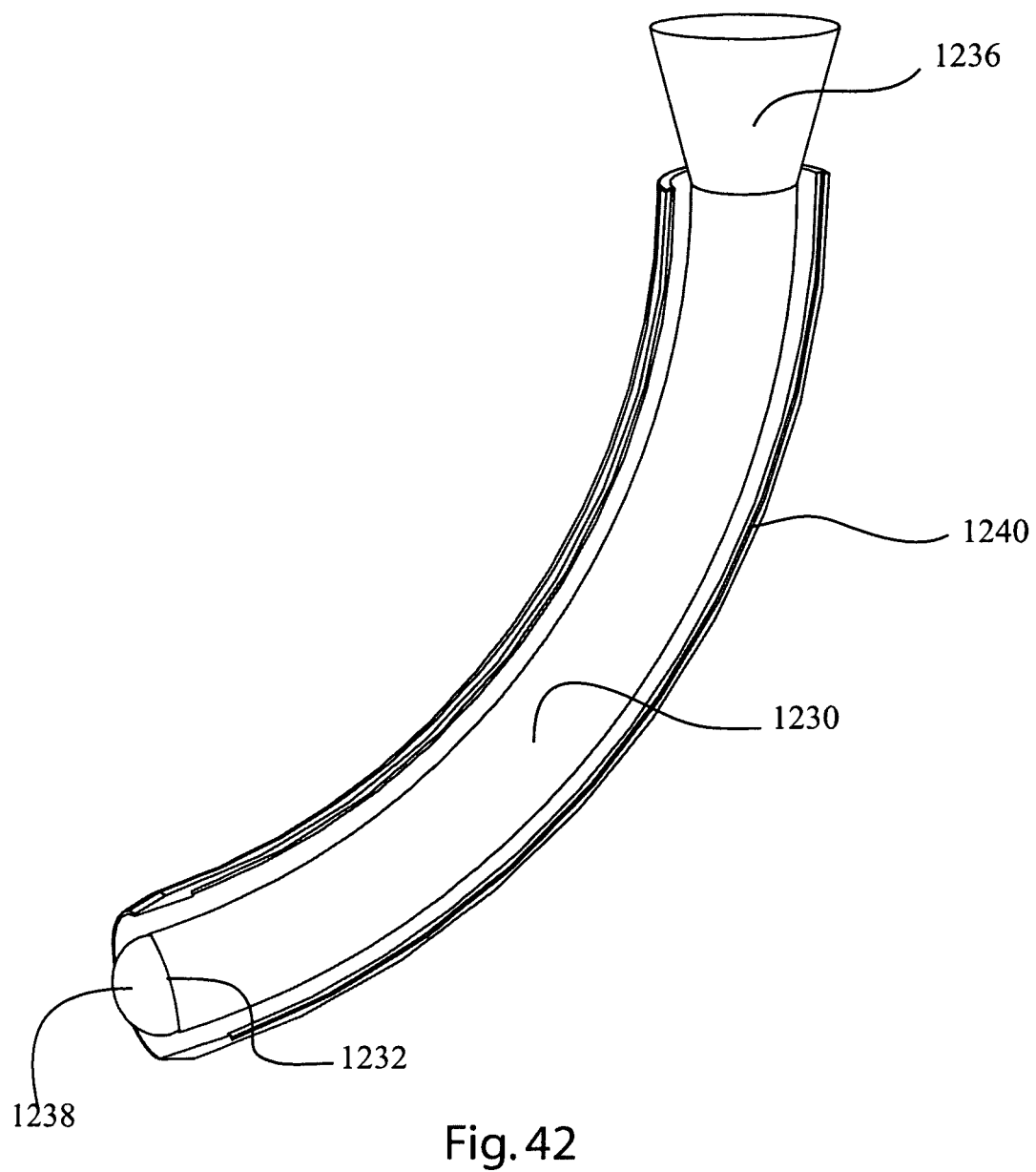
FIG. 42 is a cross-sectional view of the cannula, fiber optic rod and tapered magnifier of FIG. 41, with a lens on a second end of the fiber optic rod.

FIGS. 40-41 illustrate visualization systems which may include an image conduit such as a fiber optic rod. In FIG. 40, a flexible fiber optic rod 1230 is threaded through a curved cannula 1240 to transfer images through the cannula, from a first end 1232 of the fiber optic rod which may inserted adjacent the interbody or disc space, to a second end 1234 which may be external the patient's body. FIG. 41 illustrates a magnification feature 1236 added to the second end 1234 of the flexible fiber optic rod 1230. The magnification feature 1236 allows for magnification of images transferred through the fiber optic rod from the first end 1232 to the second, external end 1234. FIG. 42 includes the magnification feature 1236 plus the addition of a lens portion 1238 on the first end, which may allow for projection of the image as well as supplementing the focus of the image. In alternate embodiments of the invention, a curved rigid fiber optic rod may be used in place of a flexible fiber optic rod. In another embodiment, the lens portion may be included without the tapered magnification feature.

Figure 43:
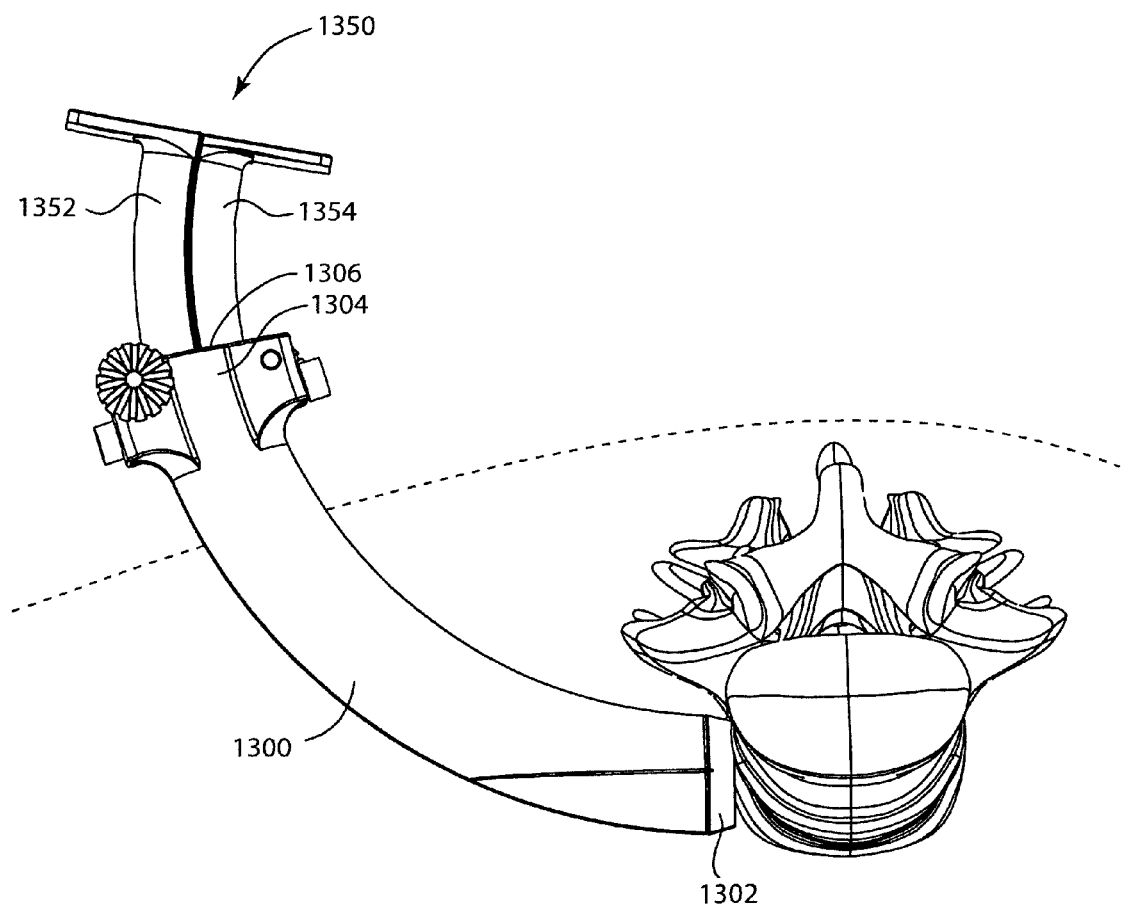
FIG. 43 is a cephalad view of a curved cannula adjacent a portion of a spine, with a two-piece tang assembly partially inserted into the cannula.

Referring to FIG. 43, a system for providing surgical access to a portion of a spine is shown from a caudal perspective. An arcuate cannula 1300 is configured to be inserted into the spinal area from a latero-posterior approach. Arcuate cannula 1300 may comprise aluminum or another biocompatible radiolucent material. A distal end 1302 of the cannula 1300 is positioned adjacent the spine, and may be more specifically positioned tangential to an interspinous space, to provide access to the interspinous space for surgical procedures such as discectomy and/or disc replacement, among others. A proximal end 1304 of the cannula provides an opening 1306 for insertion and manipulation of tools and instruments for surgical techniques and for visualization and targeting of surgical procedures. A tang assembly 1350 is shown partially inserted into the arcuate cannula 1300, the tang assembly 1350 comprising an anterior tang portion 1352 and a posterior tang portion 1354.

Figure 44:
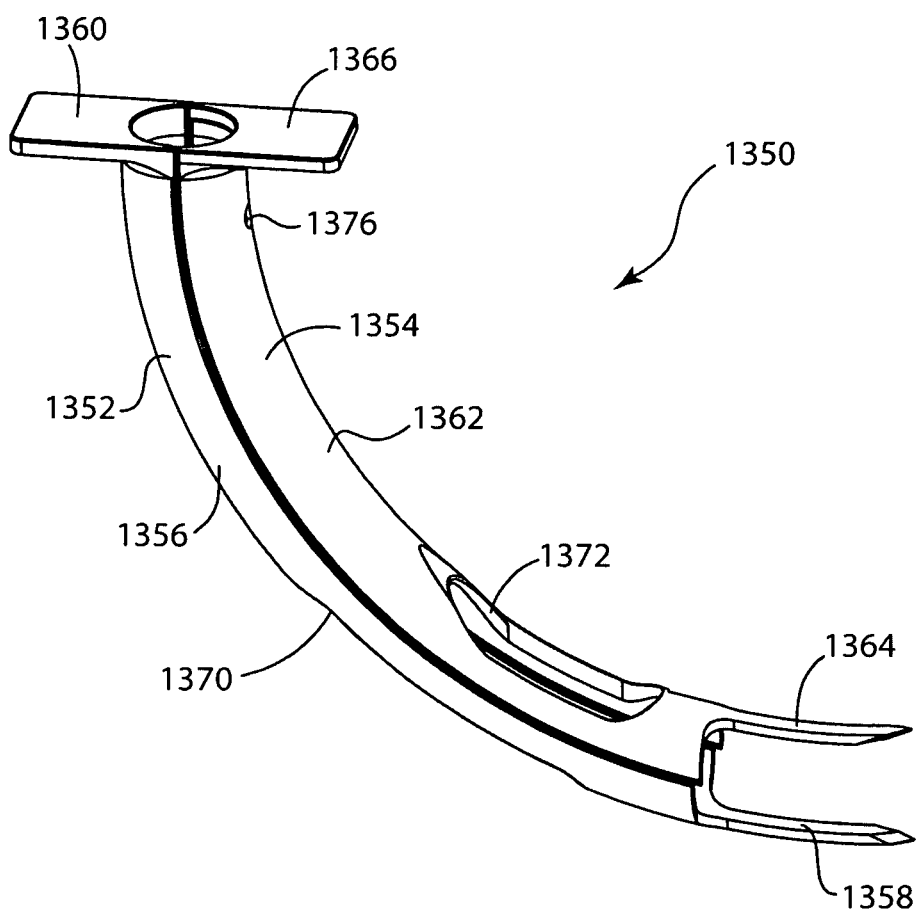
FIG. 44 is a perspective view of the two-piece tang assembly of FIG. 43.
Figure 45:
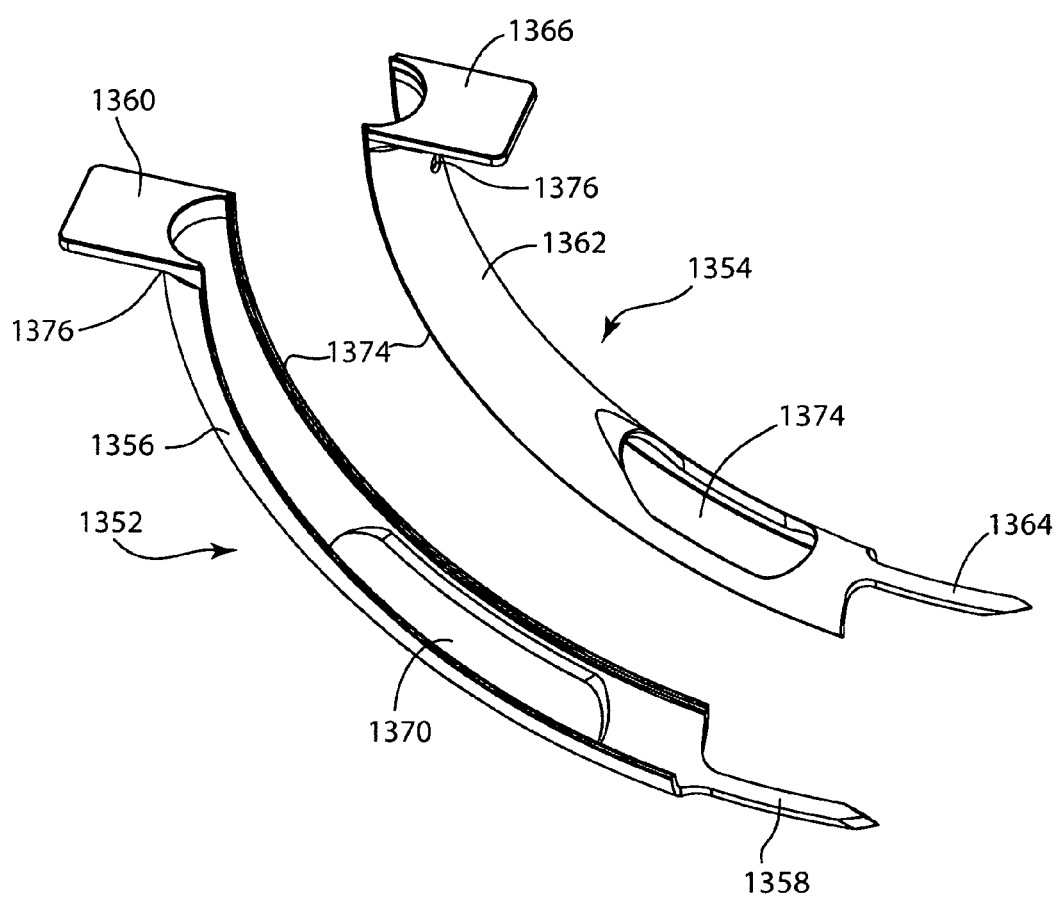
FIG. 45 is an exploded perspective view of the two-piece tang assembly of FIG. 43.

Referring to FIGS. 44 and 45, the tang assembly 1350 is shown in greater detail. Anterior 1352 and posterior 1354 tang portions are shaped to fit together to form a cannula which is sized to be inserted into the arcuate cannula 1300. Anterior tang portion 1352 comprises a curved anterior body portion 1356, a distal end with an anterior tang extension 1358, and a proximal end with an anterior handle 1360. The handle 1360 may be formed monolithically with the body portion 1356, or may be separately formed. The anterior tang extension 1358 is generally narrow, pointed and shaped to fit into the interspinous space between two vertebral bodies, where it may retract tissues, allowing access to the interspinous space. The posterior tang portion 1354 is shaped to complement the anterior tang portion 1352, such that together they form an arcuate cannula. The posterior tang portion 1354 comprises a curved posterior body portion 1362, a distal end with a posterior tang extension 1364, and a proximal end with a posterior handle 1366. The anterior body portion 1356 may have an anterior window 1370, and the posterior body portion 1362 may have a posterior window 1372. The windows 1370, 1372 may allow for visualization and targeting of surgical procedures, using radiography or other techniques. Tang assembly 1350 may comprise stainless steel or another biocompatible material. Stainless steel or a material of similar strength may be preferred to provide sufficient rigidity to the narrow tang extensions 1358, 1364 to prevent bending or other distortion during insertion and other procedures. It is appreciated that alternative embodiments of the tang assembly may include tang extensions located at different angles, to allow insertion along different planes. Specifically, the tang extensions may be located at a 45° angle relative to the handles.

Each tang portion 1352, 1354 may have guiding features 1374 such as rims, ridges or slots, or a combination thereof, on their longitudinal edges. These guiding features may allow the tang portions to slide into alignment and join with one another as they are inserted, and may prevent misalignment or separation after the two portions are joined together. Each tang portion 1352, 1354 may also have a locking feature such as a locking port 1376.

Figure 46:
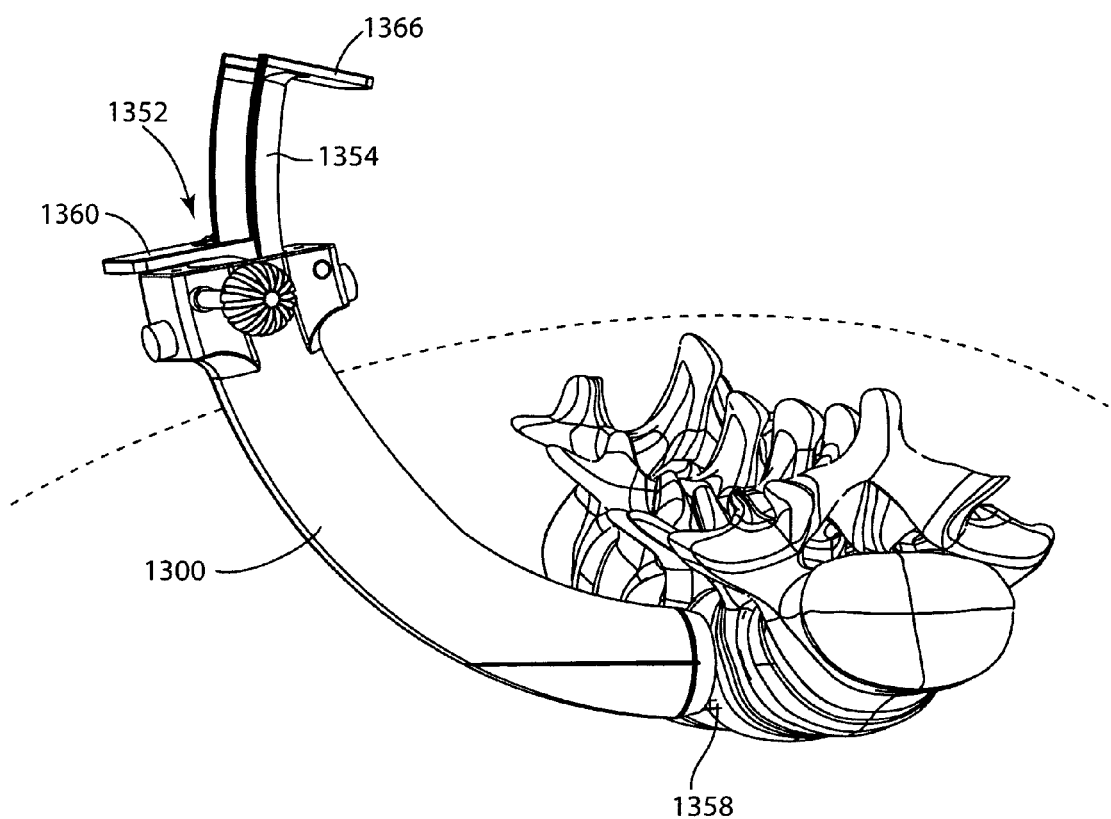
FIG. 46 is a medial-cephalad view of the cannula, two-piece tang assembly and spine of FIG. 43, with one tang piece partially inserted into the cannula.
Figure 47:
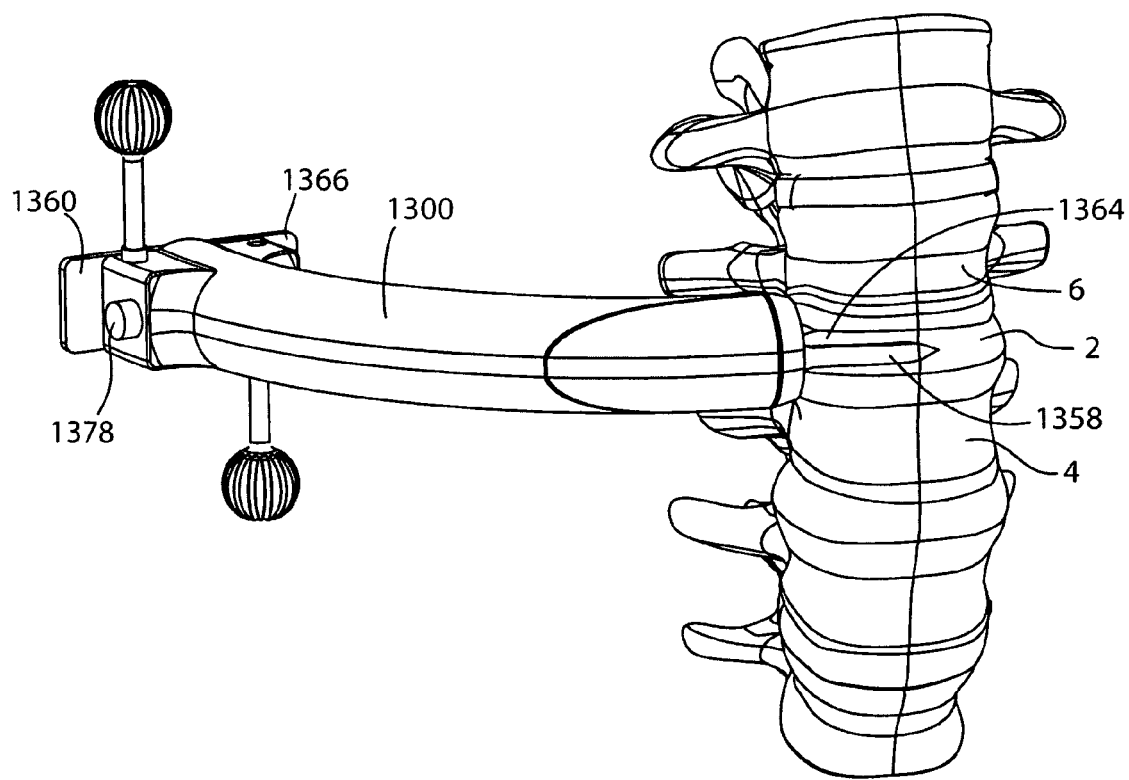
FIG. 47 is an anterior view of the cannula, two-piece tang assembly and spine of FIG. 43.

FIGS. 43, 46 and 47 illustrate how the tang assembly 1350 may be inserted into the arcuate cannula 1300. FIG. 43 shows anterior 1352 and posterior 1354 tang portions being inserted into the cannula 1300 substantially simultaneously. The guiding features 1374 on each longitudinal edge may have been joined prior to insertion into the cannula. Insertion may continue until the tang extensions are positioned in the interspinous space, and the handles 1360, 1366 are adjacent the proximal end 1304 of the cannula, preventing further insertion.

FIG. 46 illustrates separate insertion of the tang portions 1352, 1354 into the cannula 1300. Anterior tang portion 1352 has been fully inserted, and posterior portion 1354 has been partially inserted. The tang portions may be inserted in either order, or together as previously described. During a procedure, a practitioner may also choose to only insert one tang portion, anterior or posterior, if desired.

FIG. 47 is an anterior perspective view illustrating tang portions 1352, 1354 fully inserted into the arcuate cannula 1300. Locking features such as locking ports 1376 (not seen in FIG. 48) may cooperate with locking members 1378 to form locking mechanisms which can lock each tang portion in place in the cannula 1300, preventing movement and/or back-out from the cannula. Locking member 1378 may comprise a bolt, pin, spring pin, snap, or other member capable of forming a locking mechanism with tang portion 1352 and/or 1354. Anterior tang extension 1358 extends generally medial-laterally across the anterior edge of intervertebral space 2 between vertebral bodies 4 and 6. Opposite from anterior tang extension 1358, posterior tang extension 1362 extends generally medial-laterally across the posterior edge of intervertebral space 2 between vertebral bodies 4 and 6. The tang extensions 1358, 1362 may maintain the vertebral body spacing and provide tissue retraction, preventing unwanted tissue encroachment into the intervertebral space 2 during subsequent surgical procedures. Upon completion of the surgical procedures, the tang portions 1352, 1354 may be unlocked and removed from the cannula 1300, either singly or together.

Figure 48:
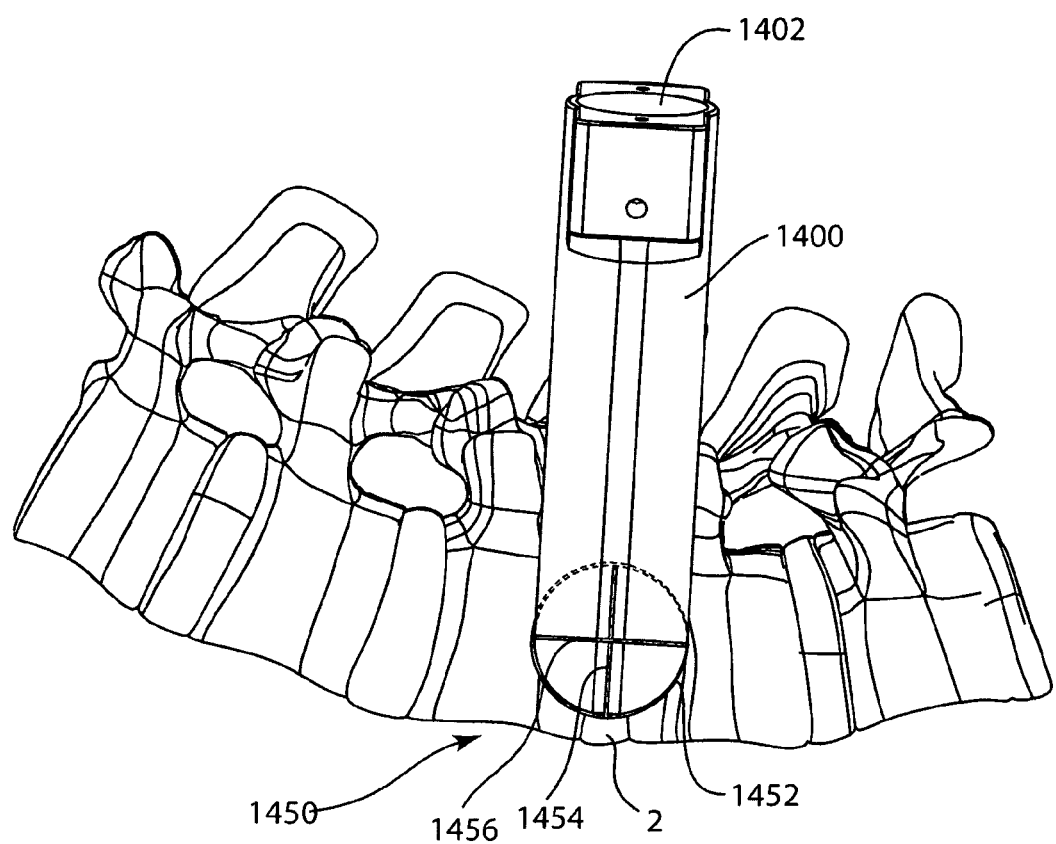
FIG. 48 is a medial view of an arcuate cannula with a referencing marker system, adjacent a portion of a spine.
Figure 49:
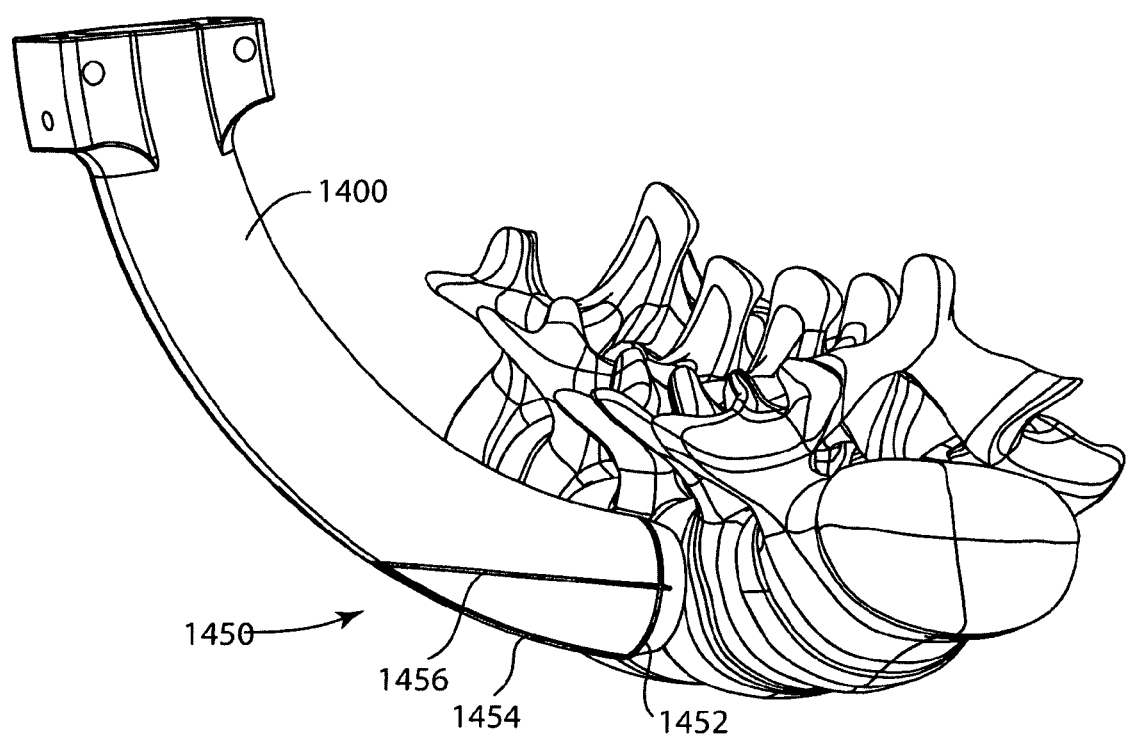
FIG. 49 is a medial-cephalad view of the cannula, referencing marker system and spine of FIG. 48.
Figure 50:
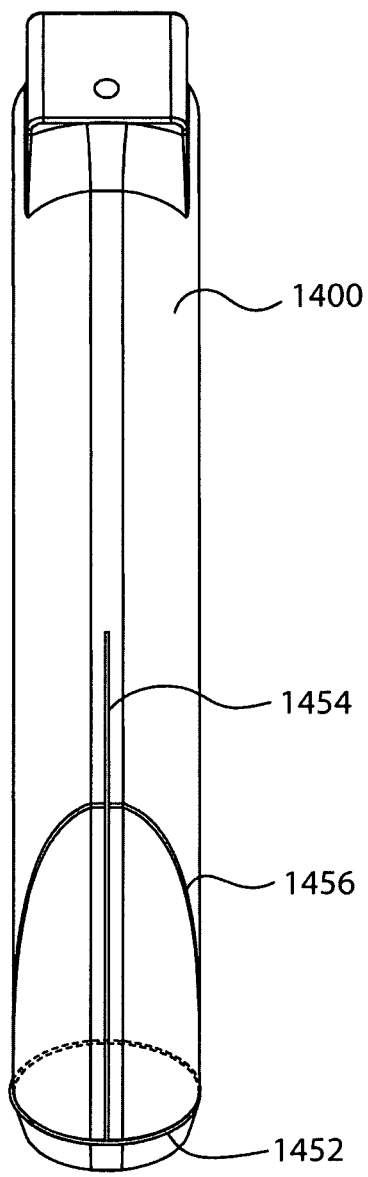
FIG. 50 is a perspective view of the cannula and referencing marker system of FIG. 48.

FIGS. 48 through 50 illustrate an embodiment of a visual referencing system for use with a spinal access cannula. Referring to FIG. 48, a lateral view of a portion of a spine is shown, with arcuate cannula 1400 positioned to extend from a latero-posterior location to an interspinous space 2. FIG. 49 illustrates the cannula 1400 and the marker system 1450 from a caudal perspective, and FIG. 50 from latero-anterior perspective. The cannula 1400 may comprise aluminum or another radiolucent material.

The cannula 1400 further comprises a visual referencing, or marker system 1450, which in turn comprises radio-opaque tantalum (Ta) markers joined to the cannula. The markers may comprise strips of tantalum or other radio-opaque material, and may be joined to the cannula through means including laser welding, brazing, tape, adhesive, paint, or heat bonding, among other methods. A first marker 1452 encircles a circular distal end of the cannula 1400, a second marker 1454 extends from a distal end of the cannula along its anterior wall, and an third marker 1456 arcs from a lateral side of the distal end of the cannula across the second marker 1454 and to the opposite side of the distal end. When the arcuate cannula 1400 is in a preferred orientation, and radiographically viewed from a lateral perspective, the three tantalum markers 1452, 1454, 1456 combine to form a crosshair in a circle, as seen in FIG. 48. A combination of antero-posterior and lateral radiographs may be used as guides to align the markers. In a preferred orientation in which the distal opening of the arcuate cannula is tangential to the interspinous space 2, the crosshairs are aligned or targeted on the interspinous space. Third tantalum marker 1456, which has a general orientation in the cephalad-to-caudal direction, forms an upwards facing arc when the distal end 1402 of the arcuate cannula 1400 is pointing more posterior and forms a downward facing arc when the distal end is facing more anterior. This helps to guide the surgeon such that the exit direction of the instruments and implants that are delivered through the cannula 1400 eventually exit in a preferred orientation. This preferred orientation prevents the instruments and implants delivered through the cannula 1400 from exiting the disc space and disrupting the anterior vascular structures or the posterior neurovascular tissues. Once a preferred orientation is achieved, the cannula 1400 may be locked into that orientation via an external clamping system or other locking device.

The marker system 1450 allows visual referencing of instruments and procedures relative to the cannula 1400 and the interspinous space. Radio-opaque instruments may be inserted through a central bore 1402 of the cannula and manipulated to carry out procedures in the interspinous space. Using the marker system 1450, the relative positions of such instruments can be monitored through radiography.

The arcuate cannula 1400 and marker system 1450 may be used in conjunction with the tang assembly 1350 shown in FIGS. 43-47. The anterior 1352 and posterior 1354 tang portions may be inserted through the cannula 1400, with the tang extensions 1358, 1364 bracketing the interspinous space. The windows 1370, 1372 are positioned to cooperate with the markers 1452, 1454, 1456 to allow visualization of the markers during radiography.

Figure 51:
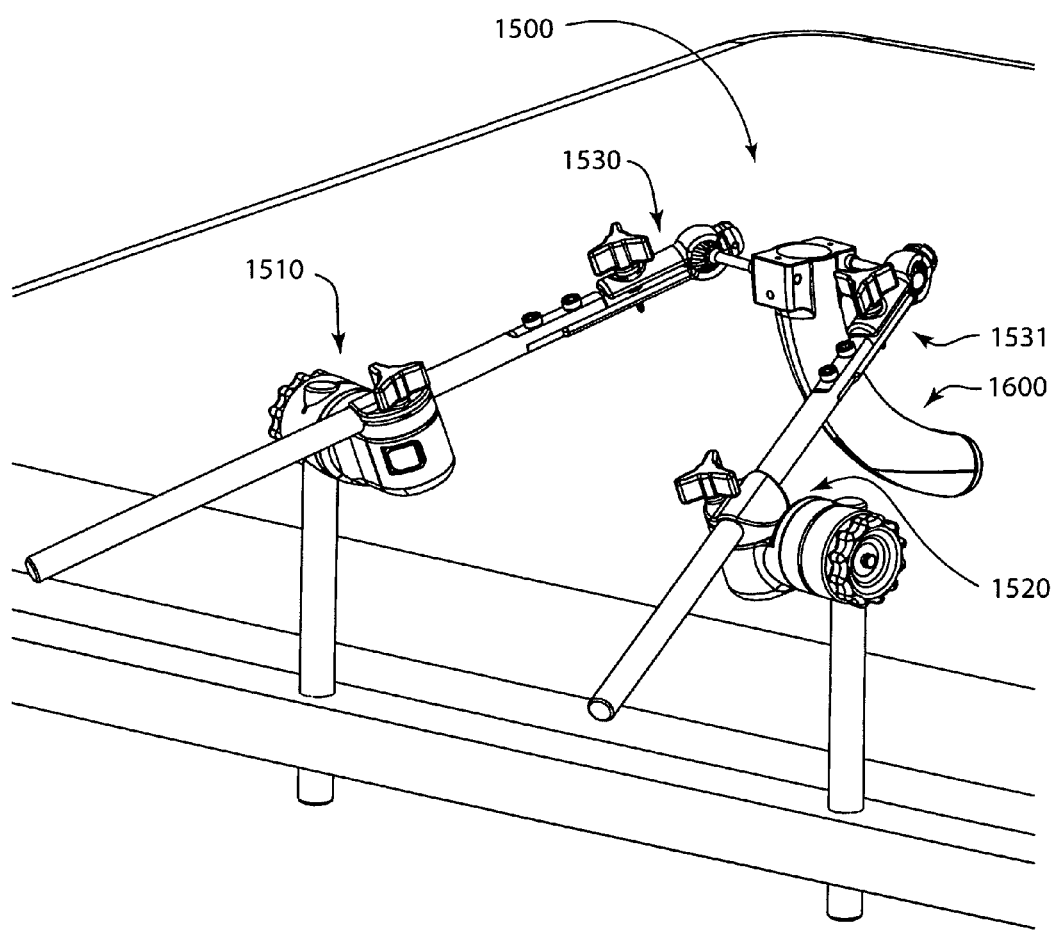
FIG. 51 is a perspective view of a positionable clamping system and the cannula of FIG. 43, attached to an operating table.

Referring to FIG. 51, a clamp system 1500 may be used to support, adjust and lock the orientation and position of a spinal access cannula system 1600 relative to a patient and/or an operating table. Clamp system 1500 comprises a first table mounted support system 1510, a second table mounted support system 1520, a first polyaxial clamp assembly 1530 and a second polyaxial clamp assembly 1531. First and second table mounted support systems 1510, 1520 may comprise identical components and may differ only in their relative orientation after assembly. Table mounted support systems 1510, 1520 are multi-axial and may be used to adjust the height of the spinal access cannula system 1600 relative to the table, the distance of the spinal access cannula system from the edge of the table, and the angular orientation of the spinal access system 1600 with respect to the table mounted support systems 1510, 1520.

Figure 52:
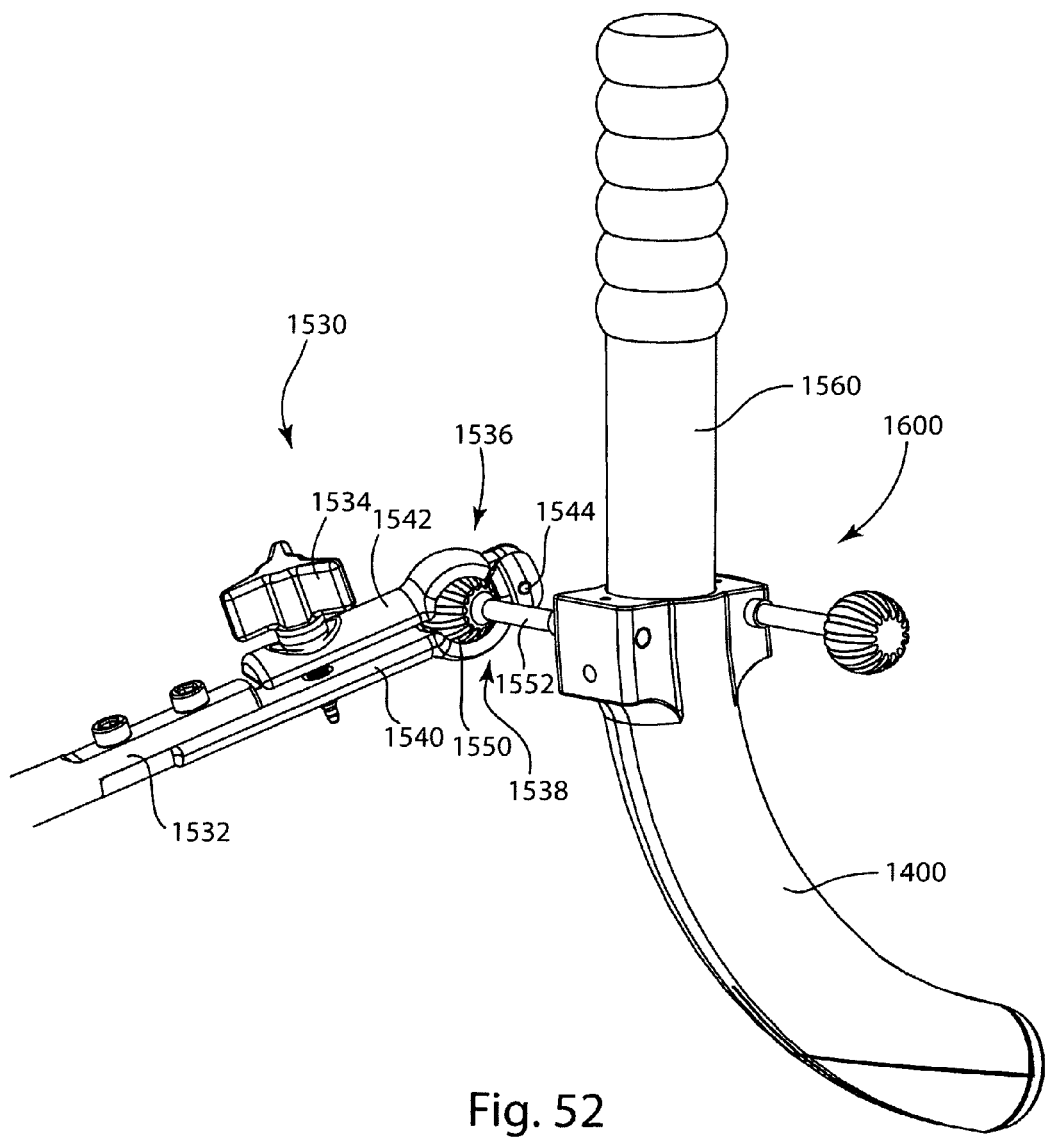
FIG. 52 is an enlarged view of a connection between the positionable clamping system and cannula of FIG. 51, and a joystick handle.
Figure 53:
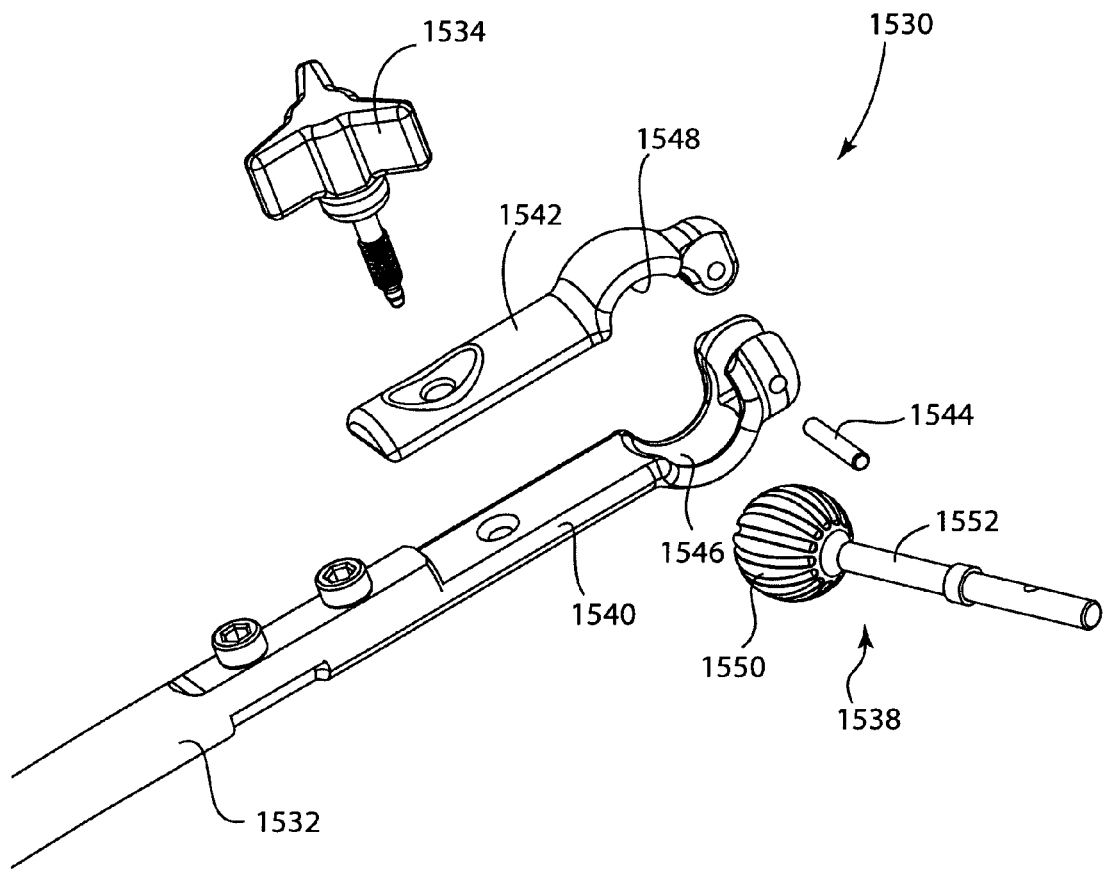
FIG. 53 is an exploded view of the connection of FIG. 52.

First and second polyaxial clamp assemblies 1530, 1531 are identical and differ only in their positioning relative to the spinal access cannula system 1600. Polyaxial clamp assembly 1530 is shown in greater detail in FIGS. 52 and 53. Polyaxial clamp assembly 1530 comprises a support arm 1532, a fastener 1534, a clamp 1536, and a polyaxially adjustable linking member 1538. Support arm 1532 connects to the table mounted support system 1510, and is connected to the clamp 1536. Clamp 1536 comprises a first jaw 1540, a second jaw 1542, and a hinge pin 1544. The support arm 1532 may be monolithically formed with the first or second jaw. First jaw 1540 has a first spherical pocket 1546 and second jaw 1542 has a second spherical pocket 1548. The first and second jaws 1540, 1542 are joined by the hinge pin 1544 such that the first and second spherical pockets 1546, 1548 oppose one another.

Linking member 1538 comprises a spherical head 1550 and a connecting rod 1552. Connecting rod 1552 may be rigidly connected to a spinal access cannula such as arcuate cannula 1400. Spherical head 1550 may be placed in the first spherical pocket 1546, and the second jaw 1542 closed such that second spherical pocket 1548 surrounds the spherical head 1550. The clamp 1536 may be partially tightened by actuating the fastener 1534 to draw the first and second jaws together. Before the clamp 1536 is fully tightened, the spherical head 1550 may be polyaxially rotated to provide a preferred orientation of the cannula 1400. Spherical head 1550 may be ridged, knurled, grooved or have other features or coatings to enhance a secure connection between the head and the jaws. When the preferred orientation is attained, the clamp 1536 is fully tightened by further actuation of the fastener 1534. A locking mechanism such as a nut (not shown) may lock the position of the fastener. Optionally, a cannula extension 1560 may be inserted into the proximal end of the cannula 1400, and rotationally operated like a joystick to fine tune the orientation of the cannula 1400 before the clamp 1536 is fully tightened. If further adjustment is required, the clamp 1536 may be loosened by actuating the fastener 1534 and then re-tightened after polyaxial adjustment of the spherical head 1550. The fastener 1534 is offset from the first and second spherical pockets in the first and second jaws, which provides a mechanical advantage as the first and second jaws are drawn together to lock around the spherical head.

As seen in FIG. 51, the cannula system 1600 is held in place by first and second clamp assemblies 1530, 1531. These assemblies are joined to the cannula system 1600 on opposite sides of the cannula, such that each clamp/linking member connection is on a separate axis. This configuration prevents unwanted rotation of the cannula about either clamp/linking member axis. However, if desired only one side of the clamp system 1500 may be used, such as first table mounted support system 1510, and first polyaxial clamp assembly 1530, to provide unilateral support to the cannula system 1600. It is appreciated that clamp system 1500 may be configured to support arcuate cannula access system 10, 1600, or any targeting and/or access system disclosed herein.

Figure 54:
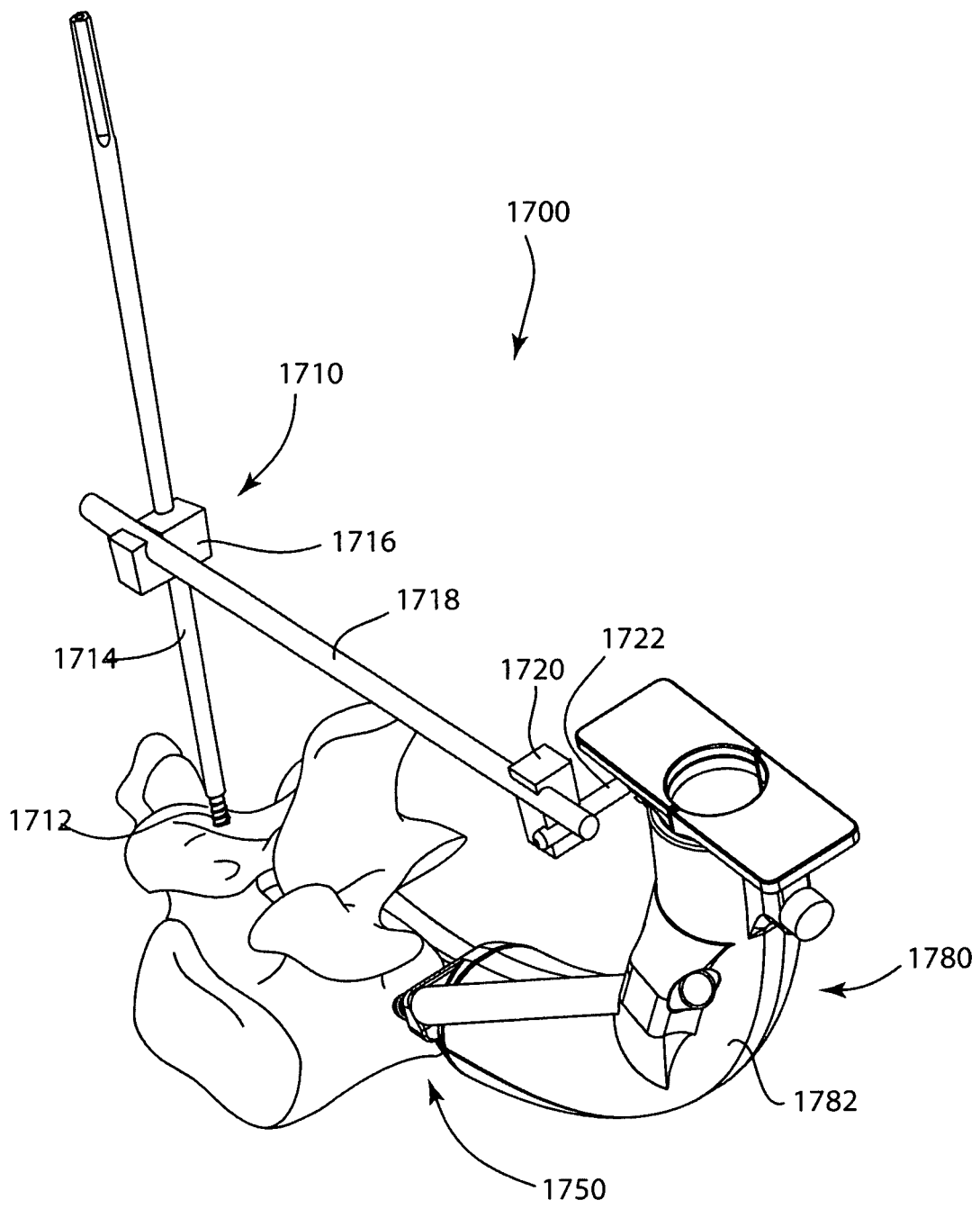
FIG. 54 is a posterior perspective view of an arcuate cannula, a tang assembly, a pedicle docking assembly and a vertebral body docking assembly, joined to a portion of a spine.

Referring to FIG. 54, an alternative embodiment of a spinal access cannula support system is shown. Vertebral docking system 1700 comprises an adjustable pedicle docking assembly 1710, and a vertebral body docking assembly 1750, connected to a spinal access cannula assembly 1780. This system allows docking of the cannula directly to the spine adjacent the spinal access assembly.

Pedicle docking assembly 1710 includes at least one pedicle screw 1712 joined to a first shaft 1714. A first clamping joint 1716 couples first shaft 1714 to a second shaft 1718, and second clamping joint 1720 couples second shaft 1718 to a third shaft 1722, which is coupled to a proximal end of an access cannula 1782. Additional shafts and clamping joints may be added to the system as desired to add additional degrees of freedom of adjustability. Each clamping joint provides adjustability along at least two orthogonal axes. It is appreciated that polyaxial clamping joints could be provided which would provide additional adjustability along at least three axes.

Figure 55:
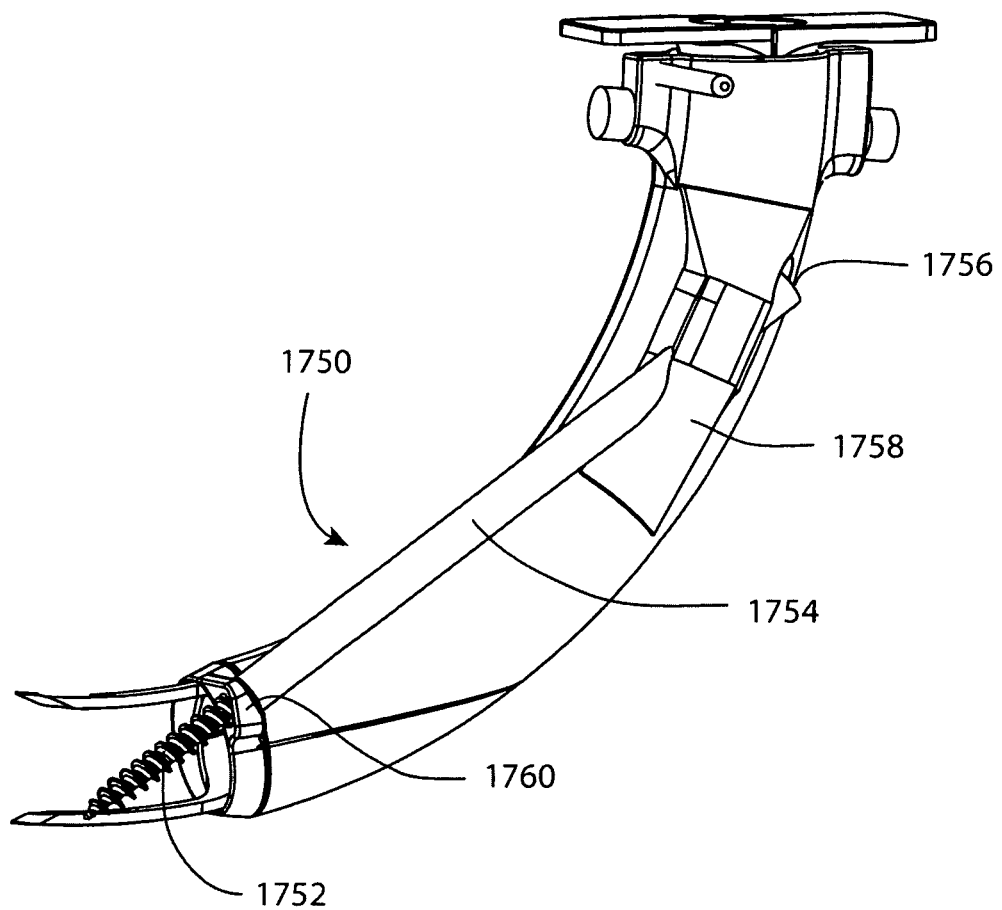
FIG. 55 is a perspective view of the arcuate cannula, tang assembly and vertebral body docking assembly of FIG. 54.

Referring to FIG. 55, a caudal vertebral body docking assembly 1750 comprises bone screw 1752, and a guide sleeve 1754. Guide sleeve 1754 is generally tubular in form and may be monolithically formed with arcuate cannula 1782, or removably coupled to arcuate cannula 1782 through a first guide bracket 1758. Guide sleeve 1754 provides a lumen 1756 though which the bone screw 1752 may be inserted. A driver (not shown) may be inserted into the lumen 1756 to drive the bone screw into a vertebral body. A head on the bone screw 1752 engages with a second guide bracket 1760 positioned on the distal end of the cannula 1782, preventing the screw from exiting the lumen, and fastening the cannula 1782 to the vertebral body.

Figure 56:
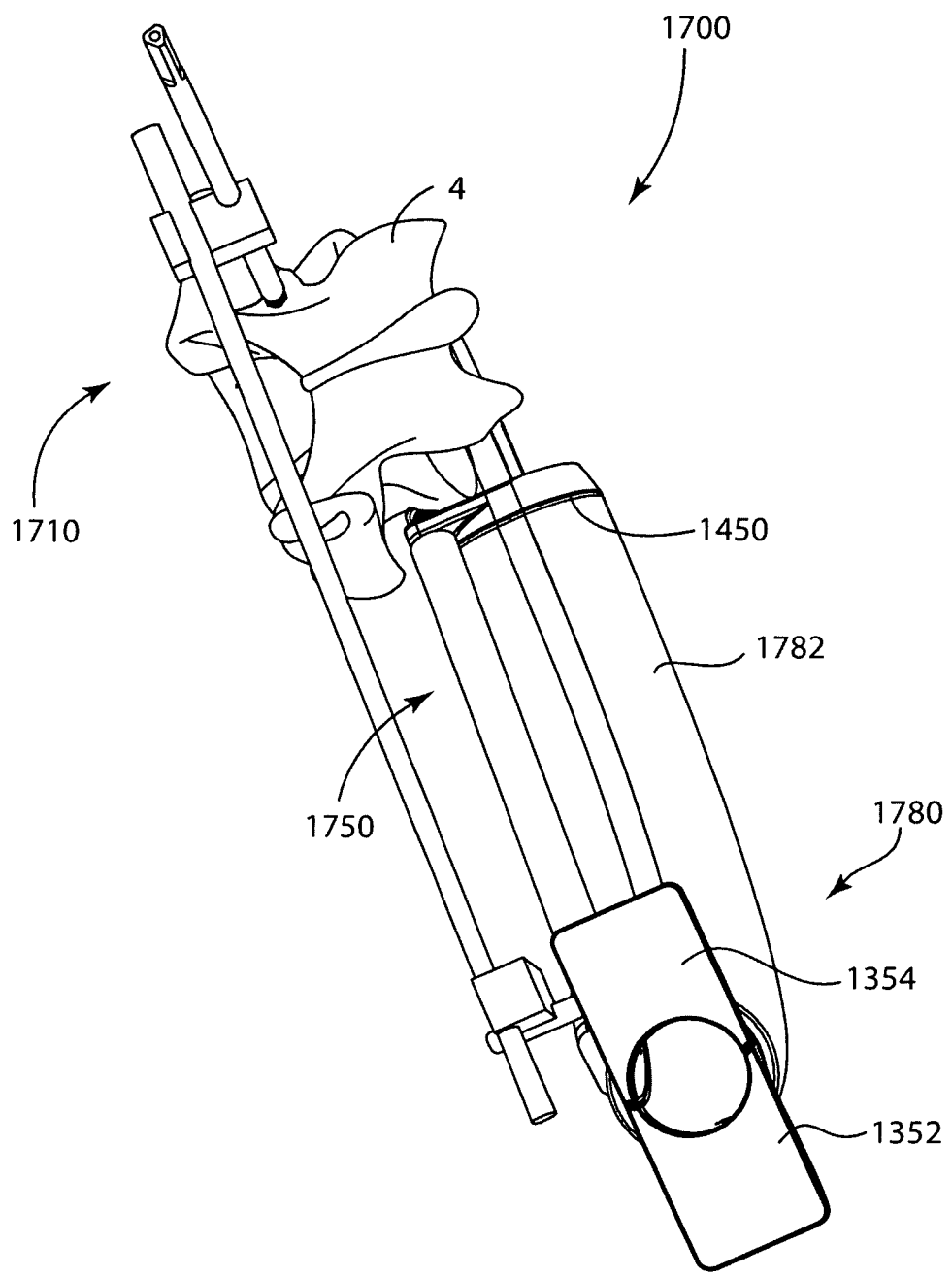
FIG. 56 is a posterior view of the arcuate cannula, tang assembly, pedicle docking assembly and vertebral body docking assembly, and spine of FIG. 54.

Referring to FIG. 56, a posterior view demonstrates how pedicle docking assembly 1710 and vertebral body docking assembly 1750 may be deployed simultaneously to support and stabilize a spinal access cannula assembly 1780. Of course, each system 1710, 1750 may be used independently to support a spinal access cannula assembly. Pedicle docking assembly 1710 secures arcuate cannula 1782 to the right side pedicle on vertebra 4, and vertebral body docking assembly 1750 secures arcuate cannula 1782 to the left side of the vertebral body of vertebra 4. This cross-vertebra support, provided on two separate axes, may prevent unwanted rotation of the cannula assembly around the medial-lateral axis and prevent unwanted translation of the cannula assembly along the medial-lateral access. As seen in FIG. 56, it is appreciated that anterior 1352 and posterior 1354 tang portions may be inserted into arcuate cannula 1782 to provide tissue retraction. Additionally, arcuate cannula 1782 may include radio-opaque marker system 1450, providing a visual referencing system as set forth previously. It is appreciated that any of the spinal access cannula systems disclosed herein may comprise at least one of the docking assemblies 1710, 1750.

Figure 57:
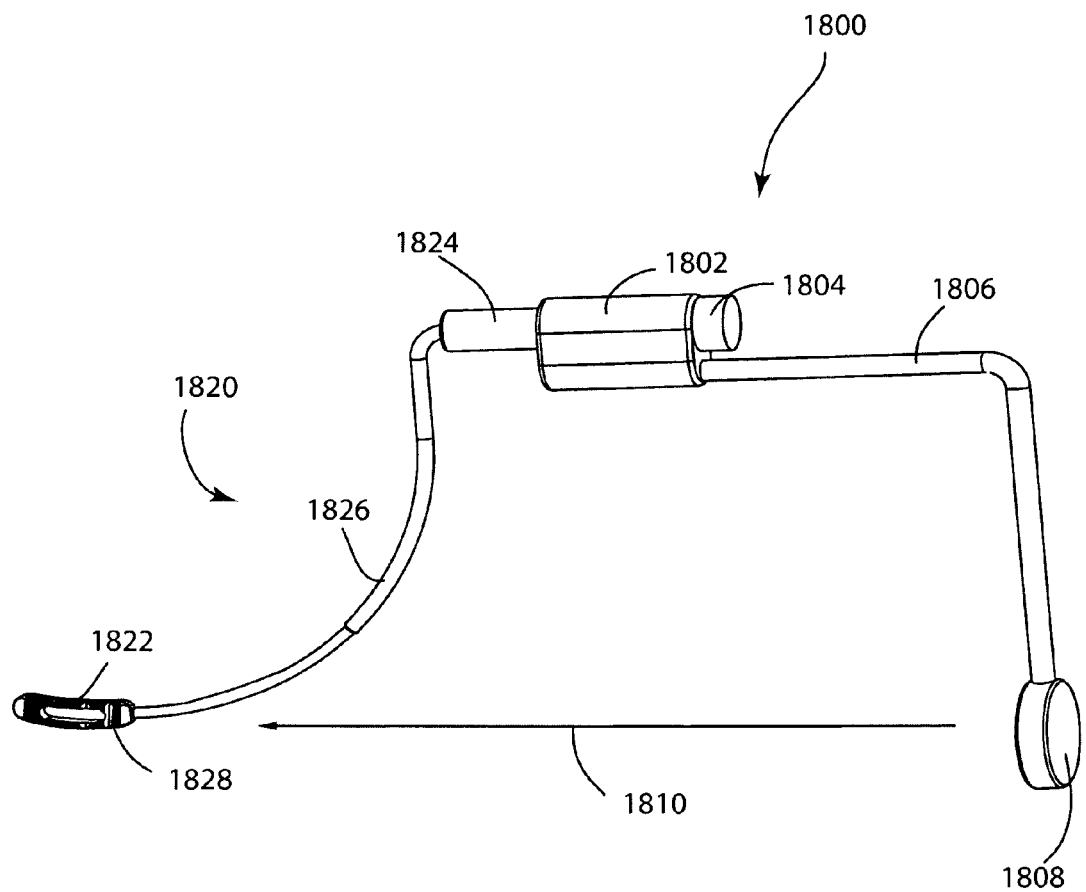
FIG. 57 is a perspective view of a gooseneck tool assembly shaped to be operable through an arcuate cannula.

Referring to FIG. 57, a perspective view of a gooseneck assembly 1800 configured to be operable through an arcuate spinal access cannula is shown, with a tool 1820 comprising a rasp head 1822 secured thereto. Gooseneck assembly 1800 comprises a base 1802, a securing member 1804, a neck 1806, and a strike plate 1808. A variety of tools shaped to be inserted through an arcuate spinal access cannula such as cannula 1400 may be secured to the assembly 1800, including but not limited to: a rasp, an intervertebral implant trial, an intervertebral implant insertion tool, a curette, discectomy instruments, and annulotomy instruments. Each tool 1820 may comprise a handle 1824 securable to the base 1802, a curved shaft 1826, and a working end or end effector 1828 which in FIG. 57 is a combination trial/rasp 1822. Means for securing each tool 1820 to the assembly 1800 may include a bolt member or other threaded means, a spring pin, a snap fit, a press fit, or a locking pin or nut, among others. Gooseneck assembly 1800 is configured such that when a force is applied to the strike plate 1808 by a hammer or other means, the component of the force vector perpendicular to the strike plate passes through the end effector of the attached tool, as indicated by vector 1810.

Obtaining access to the intervertebral space at the L4-L5 vertebral level may be problematic due to the presence of the ilium, which projects cephaladly such that the iliac crest is cephalad to the L4-L5 intervertebral level. Thus, a strictly lateral approach to the intervertebral space may be blocked by the ilium. FIGS. 58-69 illustrate systems and methods suitable for creating access to the spine at the L4-L5 vertebral level from a postero-lateral approach while avoiding violation of the ilium.

Figure 58:
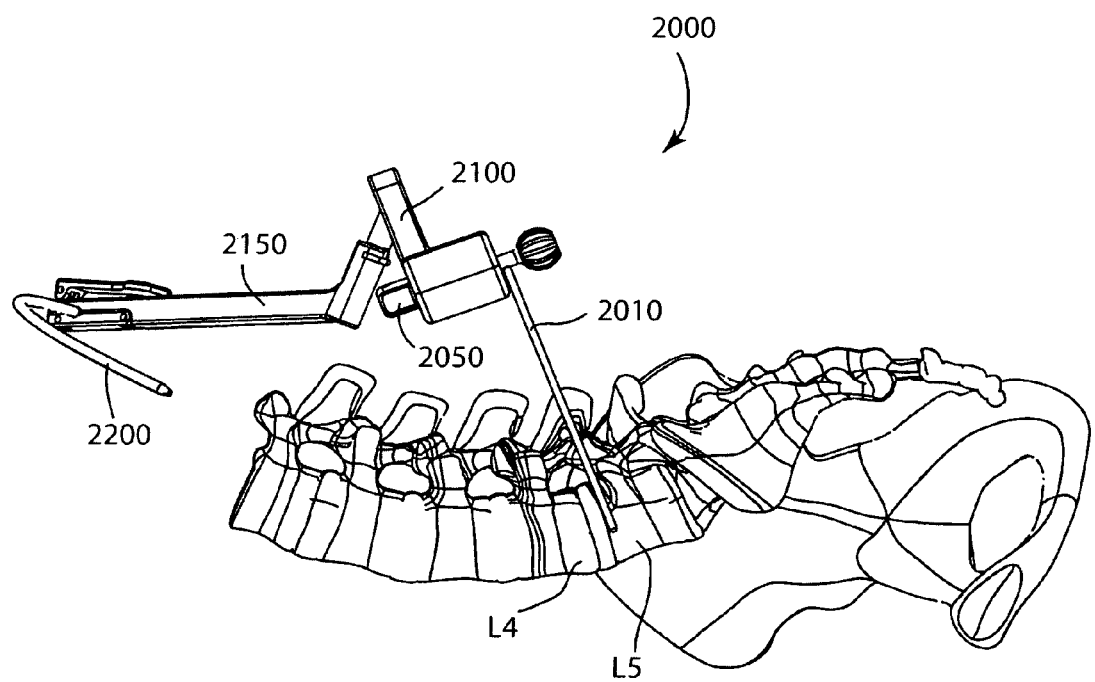
FIG. 58 is a medial view of a spinal access system comprising a targeting member, micrometer assembly, adapter member, swing arm and penetrating member.

FIG. 58 illustrates a spinal access system 2000 positioned proximate to the L4-L5 intervertebral space in a portion of a spine. The left ilium is not depicted in order to view the entire spinal access system. Spinal access system 2000 comprises targeting member 2010, micrometer assembly 2050, adapter member 2100, swing arm 2150 and penetrating member 2200. As shown in FIG. 58, targeting member 2010 may be positioned such that a distal end is at a reference location proximate the spine. Swing arm 2150 may be rotated, driving penetrating member 2200 through an incision in the skin, along an antero-medial-caudal curved path, until a distal end of the penetrating member is at a target location having a known position relative to the reference location. The curved path may be oblique to the sagittal, coronal and transverse planes of the patient. In contrast to entering the intervertebral space from a plane substantially parallel to the intervertebral space, the spinal access system 2000 employs an approach from a substantially oblique plane. Micrometer assembly 2050 may be actuated to fine-tune a cephalad-caudal distance between the target location and the reference location. After insertion of the penetrating member along the curved path, it may be released from the swing arm, and one or more curved cannulas (not shown) may be slid over the penetrating member. Then the penetrating member is removed from the cannula, whereafter the bore of the cannula provides access from outside the body at the incision location to the target location along the curved path.

Figure 59:
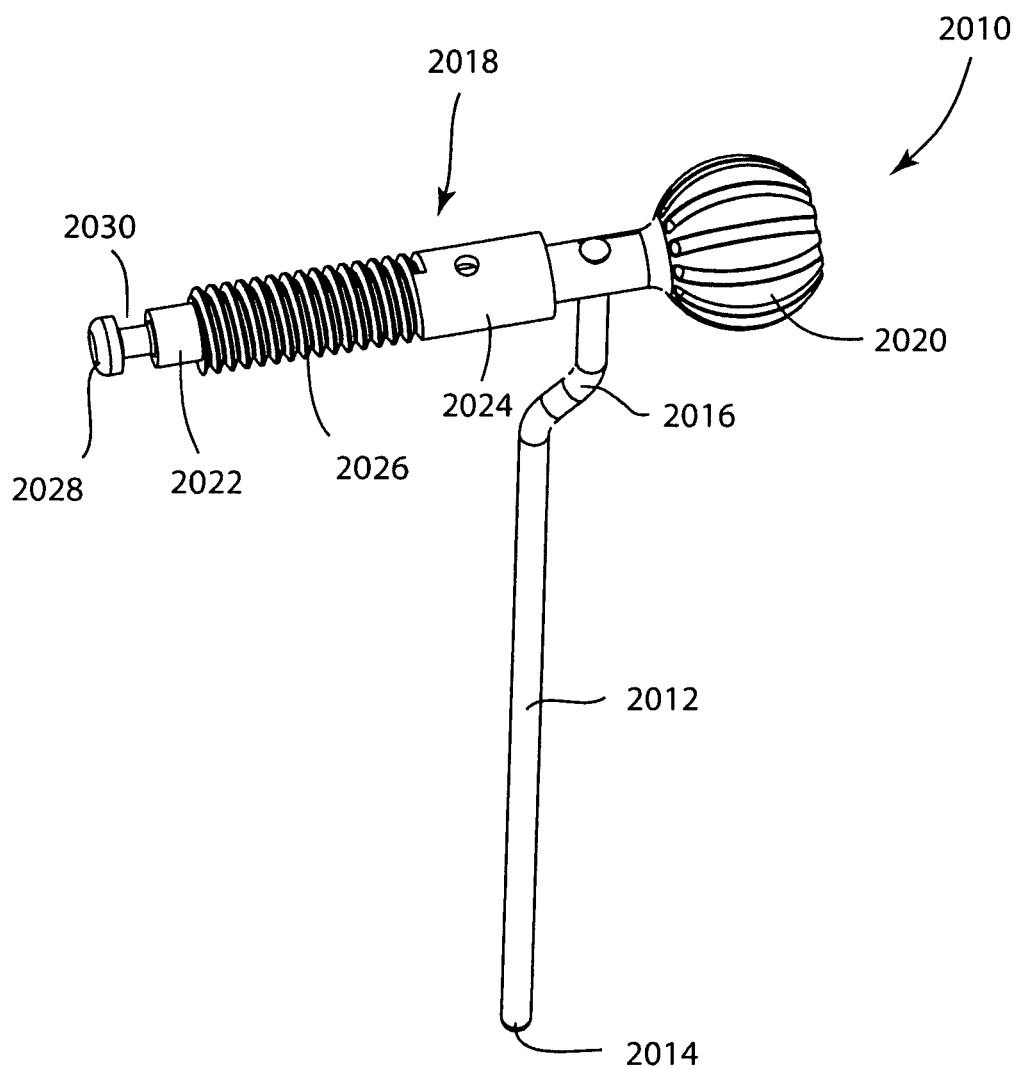
FIG. 59 is a perspective view of the targeting member of FIG. 58.

FIG. 59 illustrates a perspective view of targeting member 2010. Targeting member 2010 comprises a guide post 2012 with a distal end 2014. In some embodiments, guide post 2012 may be cannulated to fit over a guide wire. A proximal portion 2016 of the guide post 2012 may include a dogleg or other offset portion, or may be straight. Proximate to the guide post 2012 is a connection portion 2018, comprising a connection knob 2020 which may be connectable to a table support arm (not shown). The connection portion 2018 further comprises a shaft 2022, which is encircled by a threaded inner sleeve 2024 comprising inner threads 2026, such that the sleeve 2024 is slidable relative to the shaft. Shaft 2022 may be perpendicular to the guide post 2012. A distal end of the shaft 2022 includes an inner knob 2028, and a circular notch 2030 just proximal to the knob 2028. A groove 2032 is incised to extend the length of the shaft 2022.

Figure 60:
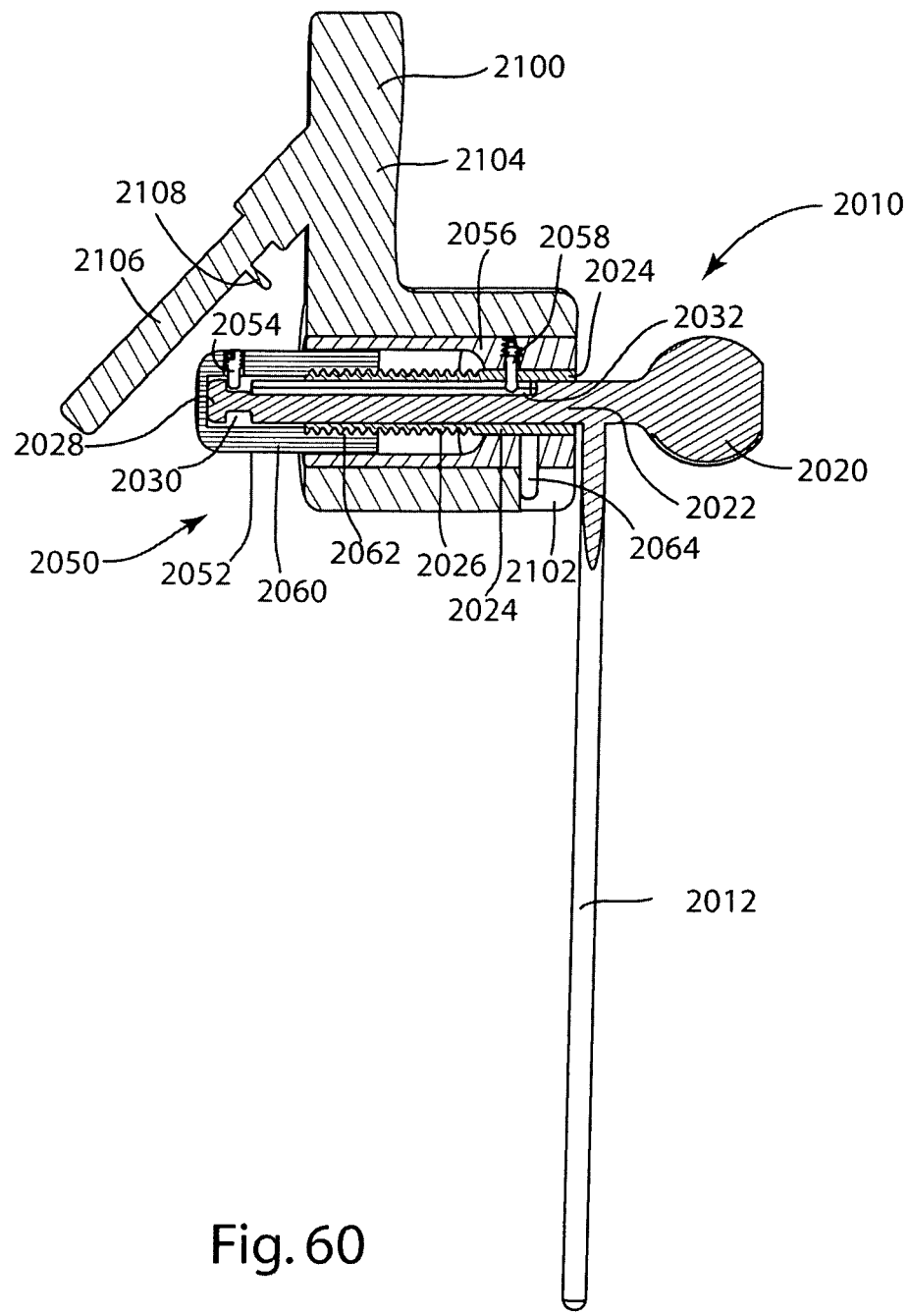
FIG. 60 is a cross-sectional view of the targeting member, micrometer assembly and adapter member of FIG. 58.

FIG. 60 illustrates a cross-sectional view of targeting member 2010, micrometer assembly 2050, and adapter member 2100. Micrometer assembly 2050 comprises micrometer knob 2052, micrometer retaining pin 2054, outer sleeve 2056, and translating pin 2058. The micrometer knob 2052 comprises a cup-like body 2060 with outer threads 2062 disposed inside the cup. The body 2060 is threadibly engaged on the inner sleeve 2024 with the inner threads 2026 engaging the outer threads 2062. The micrometer retaining pin 2054 protrudes into the notch 2030 just proximal to the inner knob 2028. When the micrometer knob 2052 is actuated by turning clockwise, the inner knob 2028 is retained by the micrometer retaining pin 2054, and the inner threads 2026 engage the outer threads 2062 so that the inner sleeve 2024 slides distally along the shaft 2022, and the outer sleeve 2056 moves distally with the inner sleeve. The adapter member 2100 moves distally along with the inner 2024 and outer 2056 sleeves. A first adapter retaining pin 2064 extends posteriorly from the outer sleeve 2056 into a slot 2102 in the adapter member and may prevent the adapter member 2100 from moving proximally relative to the outer sleeve 2056, and prevents rotation of the adapter member around the outer sleeve. A second adapter retaining feature (not shown) may be engaged to prevent the adapter member 2100 from moving distally relative to the outer sleeve 2056. The translating pin 2058 extends through the outer sleeve 2056 and inner sleeve 2024 into the groove 2032 incised in the shaft 2022 and prevents rotation of the inner and outer sleeves relative to the shaft 2022.

When the micrometer knob 2052 is turned counter-clockwise, the inner threads 2026 engage the outer threads 2062 so that the inner sleeve 2024 slides proximally along the shaft 2022 toward the connection knob 2020, and the outer sleeve 2056 and adapter member 2100 move proximally with the inner sleeve. Thus, when the system 2000 is deployed in a spine as depicted in FIG. 58, actuation of the micrometer knob 2052 permits cephalad-caudal adjustment of a distance between the targeting member 2010 and the penetrating member 2200. As the knob 2052 is actuated, the adapter member 2100 translates along shaft 2022 without rotating about the shaft.

Figure 61:
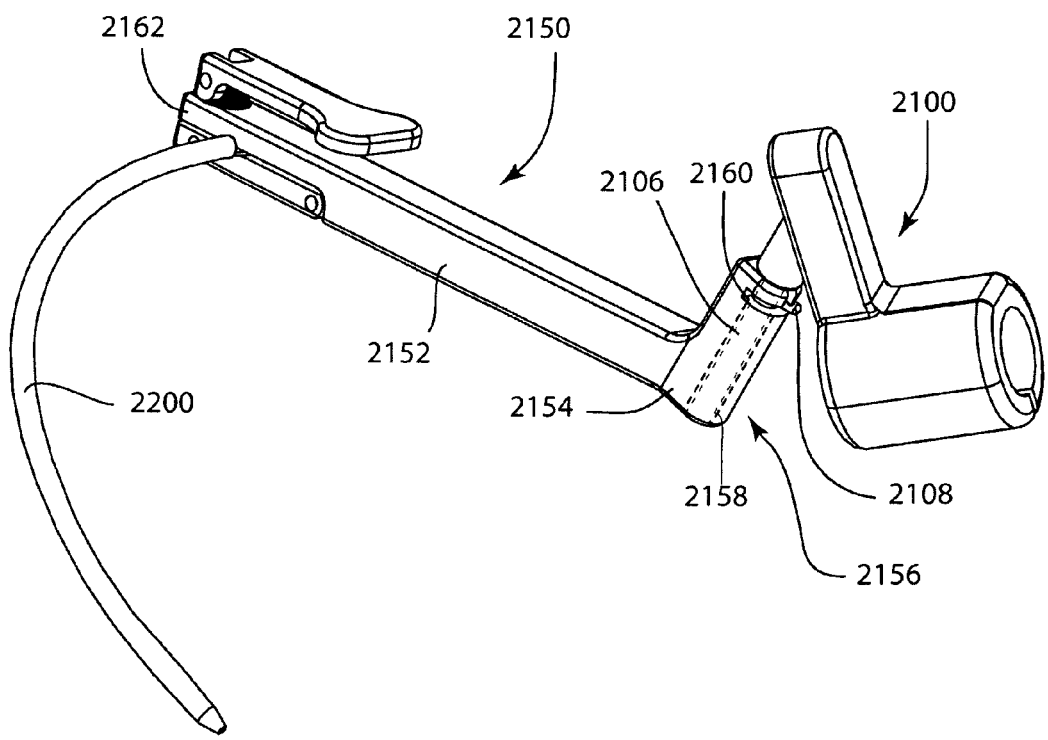
FIG. 61 is a perspective view of the adapter member, swing arm and penetrating member of FIG. 58.

The adapter member 2100 further comprises an adapter body 2104 and a swing arm post 2106 which extends at an angle from the body 2104, and is shaped to connect to the swing arm (not shown). When the adapter member is properly attached to the targeting member, the angle between the swing arm post 2106 and the targeting post 2012 may range from 15° to 75°. More precisely, the angle between the swing arm post 2106 and the targeting post 2012 may range from 30° to 60°. Still more precisely, the angle between the swing arm post 2106 and the targeting post 2012 may be 45°. A swing arm retaining pin 2108 protrudes from the post 2106. Turning to FIG. 61, the adapter member 2100, swing arm 2150 and penetrating member 2200 are shown in an enlarged perspective view. Swing arm 2150 comprises a swing arm shaft 2152. A first end 2154 of the shaft 2152 comprises a receiver portion 2156, which extends at an angle relative to the remainder of the swing arm. The receiver portion 2156 is tube-like, with a lumen 2158 extending therethrough. A semi-circular retaining slot 2160 is located near the terminus of the receiver portion 2156. When joined to the adapter member, the lumen 2158 receives the swing arm post 2106, and the swing arm pin 2108 is received in the retaining slot 2160. Thus joined, the swing arm 2150 may swing, or rotate about the longitudinal axis of the swing arm post 2106, limited by the ends of the semi-circular retaining slot. A second end 2162 of the swing arm 2152 is free, and as the swing arm rotates, moves along a curved path. When the system is deployed at the L4-L5 vertebral level as in FIG. 58, the curved path is in a plane at an angle relative to the cephalad-caudal axis, and may pass cephalad to the iliac crest.

Figure 62:
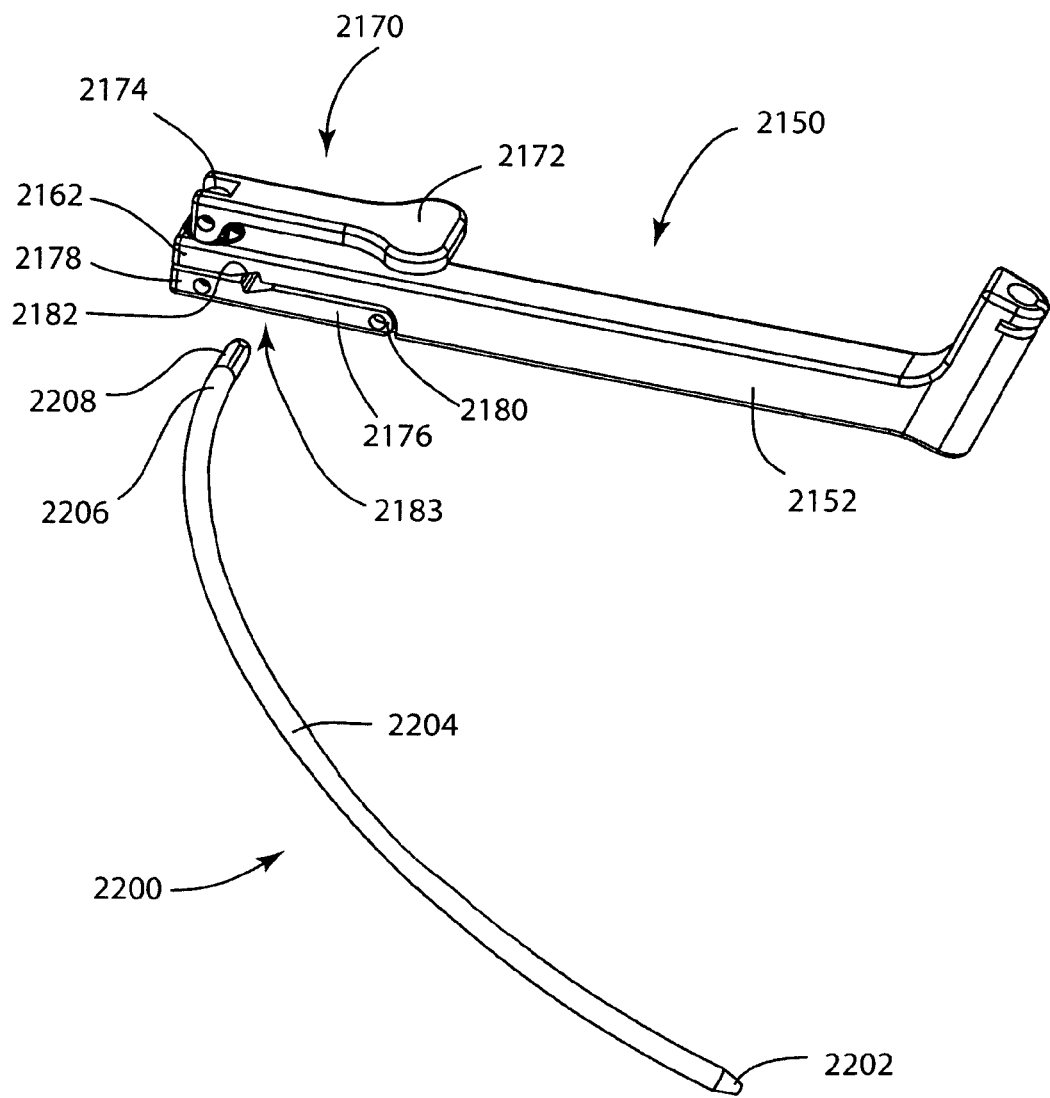
FIG. 62 is a perspective exploded view of the swing arm and penetrating member of FIG. 58.

Referring to FIG. 62, an exploded perspective view of the swing arm 2150 and penetrating member 2200 are shown. At the second end 2162 of the swing arm 2150, a spring-loaded quick release clamp assembly 2170 can be actuated between open and closed positions, and securely clamp a penetrating member such as penetrating member 2200. The clamp assembly 2170 comprises a handle 2172, rod 2174 and a jaw 2176. The jaw is joined to the rod 2174 at a jaw first end 2178, and pivotably attached to the swing arm shaft 2152 at a jaw second end 2180. A spring (not shown) is positioned between the jaw 2176 and the swing arm shaft 2152. As the handle 2172 is raised, the rod 2174 extends, increasing a distance between the jaw 2176 and the swing arm shaft 2152, creating an opening, which may be wedge-shaped. When the handle is lowered, the distance between the jaw and the swing arm shaft decreases. It is understood that clamp assembly 2170 can comprise any other clamping mechanism known in the art. The clamp assembly 2170 comprises a receiving feature 2183 shaped to receive the penetrating member 2200. The receiving feature may comprise at least one clamp flat 2182 shaped to mate with a corresponding portion of the penetrating member 2200. The clamp flat 2182 may be positioned at an angle relative to the longitudinal axis of the swing arm shaft 2125.

Penetrating member 2200 comprises a distal or first end 2202, a curved shaft 2204, and a proximal or second end 2206. The entire length of the penetrating member 2200 may be cannulated to receive a guide such as a guide wire or K-wire. The penetrating member 2200 may comprise an arcuate curve with a fixed radius, and the first and second ends 2202, 2206 may be co-planar. The sweep of the arcuate curve is substantially 90°; however alternate embodiments may comprise an curve which ranges from at least 45° to 135°. The first end 2202 may be blunt, rounded or pointed to dissect bodily tissues. The second end 2206 comprises at least one flat 2208. Flat 2208 may be at an angle relative to the curve of the curved shaft 2204, or at another orientation. Flat 2208 may be shaped to mate with the clamp flat 2182 in the clamp assembly 2170, such that the flats 2208, 2182 may be adjacent and parallel with one another when the penetrating member is received in the receiving feature 2183 in a selected orientation. The penetrating member and/or receiving feature may each include only one flat, so that the penetrating member can be received in only one orientation; or, the penetrating member and/or receiving feature may each include multiple flats, such that the penetrating member can be received in more than one orientation. The penetrating member/receiving feature connection in FIG. 62 is quadrilateral; in other embodiments the connection may be triangular, pentagonal, hexagonal, semicircular, or another shape. When the second end 2206 of penetrating member 2200 is clamped in the receiving feature 2183, and the handle is 2172 is lowered to put the clamp in a closed position, the penetrating member 2200 is firmly gripped by the clamp assembly 2170, and cannot rotate or translate relative to the clamp assembly. Once the penetrating member 2200 is gripped in the clamp assembly 2170, rotation of the swing arm 2150 about the swing arm post 2106 can urge the penetrating member 2200 along a curved path to a targeted location.

Figure 63:
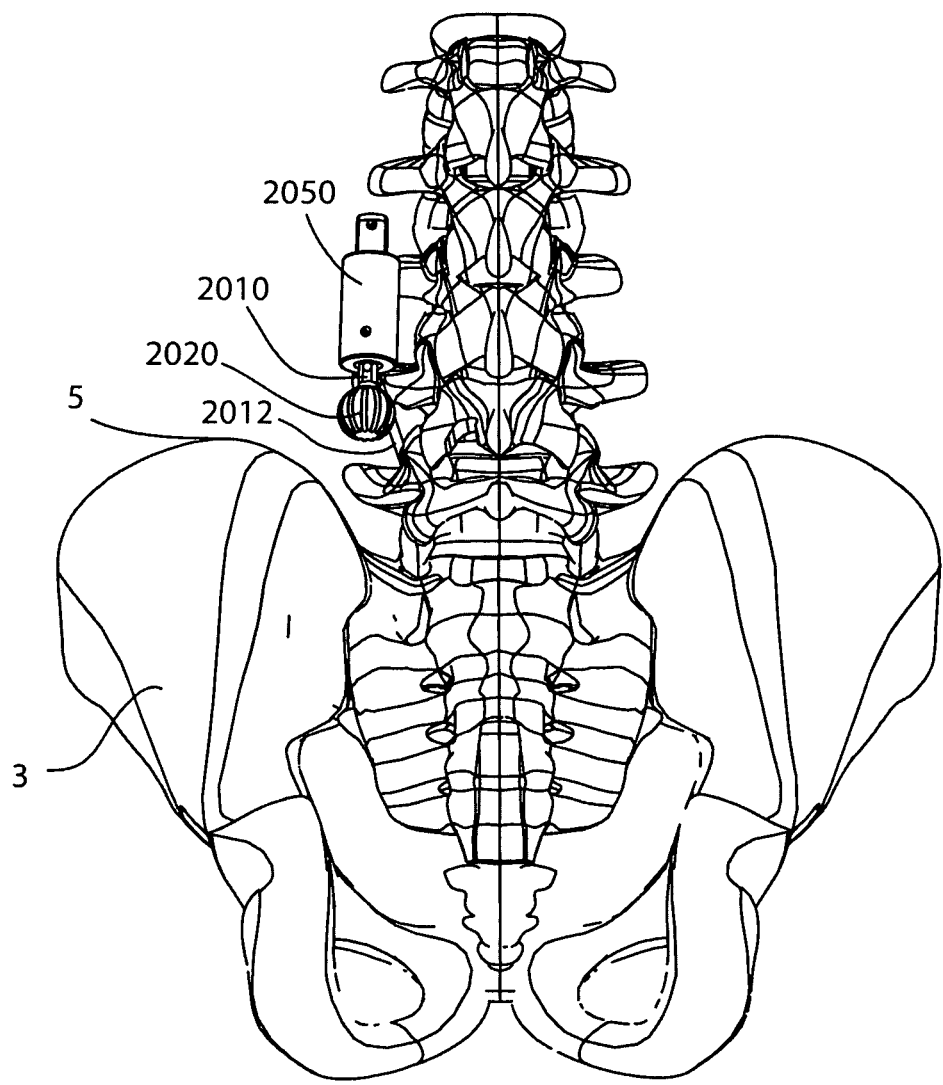
FIG. 63 is a posterior view of the targeting member and micrometer assembly of FIG. 58, the targeting member positioned at a reference location adjacent the spine.

FIGS. 63-67 illustrate use of spinal access system 2000 to create a curved access portal to the intervertebral space at the L4-L5 vertebral level, while avoiding contact with the ilium and without passing through the location occupied by the ilium 3. Referring to FIG. 63, the operative site is targeted. A Jamshidi™, spinal needle or other instrument (not shown) may be inserted at the targeted vertebral level and observed with fluoroscopy to identify the target area adjacent the vertebrae, and to determine the initial incision location for the targeting member 2010. The target location may be the intervertebral area between the L4 and L5 vertebrae. Micrometer assembly 2050 may already be connected to the targeting member 2010, as seen in FIG. 63. The targeting guide post 2012 is inserted adjacent the spine at a point which may be approximately 2.5 cm off the midline, using fluoroscopic guidance. As the post is inserted, its trajectory path may be superior to the transverse process of the inferior vertebra and coplanar with superior endplate of the inferior vertebra. The path may also be parallel to the sagittal plane and/or align with the spinous processes. The distal end of the trajectory path may be mid-disc relative to the anterior-posterior plane. This trajectory path may be similar to an extrapedicular approach for kyphoplasty.

After the targeting post 2012 is positioned with its distal end 2014 at a preferred reference location having a known position relative to the target location, it may be affixed to a table clamp secured to the operating table (not shown). The table clamp system may be the same or similar to system 1500 seen in FIG. 51. Polyaxial clamp assembly 1530 or 1531 may grip connection knob 2020 to hold the targeting assembly 2010 at the preferred location as subsequent procedures are carried out.

Figure 64:
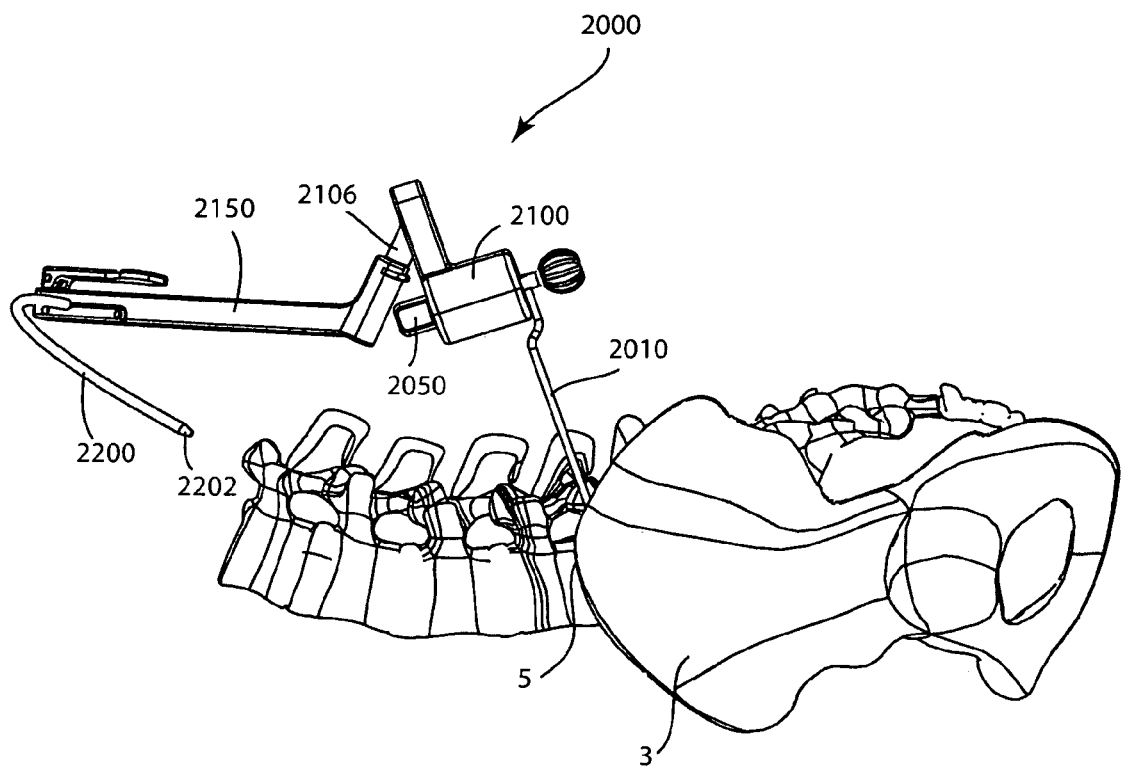
FIG. 64 is a medial view of the spinal access system of FIG. 58 in an open position.

Referring to FIG. 64, the adapter member 2100, swing arm 2150 and penetrating member 2200 are attached to the targeting post 2010 and micrometer assembly 2050. Penetrating member 2200 may be attached to the swing arm 2150 before or after attachment of the swing arm to the adapter member 2100. The swing arm 2150 placed in an open position as seen in FIG. 64, so that the penetrating member 2200 is above the patient's skin. The swing arm 2150 may then be rotated such that the first end 2202 of the penetrating member touches the skin, indicating an initial incision location. This location may be marked on the skin and the swing arm 2150 rotated in the opposite direction to lift the penetrating member 2200 back into an open configuration. Alternately, a guide wire (not shown) may be inserted through the cannulated penetrating member and into the skin to indicate the initial incision location. After the penetrating member is lifted away from the skin, an incision, which may measure approximately 3 cm, is made through the skin and fascia.

Blunt dissection of the tissues between the skin and the target post location may include finger palpation to locate the psoas, peritoneum and retroperitoneum. At least one straight or curved retractor may be inserted to allow visualization of the psoas. A peritoneal retractor similar to retractor 150 (seen in FIG. 28) may be gradually inserted from the incision toward the psoas adjacent the targeted vertebral level, to both shield and retain the tissues. The retractor may be inserted until its rounded distal end comes in contact with the psoas muscle. Once inserted, the proximal end of the retractor may be moved laterally to permit visualization along the retractor; or if two retractors are inserted, they may be moved apart to permit visualization between them. The swing arm is rotated so that the attached penetrating member 2200 is urged caudally and antero-medially along the curved path of the curved guiding surface of the retractor, if present, until the first end 2202 is at the target location adjacent the spine, at a known position relative to the reference location indicated by the distal end 2014 of the targeting post. Neural/EMG monitoring may be used to detect and avoid neural elements during tissue penetration, especially through the psoas.

Before or as the penetrating member 2200 is urged along the curved path, the micrometer assembly 2050 may be actuated to provide a cephalad-caudal adjustment to the path of the penetrating member. Micrometer knob 2052 may be rotated as described in reference to FIG. 60, to move the penetrating member 2200 cephaladly or caudally, so that the desired target location may be reached. This adjustment may also be implemented to avoid neural elements. It is appreciated that a second micrometer assembly (not shown) could be implemented to provide anterior-posterior adjustment to the penetrating member 2200. In addition, the penetrating member 2200 can be unclamped from the swing arm 2150 and manually moved. During insertion of the penetrating member 2200, if a neural element is encountered that cannot be avoided by adjustment of the path, the system may be withdrawn and the procedure may be converted to the contralateral side of the patient, without repositioning the patient. In another embodiment, two spinal access systems may be deployed, one on each lateral side, permitting access to the intervertebral space from both sides simultaneously. Or if a neural element is encountered that cannot be avoided by adjustment of the path, in another alternative the system may be withdrawn and a posterior lumbar interbody fusion or transforaminal lumbar interbody fusion procedure may be carried out without repositioning the patient.

Figure 65:
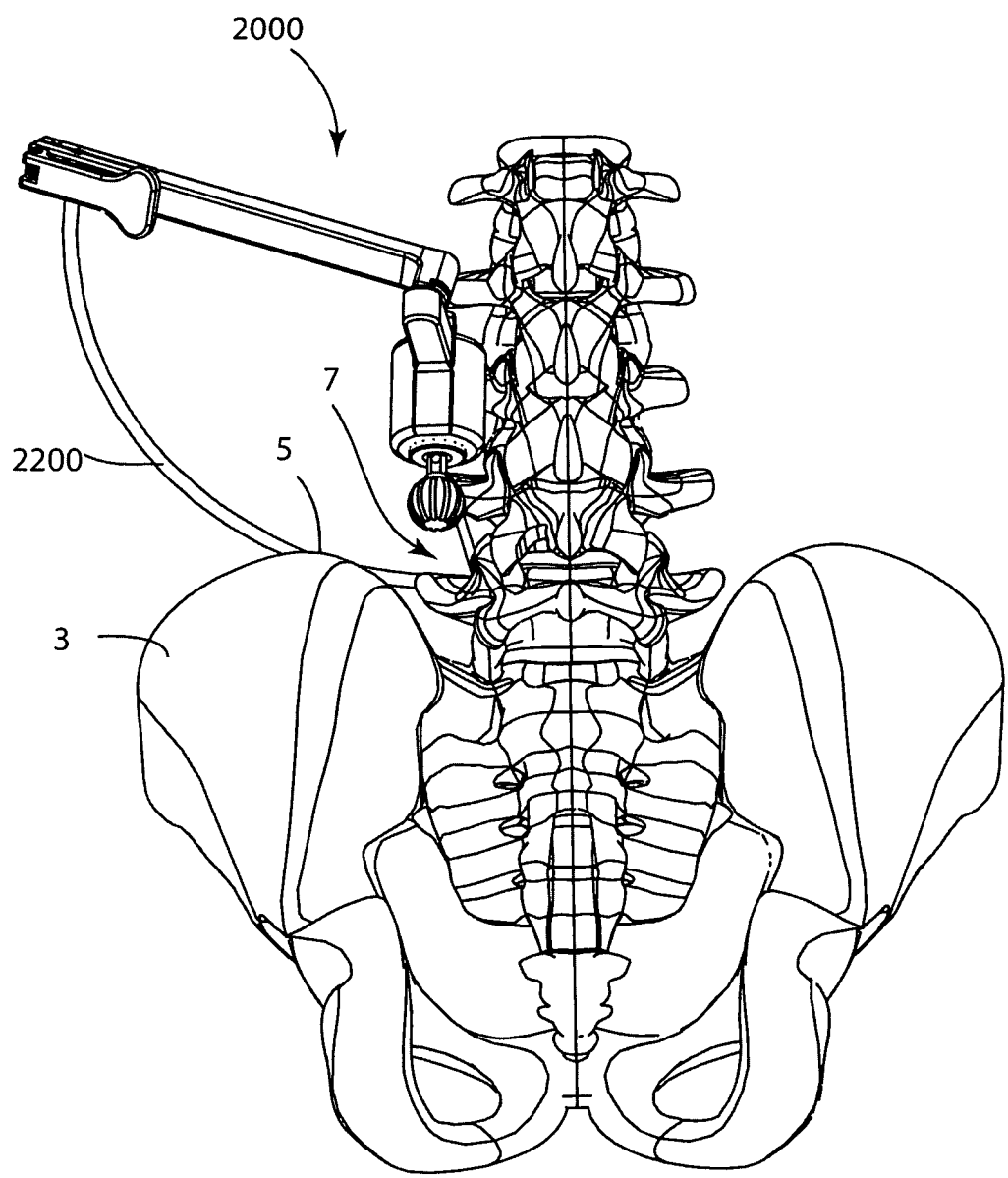
FIG. 65 is a posterior view of the spinal access system of FIG. 59 in a closed position.
Figure 66:
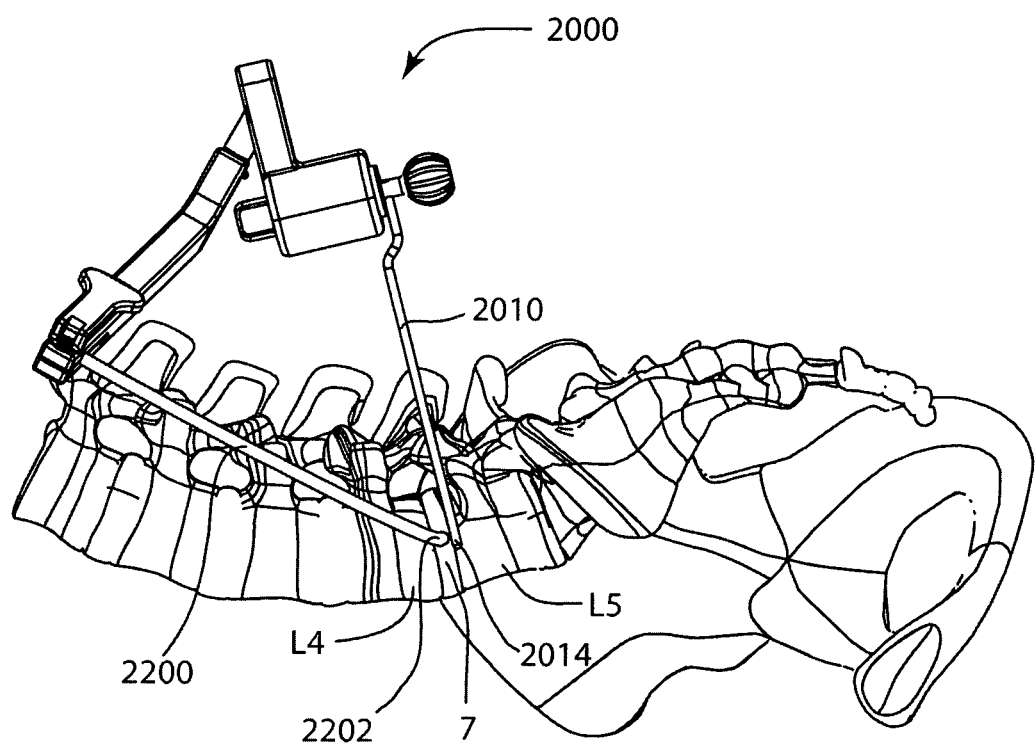
FIG. 66 is a medial view of the spinal access system of FIG. 59 in a closed position.

FIG. 65 illustrates a posterior view of the spinal access system 2000 with the swing arm 2150 rotated such that the penetrating member 2200 extends along a curvate path from the incision in the skin to the desired target location at the intervertebral location 7 between the L4 and L5 vertebrae. Penetrating member 2200 passes cephalad to the iliac crest 5, then anterior to the ilium 3. FIG. 66 illustrates a medial view of the spinal access system 2000 in the same position as FIG. 65, with the ilium removed. It is appreciated that the curvate path of the penetrating member may be arcuate, with a fixed radius. It is also appreciated that a first end of the curvate path may be substantially perpendicular to a second end of the curvate path. The curvate path may extend obliquely in a plane which is at an angle relative to the cephalad-caudal axis of the body, and at an angle relative to the transverse plane of the body. Additionally, the incision in the skin may be cephalad to the iliac crest, while the target location is proximate the spine and caudal to the iliac crest.

When the first end 2202 of the penetrating member 2200 is at the desired target location, a K-wire may be inserted through the cannulated penetrating member 2200 to penetrate the disc annulus, and/or the first end 2202 may penetrate the disc annulus. The dense fibrous network of the annulus may further anchor the penetrating member 2200 and/or wire at the target location. The swing arm 2150 may be detached from the penetrating member 2200, and the targeting post 2010 with the associated micrometer assembly 2050 and adapter member 2100 may be removed.

To dilate the tissues around the penetrating member 2200 sufficiently to create access to the target location, a series of graduated curved cannulas such as 15, 17 and 18 may be inserted one at a time over the proximal second end 2206 of the penetrating member 2200, and advanced caudally and antero-medially over the member 2200 until the corresponding distal end reaches the distal first end 2202 of the penetrating member 2200 at the target location. At this point, the opening in the distal end of the cannula(s) may be tangential to the intervertebral space between the L4 and L5 vertebra. Also, the distal end of the cannula(s) may touch the L4 and/or L5 vertebral bodies. After the largest cannula is inserted, any intermediate cannulas and the penetrating member and wire may be removed, leaving an open access portal through the largest, or "working" cannula to the targeted intervertebral area. One or more of the cannulas may include a radioopaque marker system similar to visual referencing system 1450 described previously with reference to FIGS. 48-50; however placement of the markers may be shifted 45° to allow for proper referencing to the spine from this approach. The visual referencing system may be deployed to assist in fine-tuning the placement of the cannula(s) and access portal relative to the intervertebral area.

A tang assembly similar to tang assembly 1350 seen in FIGS. 44-47 may be inserted through the working cannula to provide tissue retraction. In addition, the penetration of the tangs through the annulus will further dock the system in its preferred position. For use with spinal access system 2000 to create access to the L4-L5 intervertebral level, the tang assembly may include tang extensions placed at a 45° angle relative to the handles. Thus the tangs would enter the intervertebral space in anterior and posterior positions suitable for anterior and posterior tissue retraction and protection of neural elements.

Figure 67:
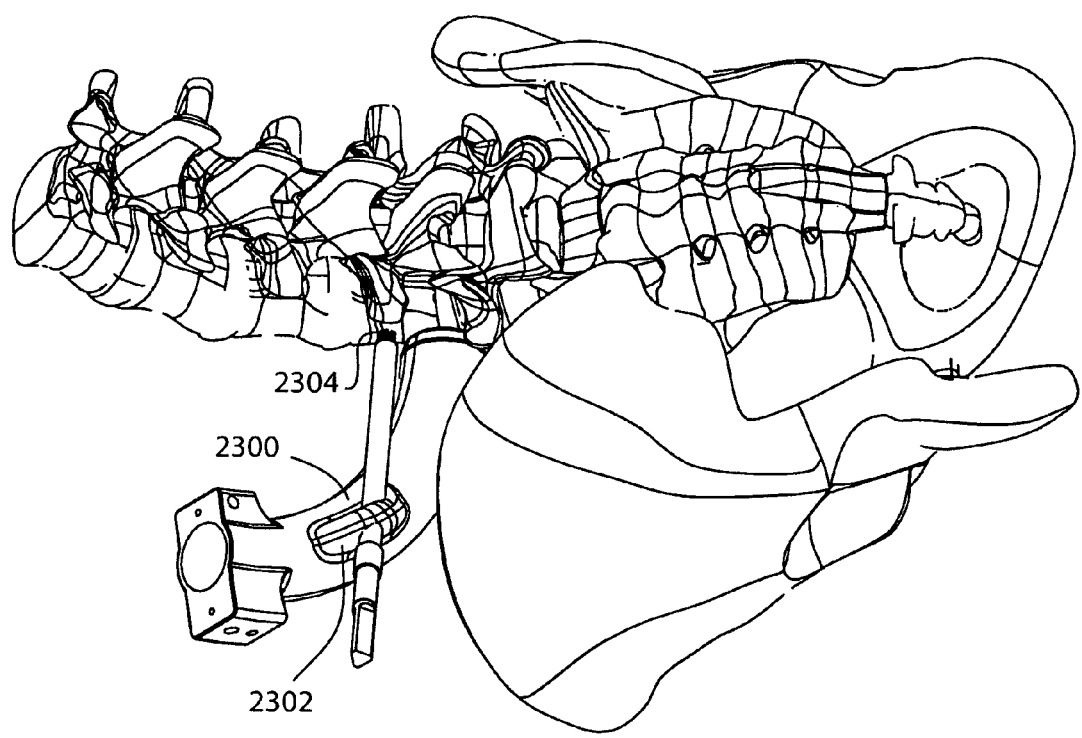
FIG. 67 is a postero-medial view of a curved cannula adjacent an intervertebral space, secured to the L4 vertebra by a vertebral body screw.

The working cannula may be connected to a table clamp system such as system 1500 described previously with reference to FIGS. 51-53. In addition or as an alternative to the table clamp system, a vertebral body docking assembly similar to assembly 1750 may be deployed to further anchor the working cannula to the spine. FIG. 67 illustrates a working cannula 2300 which includes a guide bracket 2302. Guide bracket 2302 may be positioned so that a bone screw 2304 may pass through the guide bracket and enter the vertebral body at an orientation substantially parallel to the intervertebral space. Instruments with curved shafts such as those illustrated in FIGS. 17-27 may be inserted through the lumen of the working cannula to accomplish procedures such as, but not limited to, annulotomy, nucleotomy, discectomy, annulus replacement, nucleus replacement, and decompression. On some instruments, the working end may be rotated 45° in order to enter the L4-L5 intervertebral space at a desired orientation. Additional instruments comprising curved shafts shaped to be inserted through the curved cannula systems described herein may include annulotomy knives, box chisels, annulus cutters, pituitaries, shavers, wire brushes, and trials, among others.

Visualization systems and methods such as those described with reference to FIGS. 35-42 may be deployed to visualize procedures carried out through the access portal to the L4-L5 intervertebral level. It is appreciated that the placement of handles, mirrors, light sources or other portions of the visualization systems may be shifted 45° from those depicted in FIGS. 35-42 to permit visualization through the working cannula along the oblique approach.

Figure 68:
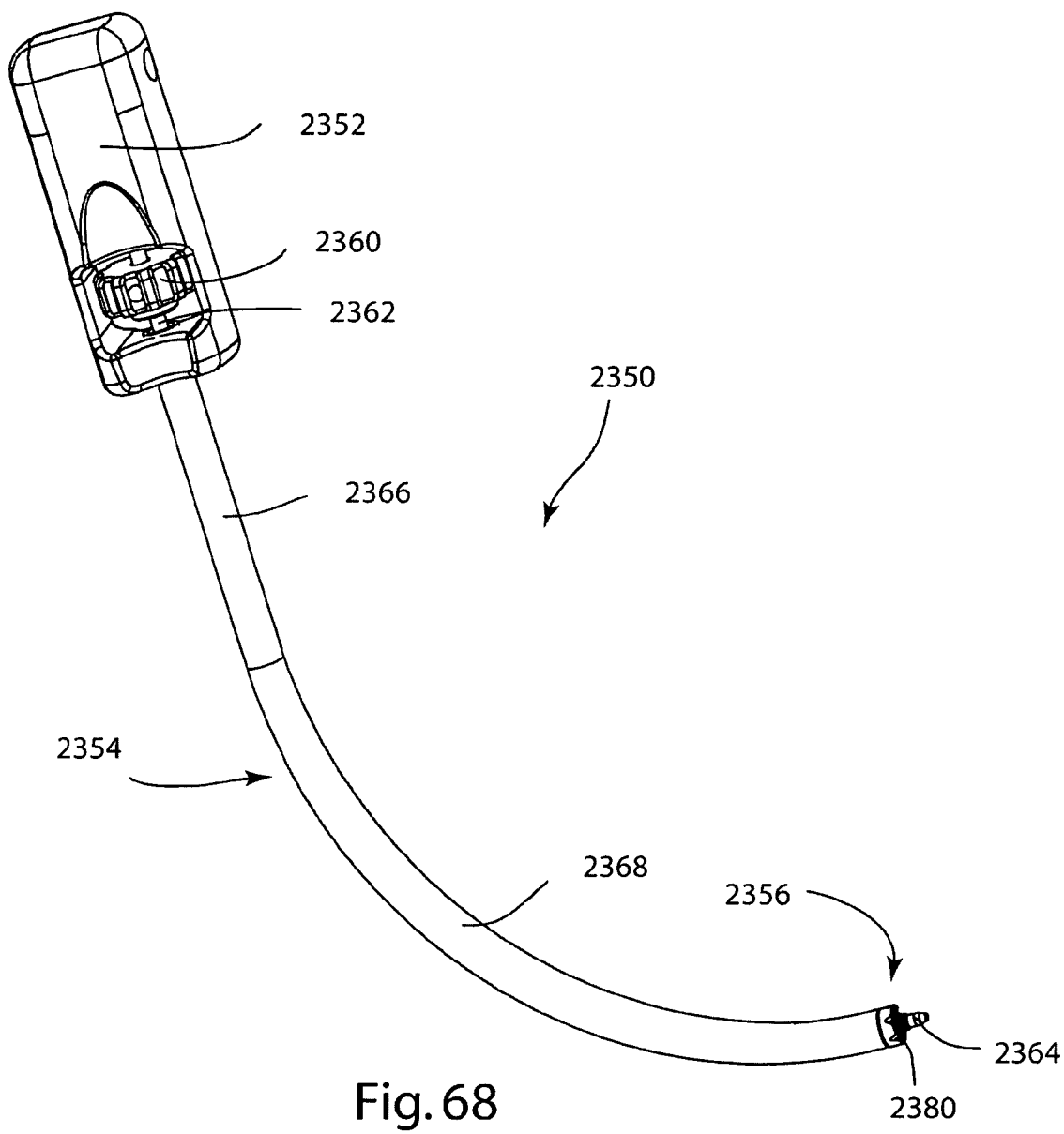
FIG. 68 is a perspective view of an intervertebral implant inserter.
Figure 69A:
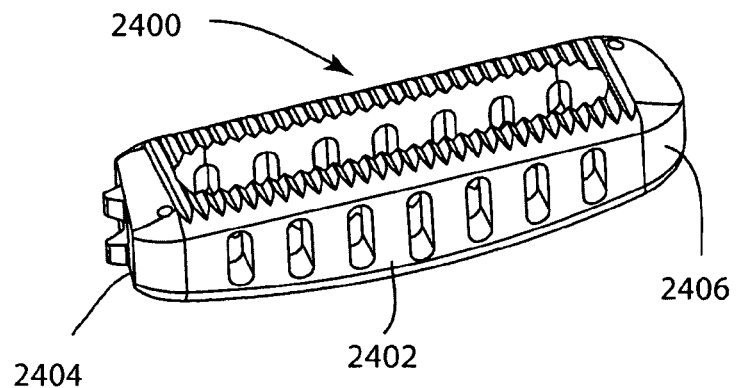
FIG. 69A is a perspective view of a fusion cage.
Figure 69B:
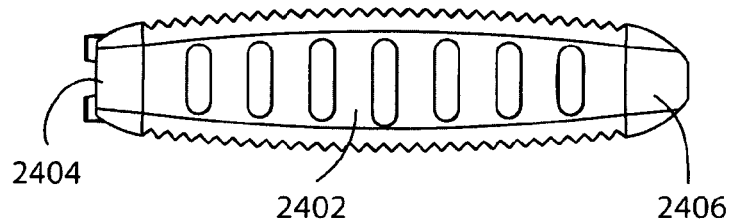
FIG. 69B is a side view of the fusion cage of FIG. 69A.
Figure 69C:
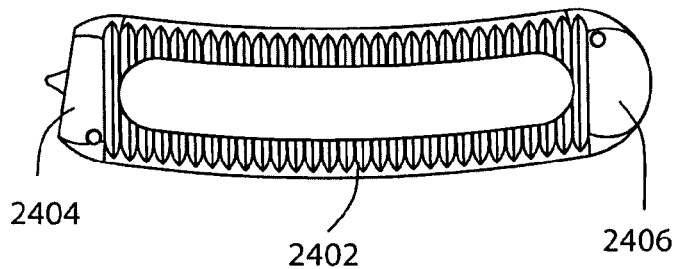
FIG. 69C is a top view of the fusion cage of FIG. 69A.
Figure 69D:
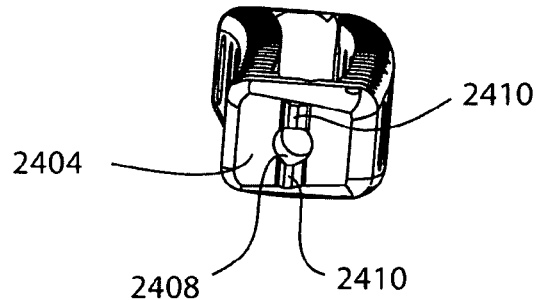
FIG. 69D is an end view of the fusion cage of FIG. 69A.

Referring to FIG. 68, a perspective view of an implant inserter 2350 is shown. Inserter 2350 comprises a curved shaft portion and an implant connection feature which can be actuated to selectively connect to an intervertebral implant, and release the implant. Inserter 2350 comprises a handle 2352, a shaft 2354, and a connection feature 2356. The handle 2352 is connected to the shaft 2354, which comprises a first portion 2366 and a second portion 2368. Either of both of the first and second portions may be curved, such that at least a portion of the shaft may be inserted to extend through the length of a curved cannula such as cannula 18 or 2300. Situated in the handle 2352 is an opening 2358 within which a release knob 2360 is located. Extending distally from the release knob 2360 is a flexible line 2362, which extends through the length of the shaft 2354, terminating distal to a distal end of the shaft. At the distal end of the flexible line is a threaded stem 2364. At the distal end of the shaft, a plurality of notches 2380 are cut into the end of the shaft, at locations distributed around the shaft opening.

Referring to FIGS. 69A through 69D, four views of an intervertebral fusion cage 2400 are shown. Fusion cage 2400 is generally quadrilateral in shape, having a curved body 2402 with a first end 2404 and a second end 2406. The first end 2404 has an inserter interface comprising an opening 2408 and at least one tab 2410. Tabs 2410 are shaped to mate with the notches 2380 on the inserter. The opening 2408 may be threaded, to engage with the threaded stem 2364 on the inserter. The tabs 2410 are configured on the fusion cage so that the fusion cage 2400 may be connected to the connection feature 2356 on the inserter at a variety of orientations, allowing the cage to be inserted into the intervertebral space from a postero-lateral approach which may be oblique. The fusion cage 2400 may be attached to the inserter by threading the opening 2408 onto the stem 2364 and fitting the tabs 2410 into the notches 2380 at the desired orientation. The cage 2400 is inserted through the curved cannula 18 or 2300 and into the intervertebral space. When at a desired location in the intervertebral space, the release knob 2360 is actuated to rotate the flexible line 2362 and stem 2364, unthreading the stem from the cage 2400. The inserter 2350 may be withdrawn from the curved cannula. It is appreciated that additional tools may be inserted through the cannula to further adjust or seat the implant. It is also appreciated that other intervertebral implants may be delivered to the intervertebral space in the same manner.

The arcuate postero-lateral approaches described above may have many advantages for spinal procedures, particularly procedures involving anterior vertebral column elements. These approaches may be used to insert motion preservation devices, such as total disc replacements. By accessing the disc space via an arcuate postero-lateral approach, the surgeon is able to spare the anterior longitudinal ligament as well as avoid complications with the great vessels. These approaches also provides for revision options with virtually the same instrumentation and implant designs by accessing the disc space from the opposite lateral side as the first surgery. These approaches also allows for total disc replacement (TDR) endplate retention features which are more desirable than anterior approach TDR features, such as endplate keels or teeth which are oriented in the frontal plane to resist the high shear loads seen in the lumber spine lordotic region.

These approaches may also be used for various intervertebral disc treatment or resection procedures such as annulotomy, nucleotomy, discectomy, annulus replacement, nucleus replacement, and decompression due to a bulging or extruded disc. During an annulotomy, the surgeon may provide an access portal in the manner described previously, and open and/or remove a portion or all of the disc annulus. During a nucleotomy, the surgeon may provide an access portal in the manner described previously, and open and/or resect a portion of the intervertebral disc nucleus. During a discectomy, the surgeon may remove a portion or the entire intervertebral disc through the access portal in order to accomplish decompression of the nerve roots, dura, or spinal cord. This procedure may be done as a conservative therapy to relieve patient symptoms or pain, or it may be done in preparation for total disc replacement or fusion.

For annulus repair or replacement, the arcuate postero-lateral approach may facilitate a larger needle and avoidance of complicated vascular structure and may allow a pathway for a prosthetic annulus to be placed or formed in the intervertebral space. Using a bilateral arcuate approach such as that depicted in FIG. 14 could further facilitate the creation of bounding elements, such as a shield, guard, mold, or equivalent such that the annulus may be repaired, formed, inserted, created, or augmented. Similar benefits are realized for a nucleus replacement procedure where all or a portion of the intervertebral nucleus is repaired or resected and replaced, created or augmented via various techniques. A prosthetic nucleus may be delivered via a passageway that is larger than that afforded by a transpedicular approach, and less complicated and less risky than an anterior approach, by using the arcuate postero-lateral approach described above. Various intervertebral disc treatment methods have been postulated, such as using electrosurgical therapies. It is readily apparent to one of skill in the art how conducting these therapies via an arcuate postero-lateral approach may benefit the surgeon as well as improve clinical outcomes.

The arcuate postero-lateral approach may also be utilized for additional vertebral body motion segment stabilization procedures such as interbody device insertion, lateral plating, anterior plating, lateral or anterior plating with dynamic stabilization or compression elements, deformity correction, and/or graft compression devices or procedures. The arcuate postero-lateral access portal such as that depicted in FIG. 15A or 67 may facilitate interbody fusion procedures by allowing a single surgical exposure or patient positioning to insert all required stabilization elements such as an interbody fusion device similar to that depicted in FIG. 15B or 68, or posterior stabilization hardware such as pedicle screws, rods, hooks, and facet screws, among others. By approaching the intervertebral disc space with a tangential or almost straight medial-lateral trajectory right next to the vertebral body, the interbody device may more fully occupy the intervertebral space. This may result in a multitude of advantages such a leveraging the higher strength cortical regions on the vertebral body endplates, allowing more cross-sectional surface area or a larger footprint for improved stability, allowing more bone graft surface are to encourage better osteointegration, bony fusion, and 360° fusion. The interbody device may also comprise a lordotic angle which does not require over-distraction such as is the case with transforaminal lumbar interbody fusion (TLIF) and posterior lumbar interbody fusion (PLIF) procedures.

The arcuate postero-lateral approach may also be used for lateral plating procedures, in which the implanted plates may comprise fixed, dynamic, or compressive elements. This approach again allows a single patient positioning to conduct lateral plating as well as posterior stabilization hardware such as screws, hooks and rods. These plates may be used for local deformity correction or prevention procedures to treat local scoliosis, kyphosis, hyper-lordosis, or spondylolisthesis. Additionally, the arcuate postero-lateral approach may allow for novel graft compression devices or procedures that enable the surgeon to apply improved local compressive forces between vertebral bodies or an interbody device. Benefits of improved local compressive forces include improved bone graft incorporation, fusion, interbody device stability, as well as a potentially reduced risk of interbody device expulsion that is often the result of over-compressing the disc space and applying unintended moments via traditional pedicle screws and rods. Such graft compression devices include lateral plates with compression features, vertebral body staples which cooperate with the superior and inferior vertebral bodies to apply compression, and integrated interbody device with arms that cooperate with the vertebral bodies to apply compression via screws, tapered surfaces, or the like.

Various central canal or foraminal decompression procedures may be performed with the arcuate postero-lateral approach described previously. Decompression procedures are conducted to resect soft or hard tissues that may be impinging on neural elements such as the exiting nerve roots, dura, or spinal cord, resulting in various pathologies such as radiculopathy, myelopathy, pain, tingling, numbness, and loss of motor or sensory control. For example, anterior central canal decompression required due to a diseased intervertebral disc is often a difficult procedure. By using the disclosed arcuate postero-lateral approach, this decompression procedure allows for improved patient positioning, access, and patient outcomes. Foraminal decompression procedures via an arcuate postero-lateral approach may also allow the surgeon an improved trajectory and passageway to decompress the foramen.

Procedures involving the vertebral body, such as vertebral body biopsy, vertebral body height restoration, and vertebroplasty may successfully utilize the arcuate postero-lateral approach. Often patients who are experiencing symptoms associated with vertebral body disease, collapse, or fracture will undergo a biopsy of the vertebral body to assess the condition of the structure. Osteoporotic patients, especially female geriatric patients, may experience vertebral body collapse or fracture. This is an extremely painful and debilitating condition which may be addressed via vertebroplasty through the disclosed arcuate postero-lateral approach. Often, vertebroplasty, kyphoplasty or arcuplasty procedures are conducted via a transpedicular approach, to inject a hardenable compound such as PMMA cement into the vertebral body to create an internal cast-like structure to stabilize the bony fragments or fractures. The arcuate postero-lateral approach has numerous advantages for such a procedure. It may allow for a larger access needle than a transpedicular approach and accordingly reduces pressure requirements for the viscous hardenable compounds. In addition, it will likely result in less post-operative pain due to not violating the pedicle, and it allows for a more preferable trajectory of the access needle. Vertebroplasties conducted via a transpedicular approach often require a bilateral approach for sufficient vertebral body stabilization. By using the trajectory of the arcuate postero-lateral approach, the surgeon or radiologist may use a single needle and single approach for a complete fill, because the access needle can be advanced to the distal portions and gradually retracted during injection to accomplish a complete fill.

Vertebral body height restoration procedures have recently been disclosed in the art to address collapsed vertebral bodies. The arcuate postero-lateral approach may facilitate such vertebral height restoration procedures by removing the size limitation imposed by the transpedicular approach. Additionally, the ability to access the lateral margins of the vertebral body may be beneficial in insertion of an implant to restore vertebral height and fix it in place via a hardenable compound, or conduct an internal vertebral body distraction and secure the vertebral body via a hardenable compound.

The present invention may be embodied in other specific forms without departing from its spirit or essential characteristics. For example, above are described various alternative examples of systems for accessing intervertebral space. It is appreciated that various features of the above-described examples can be mixed and matched to form a variety of other alternatives. It is also appreciated that this system should not be limited creating access to the intervertebral space. This arcuate access system may be used to obtain access to any portion of the spine. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for creating access to a location proximate a portion of a spine, the system comprising:
  a targeting post comprising a first end positionable at a reference location proximate the spine;
  a curved guide member having a proximal end and a distal end;
  an adapter member having an attachment mechanism for attaching the adapter member to a second end of the targeting post, the attachment mechanism being configured to prevent rotation of the adapter member with respect to the targeting post, and a swing arm post projecting from the adapter member, the swing arm post having a first axis positioned at a fixed angle in a range of approximately 15 degrees to approximately 75 degrees relative to the targeting post; and
  a swing arm having a first end configured for rotating attachment to the swing arm post of the adapter member and a second end configured for nonrotating attachment to the proximal end of the curved guide member;
  whereby, when the adapter member is attached to the second end of the targeting post, and the first end of the swing arm is attached to the swing arm post of the adapter member, and the curved guide member is attached to the second end of the swing arm, the curved guide member is rotatable about the first axis to advance the distal end of the curved guide member to a target location having a known position relative to the reference location.

2. The system of claim 1,
  wherein the first end of the swing arm has a tubular receiver portion configured to fit over the swing arm post of the adapter member, the tubular receiver portion having an approximately semi-circular retaining slot, wherein a swing arm pin is received in the retaining slot to retain the swing arm on the swing arm post, whereby the swing arm may rotate about the first axis of the swing arm post, and wherein rotation of the swing arm is limited by first and second ends of the retaining slot.

3. The system of claim 1, wherein the adapter member comprises an adjustment feature actuable to selectively increase or decrease a cephalad-caudal displacement between the targeting post and the distal end.

4. The system of claim 1,
  wherein the second end of the swing arm is releasably connected to the proximal end of the curved guide member.

5. The system of claim 1, wherein the proximal end and the distal end of the curved guide member are co-planar.

6. The system of claim 5, wherein the curved guide member has a shape that extends along an arcuate path.

7. The system of claim 1, further comprising:
  a curved cannula comprising a bore shaped to receive the curved guide member as the curved cannula is slid over the curved guide member about the first axis, wherein after withdrawal of the curved guide member from the bore, the bore provides an access portal to the target location.

8. The system of claim 7, further comprising an interbody fusion implant shaped to be inserted through the bore.

9. The system of claim 1, wherein the target location is caudal to the L4 vertebra and cephalad to the L5 vertebra.

10. The system of claim 1, wherein the curved guide member is rigid.

11. The system of claim 1, wherein the first axis is at a 45 degree angle relative to the targeting post.

12. The system of claim 1, wherein the attachment mechanism includes a cylindrical member extending laterally from the second end of the targeting post, a slot in the adapter member, and an adapter retaining pin extending from the cylindrical member into the slot to retain the adapter member on the cylindrical member and to prevent rotation of the adapter member with respect to the cylindrical member and the targeting post.

13. The system of claim 1, wherein the first axis is at an angle in a range from approximately 30 degrees to approximately 60 degrees to the targeting post.

* * * * *